US005702933A

United States Patent [19]

Klee et al.

[11] Patent Number: 5,702,933
[45] Date of Patent: *Dec. 30, 1997

[54] CONTROL OF FRUIT RIPENING AND SENESCENCE IN PLANTS

[75] Inventors: Harry John Klee, Ballwin; Ganesh Murthy Kishore, Chesterfield, both of Mo.

[73] Assignee: Monsanto Company, St. Louis, Mo.

[*] Notice: The term of this patent shall not extend beyond the expiration date of Pat. No. 5,512,466.

[21] Appl. No.: 553,943

[22] Filed: Nov. 6, 1995

Related U.S. Application Data

[63] Continuation of Ser. No. 809,457, Dec. 17, 1991, Pat. No. 5,512,466, which is a continuation-in-part of Ser. No. 632,440, Dec. 26, 1990, abandoned.

[51] Int. Cl.$^6$ ............ C12N 15/31; C12N 15/63; C12N 15/82; A01H 5/08
[52] U.S. Cl. ............ 435/172.3; 435/172.1; 435/69.1; 435/70.1; 435/227; 435/320.1; 435/375; 800/200; 800/205; 536/23.2; 536/23.7; 47/58
[58] Field of Search ............ 800/200, 205, 800/DIG. 9, 10, 13, 15, 16, 18, 19, 27, 30, 31, 34, 36, 37, 52, 29, 17, 68, 63, 64, 65; 435/172.3, 320.1, 69.1, 70.1, 227, 375, 172.1; 47/58; 536/23.2, 23.7

[56] References Cited

U.S. PATENT DOCUMENTS

| | | | |
|---|---|---|---|
| 4,801,540 | 1/1989 | Hiatt et al. | 435/172.3 |
| 4,843,186 | 6/1989 | Nabum | 800/200 |
| 4,943,674 | 7/1990 | Houch et al. | 800/205 |
| 5,480,789 | 1/1996 | Firoozabady et al. | 435/172.3 |
| 5,512,466 | 4/1996 | Klee et al. | 435/172.3 |

FOREIGN PATENT DOCUMENTS

| | | |
|---|---|---|
| 0 271 988 | 6/1988 | European Pat. Off. . |
| 0 409 625 | 1/1991 | European Pat. Off. . |
| WO 91/01375 | 2/1991 | WIPO . |
| WO 91/09112 | 6/1991 | WIPO . |
| WO 91/16417 | 10/1991 | WIPO . |

OTHER PUBLICATIONS

M–C. Chupeau et al. BioTechnology ('89) 7:503–7.
Barton et al., Plant Physiology, 85:1103–1109 (1987).
Bouzayen et al., Planta, 180: 175–180 (1990).
Christoffersen et al., Planta, 155: 52–57 (1982).
Hamilton et al., Nature, 346: 284–287 (1990).
Honma et al., Agric. Biol. Chem., 42(10): 1825–1831 (1978).
Kende, Plant Physiology, 91: 1–4 (1989).
Lizada et al., Analytical Biochemistry, 100:140–145 (1979).
McGarvey et al, Plant Mol. Biol., 15: 165–167 (1990).
Slater et al., Plant Mol. Biol., 5: 137–147 (1985).
Vaeck et al., Nature, 328: 33–37 (1987).
E Shahin, "Isolation & Culture of Proto. Plants Plass: Tomato" in, Cell Culture and Samatio Cell Genetics of Polants, vol. 1 (1984) Academic Press NY, pp. 370–380.
Yang, S. F., et al. Ann. Rev. Plant Physiol., vol. 35 (1984) pp. 155–189.
Walsh, C, et al. Biochem., vol. 20 (1981) pp. 7507–7519.
Aebersold, R., et al. Proc. Nat. Acad. Sci., vol. 84 (1987) pp. 6970–74.
Jaye, H., et al. Nucl. Acids Res., vol. 11 (1983) PP. 2325–35.
McCormick, S., et al. Plant Cell Repute, vol. 5 (1986) pp. 81–84.
Devlin, R. Plant Physiology 3rd Ed. NY, NY Dovam Nostrand Co., 1975, pp. 436 & 507–508.
Deikman, J., et al EMBO Journal, vol. 7 (1988) pp. 3315–3320.
Sanger, M., et al. Plant Mol Biol., vol. 14, (1990) pp. 433–443.
Sanders, P. R. Nucl. Acid. Res., vol. 15 (1987) pp. 1543–1558.
Harpster, M. H. Mol. Gen. Genetics, vol. 212 (1988) pp. 182–190.

Primary Examiner—Charles C. P. Rories
Attorney, Agent, or Firm—Grace L. Bonner; Melinda L. Patterson

[57] ABSTRACT

A method for controlling the ripening of fruits and vegetables as well as a method for controlling senescence of plant tissue is described. The method generally embraces the expression of an ACC metabolizing enzyme in the fruit or other desired plant tissue to inhibit the production of ethylene in the fruit or plant tissue. The use of the ACC metabolizing enzyme ACC deaminase is described in detail. The ripening or senescence process in the fruit or plant tissue is inhibited by the expression of the ACC deaminase gene such that the shelf-life and marketability of the fruit or plant is enhanced. The ACC metabolizing enzyme may be used in combination with other methods for reducing ethylene production in transformed plants to further reduce the production of ethylene in the fruit or plant. DNA constructs containing the ACC deaminase gene are also described.

19 Claims, 30 Drawing Sheets

| Strain | Number of Isolates Tested |
|---|---|
| *Pseudomonas putida* biovar A | 58 |
| *Pseudomonas putida* biovar B | 23 |
| *Pseudomonas chlororaphis* | 170 |
| *Pseudomonas tolaasii* | 41 |
| *Pseudomonas aureofaciens* | 28 |
| *Pseudomonas corrugata* | 13 |
| *Pseudomonas fragi* | 18 |
| *Pseudomonas marginalis* | 1 |
| *Pseudomonas syringae* (multiple pathovars) | 93 |
| *Pseudomonas fluorescens* A | 4 |
| *Pseudomonas fluorescens* B | 5 |
| *Pseudomonas fluorescens* C (Inc.ATCC 10844) | 12 |
| *Pseudomonas fluorescens* G (Inc.ATCC 13524) | 14 |
| *Pseudomonas coronafaciens* | 3 |
| *Pseudomonas aeruginosa* (Inc.ATCC 15526) | 9 |
| fluorescent pseudomonads (incomplete identification) | 61 |
| *Pseudomonas mendocina* | 1 |
| *Pseudomonas stutzeri* | 1 |
| *Pseudomonas alcaligenes* | 1 |
| *Pseudomonas testosteroni* (Inc.ATCC 17409, 17510, 11996) | 7 |
| *Pseudomonas cepacia* ATCC 10856 | 1 |
| *Pseudomonas delafieldii* ATCC 17505 | 1 |
| *Pseudomonas diminuta* ATCC 11568 | 1 |
| *Pseudomonas acidovorans* | 3 |
| *Pseudomonas cruciuriae* ATCC 13262 | 1 |
| *Pseudomonas methanolica* ATCC 21704 | 1 |
| *Pseudomonas pickettii* ATCC 27511 | 1 |
| *Pseudomonas vesicularis* ATCC 11426 | 1 |
| *Xanthomonas maltophilia* ATCC 13637 | 2 |
| *Agrobacterium tumefaciens* | 3 |
| *Erwinia herbicola* | 1 |
| *Enterobacter cloacae* ATCC 13047 | 1 |
| *Enterobacter aerogenes* ATCC 13048 | 1 |
| *Hafnia alvei* | 2 |
| non-fluorescent (incomplete identification) | 11 |
| *Bacillus thuringiensis* | 1 |
| *Bacillus licheniformis* | 1 |
| *Corynebacterium fascians* | 41 |

```
1    GATATCCCATATCAAGGAGCAGAGTCATGAATCTGAATCGTTTGAACGTTATCCATTGACC
                       MetAsnLeuAsnArgPheGluArgTyrProLeuThr

63   TTCGGTCCTTCTCCCATCACGCCCTTGAAGCGCCTCAGTCAACATCTGGGGGCAAGGTCGA
     PheGlySerProIleThrProLeuLysArgLeuSerGlnHisLeuGlyGlyLysValGl

125  GCTGTATGCCAAACGTGAAGACTGCAACAGTGGCCTGGCCTTTGGTGGGAACAAGACGCGCA
     uLeuTyrAlaLysArgGluAspCysAsnSerGlyLeuAlaPheGlyGlyAsnLysThrArgL

187  AGCTCGAATACCTCATTCCCGAAGCTGCGATCGAGCAAGGCTGCGATACGCTGGTTTCCATCGGC
     ysLeuGluTyrLeuIleProGluAlaIleGluGlnGlyCysAspThrLeuValSerIleGly

249  GGCATCCAGTCCGAACCAGACCCGTCAGGTCAGAACGCAGAACCCGTCGCTGCCCGTCGCTGCCCACTTGGGCATGAAGTG
     GlyIleGlnSerAsnGlnThrArgGlnValAlaAlaAlaAlaHisLeuGlyMetLysCy

311  CGTGTTGGTGCAGGAAAACTGGGTGAACTATTCCGACGCGGTGTATGACCGCGTAGGCAACA
     sValLeuValGlnGluAsnTrpValAsnTyrSerAspAlaValTyrAspArgValGlyAsnI

373  TCGAGATGTCGCGGATCATGGGCGCGCTGATGTGCGGCTTGACGCGCTGGCTTCGATATTGGC
     leGluMetSerArgIleMetGlyAlaLeuMetCysGlyLeuAspAlaAlaGlyPheAspIleGly

435  ATTCGGCCAAGTTGGGAAAAGGCCATGAGCGATGTCGTGGAACAGGGTGGCAAACCGTTTCC
     IleArgProSerTrpGluLysAlaMetSerAspValValGluGlnGlyGlyLysProPhePr

497  GATTCCAGCGGGTTGCTCCGAGCATCCCTATGGCGGCCTCGGTTTCGTCGGCTTTGCCGAAG
     oIleProAlaGlyCysSerGluHisProTyrGlyGlyLeuGlyPheValGlyPheAlaGluG
```

FIG. 2 cont.

```
559  AGGTGGGGCAGGAGGAAAAGGAACTGGGCTTCAAGTTTGACTACATCGTGGTCTGCTCGGTG
     luValArgGlnGlnGluLysGluLeuGlyPheLysPheAspTyrIleValValCysSerVal

621  ACCGGCAGTACGCAGGCGGGGCATGGTGGTTGTTGGTTTCGCGGCTGCGTTCGAAGAATGT
     ThrGlySerThrGlnAlaGlyMetValValGlyPheAlaAlaAspGlyArgSerLysAsnVa

683  GATTGGTATCGATGCTTCGGCCAAGCCGGAACAGACCAAGGCACAGATCCTGCGCATCGCCC
     lIleGlyIleAspAlaSerAlaLysProGluGlnThrLysAlaGlnIleLeuArgIleAlaA

745  GACACACCGCTGAGTTGGTGGTGGGGCGAGATTACGGAAGAGGACGTGGTGCTCGAT
     rgHisThrAlaGluLeuValGluLeuGlyArgGluIleThrGluAspValValLeuAsp

807  ACGCGTTTTGCCTACCCGGAATATGGCTTGCCCAACGAAGGCACATTGGAAGCCATCCGACT
     ThrArgPheAlaTyrProGluTyrGlyLeuProAsnGluGlyThrLeuGluAlaIleArgLe

869  GTGCGGGCAGCCTTGAAGGCGTGACAGACCCGGTATATGAAGGTAAATCGATGCACGGCA
     uCysGlySerLeuGluGlyValThrAspProValTyrGluGlyLysSerMetHisGlyM

931  TGATTGAAATGGTCCGTCGTGGTGAATTCCCGAAGGTTCCAAAGTGCTTTACGCACACTTG
     etIleGluMetValArgArgGlyGluPheProGluGlySerLysValLeuTyrAlaHisLeu

993  GGTGGGGCGCCGGCGCCTGAACGCCTACAGCTTCCTGTTTCGTAACGGCTAAGGCTAGAACTG
     GlyGlyAlaProAlaLeuAsnAlaTyrSerPheLeuPheArgAsnGlyEnd

1055 CTTTGGAGTCATCTGTGGGAGCTC  1079
```

FIG. II

```
  1  CTAGAAGGAA GCTTCACGAA ATCGGCCCTT ATTCAAAAAT AACTTTTAAA
 51  TAATGAATTT TAAATTTTAA GAAATAATAT CCAATGAATA AATGACATGT
101  AGCATTTTAC CTAAATATTT CAACTATTTT AATCCAATAT TAATTTGTTT
151  TATTCCCCAC AATAGAAAGT CTTGTGCAGA CATTTAATCT GACTTTTCCA
201  GTACTAAATA TTAATTTCT GAAGATTTTC GGGTTTAGTC CACAAGTTTT
251  AGTGAGAAGT TTTGCTCAAA ATTTTAGGTG AGAAGGTTTG ATATTTATCT
301  TTTGTTAAAT TAATTTATCT AGGTGACTAT TATTTATTTA AGTAGAAATT
351  CATATCATTA CTTTTGCCAA CTTGTAGTCA TAATAGGAGT AGGTGTATAT
401  GATGAAGGAA TAAACAAGTT CAGTGAAGTG ATTAAAATAA AATATAATTT
451  AGGTGTACAT CAAATAAAAA CCTTAAAGTT TAGAAAGGCA CCGAATAATT
501  TTGCATAGTA GATATTAGTA AATTTATAAA AATAAAAGAA ATGTAGTTGT
551  CAAGTGTGTCT TCTTTTTTTT GGATAAAAAT AGCAGTTGGC TTATGTCATT
```

FIG. 14

```
601   CTTTTACAAC CTCCATGCCA CTTGTCCAAT TGTTGACACT TAACTAATTA
651   GTTTGATTCA TGTATGAATA CTAAATAATT TTTTAGGACT GACTCAAATA
701   TTTTTATATT ATCATAGTAA TATTTATCTA ATTTTTAGGA CCACTTATTA
751   CTAAATAATA AATTAACTAC TACTATATTA TTGTTGTGAA ACAACAACGT
801   TTTGGTTGTT ATGATGAAAC GTACACTATA TCAGTATGAA AAATTCAAAA
851   CGATTAGTAT AAATTATATT GAAAATTTGA TATTTTTCTA TTCTTAATCA
901   GACGTATTGG GTTTCATATT TTAAAAAGGG ACTAAACTTA GAAGAGAAGT
951   TTGTTTGAAA CTACTTTTGT CTCTTTCTTG TTCCCATTTC TCTCTTAGAT
1001  TTCAAAAAGT GAACTACTTT ATCTCTTTCT TTGTTCACAT TTTATTTTAT
1051  TCTATTATAA ATATGGCATC CTCATATTGA GATTTTTAGA AATTATTCTA
1101  ATCATTCACA GTGCAAAAGA AGATCTAAAG CCCTAGAG
```

FIG. 14 cont.

```
ACAGCCGTCCTAAGGAGAAGATAAGATCTATGAAAAAACTGAAACTGCATGGCTTTAATA  60
                          MetLysLysLeuHisGlyPheAsnA

ATCTGACCAAAAGTCTGAGTTTTGTATTACGATATCTGCTACGCCAAAACTGCCGAAG   120
snLeuThrLysSerLeuPheCysIleTyrAspIleCysTyrAlaAlaLysThrAlaGluG

AGCGCGACGGTTATATTGCTTATATCGATGAACTCTATAATGCCAACCGTCTGACCGAAA  180
luArgAspGlyTyrIleAlaTyrIleAspGluLeuTyrAsnAlaAsnArgLeuThrGluI

TCCTGTCAGAAACCTGTTCCATTATCGGGGCTAATATTCTTAACATCGCCGCCAGGATT   240
leLeuSerGluThrCysSerIleIleGlyAlaAsnIleLeuAsnIleAlaArgGlnAspT

ACGAACCACAGGGTGCCAGCGTCACTATTCTGGTGAGTGAAGAACCGGTTGACCCGAAAC  300
yrGluProGlnGlyAlaSerValThrIleLeuValSerGluGluProValAspProLysL

TCATCGACAAAACAGAACACCCCGGCCCAGAAACGTCGTTGCCCATCTTGATA        360
euIleAspLysThrGluHisProGlyProLeuProGluThrValValAlaHisLeuAspL

AAAGTCATATTTGCTACATACCTACCCGGAAAGTCATCCTGAAGGCGGTTTATGTACCT   420
ysSerHisIleCysValHisThrTyrProGluSerHisProGluGlyGlyLeuCysThrP
```

FIG. 15

```
TCCGCGCCGATATTGAAGTCTCTCTACCTGCGGGCTGTGATTTCTCCGCTGAAGGCGCTGAATT  480
heArgAlaAspIleGluValSerLeuTyrCysGlyValIleSerProLeuLysAlaLeuAsnT

ACCTGATCCACCAGCTTGAGTCCGATATCGTAACCATTGATTATCGCGTGCGGTTTA  540
yrLeuIleHisGlnLeuGluSerAspIleValThrIleAspTyrArgValArgGlyPheT

CCCGGCACATTAACGGTATGAAGCACTTTATCGACCATGAGATTAATTCGATTCAGAACT  600
hrArgAspIleAsnGlyMetLysHisPheIleAspHisGluIleAsnSerIleGlnAsnP

TTATGTCTGACGATATGAAGGCGCTGTATGACATGGTGAACGTCTATCAGAAA  660
heMetSerAspAspMetLysAlaLeuTyrAspMetValAsnValTyrGlnGluA

ATATCTTCCATACCAAGATGTTGCTTAAAGAGTTCGACCTTAAGCACTACATGTTCCACA  720
snIlePheHisThrLysMetLeuLeuLysGluPheAspLeuLysHisTyrMetPheHisT

CCAAACCGGAAGACTTAACCGACAGCGAGCGCCAGGAAATTACCGCTGCTGGAAAG  780
hrLysProGluAspLeuThrAspSerGluArgGlnGluIleThrAlaAlaLeuTrpLysG

AAATGCGCGAGATTATTACGGGCGCAATATGCCAGCTGTTTAACGGCTCTGGCGAGCT  840
luMetArgGluIleIleTyrTyrGlyArgAsnMetProAlaVal*

CCCAGGCTCCGCCAGATCTATTACTTCTGCTGCACGAAATTGCGGTAAGCCGCCACGAC  900
```

FIG. 15 cont.

```
CCAAACACATAATACTTTAATACAATTAGTTATTTATTAGAAGTATTAAAGTAAAGCA                                              60

CTTGTGAGTTGTGTACATTTTATTAATCTTCATCTTCTTAATTCTCTTCAGTTTTTAATT                                           120

TCTTCACTTCCTAAACTCATTAGTAAAAAAAAAATGGATTTGAAAGACCAAC                                                   180
                                  MetGlyPheGluIleAlaLysThrAsn

TCAATCTTATCAAAATTGGCTACTAATGAAGAGCATGGCGAAAACTCGCCATATTTGAT                                            240
SerIleLeuSerLysLeuAlaThrAsnGluGluHisGlyGluAsnSerProTyrPheAsp

GGGTGGAAAGCATACGATAGTGATCCTTTCCACCCTCTAAAAACCCAACGGAGTTATC                                             300
GlyTrpLysAlaTyrAspSerAspProPheHisProLeuLysAsnProAsnGlyValIle

CAAATGGGTCTTGCTGAAAATCAGCTTTGTTTAGACTTGATAGAAGATTGGATTAAGAGA                                           360
GlnMetGlyLeuAlaGluAsnGlnLeuCysLeuAspLeuIleGluAspTrpIleLysArg

AACCCAAAGGTTCAATTTGTTCTGAAGGAATCAAATCATTCAAGGCCATTGCCAACTTT                                            420
AsnProLysGlySerIleCysSerGluGlyIleIleLysSerPheLysAlaIleAlaAsnPhe

CAAGATTATCATGGCTTGCCTGAATTCAGAAAAGCGATTGCAAATTTATGGAGAAAACA                                            480
GlnAspTyrHisGlyLeuProGluPheArgLysAlaIleAlaLysPheMetGluLysThr

AGAGGAGGAAGTTAGATTTGATCCAGAAAGAGTTGTTATGGCTGGTGCCACTGGA                                                540
ArgGlyGlyArgValArgPheAspProGluArgValValMetAlaGlyGlyAlaThrGly
```

FIG. 16A

```
GCTAATGAGACAATTATATATTTGTTTGGCTGATCCTGGGATGCATTTTTAGTACCTTCA    600
AlaAsnGluThrIleIlePheCysLeuAlaAspProGlyAspAlaPheLeuValProSer

CCATACTACCCAGCATTTAACAGAGATTTAAGATGGAGAACTGGAGTACAACTTATTCCA    660
ProTyrTyrProAlaPheAsnArgAspLeuArgTrpArgThrGlyValGlnLeuIlePro

ATTCACTGTGAGAGCTCCAATAATTTCAAAATTACTTCAAAGCAGTAAAAGAAGCATAT    720
IleHisCysGluSerSerAsnAsnPheLysIleThrSerLysAlaValLysGluAlaTyr

GAAAATGCACAAAATCAAACATCAAAGTAAAAGGTTTGATTTGACCAATCCATCAAAT    780
GluAsnAlaGlnAsnGlnThrSerLysValLysGlyLeuIleLeuThrAsnProSerAsn

CCATTGGGCACCACTTTGGACAAAGACACACTGAAAAGTGTCTTGAGTTTCACCAACCAA    840
ProLeuGlyThrThrLeuAspLysAspThrLeuLysSerValLeuSerPheThrAsnGln

CACAACATCCACCTTGTTTGTGACGAAATCTACGCAGCCACTGTCTTTGACACGCCCTCAA    900
HisAsnIleHisLeuValCysAspGluIleTyrAlaAlaThrValPheAspThrProGln

TTCGTCAGTATAGCTGAAATCCTCGATGAACAGGAAATGACTTACTGCAACAAAGATTTA    960
PheValS   IleAlaGluIleLeuAspGluGlnGluMetThrTyrCysAsnLysAspLeu

GTTCACATCGTCTACAGTCTTTCAAAAGACATGGGGTTACCAGGATTAGAGTCGGAATC    1020
ValHisIleValTyrSerLeuSerLysAspMetGlyLeuProGlyLeuArgValGlyIle
```

FIG. 16B

```
ATATATTCTTTTAAGGACGATGTCGTTAATTGTGCTAGAAAAATGTCGAGTTTCGGTTTA    1080
IleTyrSerPheAsnAspValValAsnCysAlaArgLysMetSerSerPheGlyLeu

GTATCTACACAAACGCAATATTTTTAGCGGCAATGCCATCGGACGAAAAATTCGTCGAT    1140
ValSerThrGlnThrGlnTyrPheLeuAlaAlaMetProSerAspGluLysPheValAsp

AATTTCTAAGAGAAAGCGCGATGAGGTTAGGTAAAAGCCACAAACATTTACTAATGGA     1200
AsnPheLeuArgGluSerAlaMetArgLeuGlyLysArgHisLysHisPheThrAsnGly

CTTGAAGTAGTGGGAATTAAATGCTTGAAAAATAATGCGGGGCTTTTTTGTTGGATGGAT   1260
LeuGluValValGlyIleLysCysLeuLysAsnAsnAlaGlyLeuPheCysTrpMetAsp

TTGCGTCCACTTTTAAGGGAATCGACTTTCGATAGCGAAATGTCGTTATGGAGAGTTATT   1320
LeuArgProLeuLeuArgGluSerThrPheAspSerGluMetSerLeuTrpArgValIle

ATAAACGATGTTAAGCTTAACGTCTCGCTTGGATCTTCGTTTGAATGTCAAGAGCCAGGG   1380
IleAsnAspValLysSerPheGluCysGlnGluProGly

TGGTTCCGAGTTTGTTTTGCAAATATGGATGATGAACGGTTGATATTGGCGCTCGCGAGG   1440
TrpPheArgValCysPheAlaAsnMetAspGlyThrValAspIleAlaLeuAlaArg
```

FIG. 16C

```
ATTCGGAGGTTCGTAGGTGTTGAGAAAAGTGGAGATAAATCGAGTTCGATGGAAAAGAAG    1500
IleArgArgPheValGlyValGluLysSerGlyAspLysSerSerMetGluLysLys

CAACAATGAAGAAGAATAATTTGAGACTTAGTTTTCGAAAAGAATGTATGATGAAAGT      1560
GlnGlnTrpLysLysAsnAsnLeuArgLeuSerPheSerLysArgMetTyrAspGluSer

GTTTTGTCACCACTTTCGTCACCTATTCCCTCCCCTCACCATTAGTTCGTTAAGACTTAATT  1620
ValLeuSerProLeuSerSerProIleProProSerProLeuValArg*

AAAAGGGAAGAATTTAATTTATGTTTTTTATATTTGAAAAAAATTGTAAGAATAAGA       1680

TTATAATAGGAAAAGAAAAGAAAATAAGTATGAGGAGTATTTCAGAAATAGTTGTTA       1740

GCGTATGTATTGACAACTGGTCTATGTACTTAGACATCATAATTTGTCTTAGCTAATTAA    1800

TGAATGCAAAAGTGAAGTT
```

FIG. 16D

```
GGATCC ATG AAT TTG AAT CGT TTT AAA CGT TAT CCG TTG ACC TTC GGT        48
       Met Asn Leu Asn Arg Phe Lys Arg Tyr Pro Leu Thr Phe Gly
CCT TCT CCC ATC ACG CCC TTG AAG CGC CTC AGT GAA CAC TTG GGT GGC        96
Pro Ser Pro Ile Thr Pro Leu Lys Arg Leu Ser Glu His Leu Gly Gly
AAG GTC GAG CTG TAT GCC AAG CGT GAA GAC TGC AAC AGT GGC CTG GCC       144
Lys Val Glu Leu Tyr Ala Lys Arg Glu Asp Cys Asn Ser Gly Leu Ala
TTC GGC GGG AAC ACG CGC AAG CGC GAA CTC GAA TAT TTG CCC GAA GCG       192
Phe Gly Gly Asn Thr Arg Lys Arg Glu Leu Glu Tyr Leu Pro Glu Ala
CTC GAG CAA GGC TGC GAT ACC TTG GTT TCC ATC GGC ATC CAG TCG           240
Leu Glu Gln Gly Cys Asp Thr Leu Val Ser Ile Gly Ile Gln Ser
AAC CAG ACC CGC CAG GTG GCC GTT GCC GCT CAC CTG GGC ATG AAG           288
Asn Gln Thr Arg Gln Val Ala Ala Ala His Leu Gly Met Lys
TGC GTG CTG CAG GAA AAC TGG GTG AAC TAC GAT GCG GTG TAT               336
Cys Val Leu Gln Glu Asn Trp Val Asn Tyr Asp Ala Val Tyr
GAC CGC GTT GGC AAT ATC GAA ATG TCT CGC ATG GCC GAG GTA               384
Asp Arg Val Gly Asn Ile Glu Met Ser Arg Met Ala Glu Val
CGA CTG GAC GCC GGG TTC GAT ATC ATT CGG CCC AGC TGG GAG               432
Arg Leu Asp Ala Gly Phe Asp Ile Ile Arg Pro Ser Trp Glu
AAG GCC ATG GAC GTG GTG GCG GGT AAG CCG TTC CCG ATA                   480
Lys Ala Met Asp Val Val Ala Gly Lys Pro Phe Pro Ile
CCG GCG CGC GTT TCC GAA CAC CCC TAC GGC CTT GGG TTC GTC GGC           528
Pro Ala Gly Cys Ser Glu His Pro Tyr Gly Leu Gly Phe Val Gly
```

FIG. 17

```
TTT GCC GAG GAA GTG CGA GAG CAG GAA AAA CAA CTG GGG TTC ACG TTC    576
Phe Ala Glu Glu Val Arg Glu Gln Glu Lys Gln Leu Gly Phe Thr Phe

GAC TAC ATC GTG GTC TGC TCT GTG ACC GTG CTG AAG AGT GCC GGC ATG    624
Asp Tyr Ile Val Val Cys Ser Val Thr Val Leu Lys Ser Ala Gly Met

GTC GTC GGT TTC GCC GCG GCG GAC CGT TCG AAG AAC GTT ATC GGC ATT    672
Val Val Gly Phe Ala Ala Ala Asp Arg Ser Lys Asn Val Ile Gly Ile

GAT GCC TCG GCC AAG CCG GAG CAA ACC AAG GCA CAG ATC CTG CGT ATC    720
Asp Ala Ser Ala Lys Pro Glu Gln Thr Lys Ala Gln Ile Leu Arg Ile

GCC CGG CAC ACC GCA GAG TTG GTG GAA CTG GGC CGT GAG ATC ACC GAA    768
Ala Arg His Thr Ala Glu Leu Val Glu Leu Gly Arg Glu Ile Thr Glu

GAC GAC GTG GTG CTC GAT ACA CGT TTT GCC TAC CCG GAA TAC GGT TTG    816
Asp Asp Val Val Leu Asp Thr Arg Phe Ala Tyr Pro Glu Tyr Gly Leu

GAT GTT CTG ACG CTG GAA GCC ATT CGT TTG TGC AGC CTG GGG AGC CTG GAA    864
Asp Val Leu Thr Leu Asp Thr Arg Phe Ala Ile Arg Leu Cys Ser Leu Glu

CCC AAC GAA GGC ACG CTG GAA GCC CTG GAA ATC GAG GGC AAA TCC ATG GGG ATG    912
Pro Asn Glu Gly Thr Leu Glu Ala Ile Arg Leu Cys Gly Ser Leu Glu Gly Met

GGT GTG ACC GAT CCG GTG TAC CGG GAG TTC CCC GAA GGC TCC AAA GTG CTG    960
Gly Val Thr Asp Pro Val Tyr Arg Glu Phe Pro Glu Gly Ser Lys Val Leu

ATT GAA ATG GTC GTC CGC CGT GGC GGC GAG TTC CCC GGG GAA TAC AGC TTC CTG   1008
Ile Glu Met Val Val Arg Arg Gly Gly Glu Phe Pro Gly Glu Tyr Ser Phe Leu

TAT GCG CAC TTG GGT CCT GCG AAT GCC TAC TCC AGC TTC CTG
Tyr Ala His Leu Gly Pro Ala Asn Ala Tyr Ser Phe Leu

TTT CGT AAC GGC GGATCCGGG                                          1029
Phe Arg Asn Gly
```

FIG. 17 cont.

```
AGATCTATCGATAAGCTTGATGTAATTGGAGGAAGATCAAAATTTCAAT    50
CCCCATTCTTCGATTGCTTCAATTGAAGTTTCTCCGATGGCCAAGTTAG   100
CAGAATCTGCAATGGTGTGCAGAACCCATCTCTTATCTCTCCAATCTCGA  150
AATCCAGTCAACGCAAATCTCCCTTATCGGTTTCTCTGAAGACGCAGCAG  200
CATCCCACGAGCTTATCCGATTTCGTCGTGGGGATTGAAGAAGAGTGG    250
GATGACGTTAATTGGCTCTGAGCTTCGTCCCTCTTAAGGTCATGTCTTCTG 300
TTTCCACGGGCGTGCATGC                                 318
```

```
GCATGCTTCACGGTGCAAGCAGCCGTCCAGCAACTGCTCGTAAGTCCCTCT    50
GGTCTTTCTGGAACCGTCCGTATTCCAGGTGACAAGTCTATCTCCCACAG    100
GTCCTTCATGTTTGGAGGTCTCGCTAGCGGTGAAACTCGTATCACCGGTC    150
TTTTGGAAGGTGAAGATGTTATCAACACTGGTAAGGCTATGCAAGCTATG    200
GGTGCCAGAATCCGTAAGGAAGGTGATACTTGGATCATTGATGGTGTTGG    250
TAACGGTGGACTCCTTGCTCCCTGAGGCTCCTCTCGATTTCGGTAACGCTG    300
CAACTGGTTGCCGTTTGACTATGGGTCTTGTTGGTGTTTACGATTTCGAT    350
AGCACTTTCATTGGTGACGCTTCTCTCACTAAGCGTCCAATGGGTCGTGT    400
GTTGAACCCACTTCGCGAAATGGGTGTGCAGGTGAAGTCTGAAGACGGTG    450
ATCGTCTTCCAGTTACCTTGCGTGGACCAAAGACTCCAAGTCCGCTTGC    500
TACAGGGTACCTATGGCTTCCGCTCAAGTGAAGTCCGCTGTTATCGAGCCAC    550
TGGTCTCAACACCCCAGGTATCACCACTGTTATCGAGCCAATCATGACTC    600
GTGACCACACTGAAAAGATGCTTCAAGGTTTTGGTGCTAACCTTACCGTT    650
GAGACTGATGCTGACGGTGTGCCGTACCATCCGTCTTGAAGGTCGTGGTAA    700
```

FIG. 21 cont.

```
GCTCACCGGTCAAGTGATTGATGTTCCAGGTGATCCATCCTCTACTGCTT    750
TCCCATTGGTTGCTGCCTTGTTCCAGTTCCGACGTCACCATCCTT         800
AACGTTTTGATGAACCCAACCTGGTCTCCATCTTTGACTCTGCAGGA       850
AATGGGTGCCGACATCGAAGTGATCAACCCACGTCTTGCTGGTGGAGAAG    900
ACGTGGCTGACTTGCGTGTTCGTGTTCTTCTACTTTGAAGGGTGTTACTGTT  950
CCAGAAGACCGTGCTCCTTCTATGATCGACGAGTATCCAATTCTCGCTGT    1000
TGCAGCTGCATTCGCTGAAGGTGCTACCGTTATGAACGGTTTGGAAGAAC    1050
TCCGTGTTAAGGAAAGCGACCGTCTTTCTGCTGTCGCAAACGGTCTCAAG    1100
CTCAACGGTGTTGATTGCGATGAAGGTGAGACTTCTCCGTCGTCGCGTGG    1150
TCGTCCTGACGGTAAGGGTCTCCGGTAACGCTTCTGGAGCAGCTGTCGCTA   1200
CCCACCTCGATCACCGTATCGCTATGAGCTTCCCTCGTTATGGGTCTCGTT   1250
TCTGAAACCCTGTTACTGTTGATGATGCTACTAGATCGCTACTAGCTT      1300
CCCAGAGTTCATGGATTTGATGGCTGGTCTTGGAGCTAAGATCGAACTCT    1350
CCGACACTAAGGCTGCTTGATGAGCTC                           1377
```

FIG. 22

```
TCATCAAAATATTTAGCAGCATTCCAGATTGGGTTCAATCAACAAGGTAC    50
GAGCCATATCACTTTATTCAAATTGGTATCGCCAAAACCAAGAAGGAACT   100
CCCATCCCTCAAAGGTTTGTAAGGAAGAATTCTCAGTCCAAAGCCCTCAACA 150
AGGTCAGGGTACAGAGTCTCCAAACCATTAGCCAAAAGCTACAGGAGATC   200
AATGAAGAATCTTCAATCAAAGTAAACTACTGTTCCAGCACATGCATCAT   250
GGTCAGTAAGTTTCAGAAAAGACATCCACCGAAGACTTAAAGTTAGTGG    300
GCATCTTTGAAAGTAATCTTGTCAACATCGAGCAGCTGGCTTGTGGGAC    350
CAGACAAAAAAGGAATGGTGCAGAATTGTTAGGCGCACCTACCAAAAGCA   400
TCTTTGCCTTTATTGCAAAGATAAAGCAGATTCCTCTAGTACAAGTGGGG   450
AACAAAATAACGTGGAAAAGAGCTGTCCTGACAGCCCACTCACTAATGCG   500
TATGACGAACGGCAGTGACGACCACAAAAGAATTCCCTCTATATAAGAAGG  550
CATTCATTCCCATTGAAGGATCATCAGATACTAACCAATATTTCTC       596
```

CONTROL OF FRUIT RIPENING AND SENESCENCE IN PLANTS

This application is a Continuation of U.S. Ser. No. 07/809,457 filed Dec. 17, 1991, now U.S. Pat. No. 5,512,466 which is a Continuation-In-Part of U.S. Ser. No. 07/632,440 filed Dec. 26, 1990, now abandoned.

FIELD OF THE INVENTION

This invention relates in general to plant molecular biology and more particularly to a method for controlling the ripening of fruit and vegetables as well as controlling the effects of senescence in plants and recombinant DNA molecules capable of affecting the desired control.

BACKGROUND OF THE INVENTION

One of the major problems facing the fruit, vegetable and cut flower industry is the loss of a considerable amount of goods due to spoilage. It is estimated that 12 to 20 percent of the fruit and vegetable products become spoiled from the time they leave the farm until they get to the retail or processing outlets. In the cut flower industry, senescence (the wilting or dying) of the flower before it can be effectively marketed is a significant problem. The spoiling or senescence process observed in fruits, vegetables and cut flowers results in a number of undesirable problems. Chief among these problems is the short harvesting season for the goods and the short shelf life of the goods following the harvest. Furthermore, these spoilage losses ultimately result in a higher cost of the goods to the consumer.

A primary cause of the spoilage of fruits and vegetables is the natural ripening process of the fruit or vegetable. As the fruit or vegetable becomes more ripe it becomes softer and more easily bruised and susceptible to disease or other spoilage causing agents. It is known that ethylene production in the plant stimulates the fruit ripening process and is the key component in the ripening of fruits and vegetables. Others have attempted to control the ripening of fruits and vegetables in an attempt to extend the shelf life and/or harvesting season of the goods. Many of these attempts have been topical applications of chemicals to the fruit or vegetable itself. These chemical solutions have involved direct applications to the plant in the field or post-harvest applications to the fruit or vegetable itself. Several of these methods are discussed in U.S. Pat. No. 4,957,757 or U.S. Pat. No. 4,851,035. Due to the increasing importance of reducing additional stresses on the environment, a non-chemical means for controlling ripening would be advantageous and beneficial to the industry.

More recently, researchers have used a molecular biology approach to block ethylene synthesis in plants in an attempt to control the ripening of tomatoes. This approach involved transforming a tomato plant with an antisense gene that inhibited the synthesis of ethylene. The antisense gene produces (−) strand RNA that lowers the steady state levels of the (+) strand mRNA encoding a polypeptide involved in the conversion of 1-aminocyclopropane-1-carboxylic acid (ACC) to ethylene by the ethylene forming enzyme ACC oxidase. (Hamilton et al. 1990) While this method exhibits some degree of utility, it would be neither easy nor efficient to apply this technology to other plants, because the antisense gene would probably be species and gene specific which would entail obtaining a different antisense gene for each species of plant desired to be transformed.

Thus a need exists in the fruit, vegetable and cut flower industries for a non-chemical method of controlling fruit ripening and senescence in plants that can easily and efficiently be utilized across a wide variety of plant species.

SUMMARY OF THE INVENTION

A method for controlling the ripening of fruits and vegetables as well as a method for controlling senescence in cut flowers is presented. In general, the method involves expressing an ACC metabolizing enzyme in the desired plant tissue which lowers the level of ACC in the tissue which thereby reduces the level of ethylene in the desired plant tissue. More particularly, the method comprises transforming plant cells with a chimeric gene comprising a promoter that functions in plant cells to cause the production of an RNA sequence, a structural DNA sequence that causes the production of an RNA sequence that encodes an ACC deaminase enzyme and a 3' non-translated region that functions in plant cells to cause the addition of a stretch of polyadenyl nucleotides to the 3' end of the RNA sequence, with the promoter being heterologous with respect to the structural coding sequence, and then growing the plant to maturity. The expression of the ACC deaminase in the fruit delays the ripening process which provides an extended harvesting season and an extended shelf life for the goods. Likewise, expression of an ACC metabolizing enzyme in floral species suitable for use in the cut flower industry delays senescence of the flowers, thus extending the shelf life and marketability of the flowers.

In another aspect of the present invention, a recombinant, double stranded DNA molecule comprising a promoter that functions in plant cells to cause the production of an RNA sequence, a structural DNA sequence that encodes an ACC deaminase enzyme and a 3' non-translated region that functions in plant cells to cause the addition of a stretch of polyadenyl nucleotides to the 3' end of the RNA sequence, where the promoter is heterologous with respect to the structural DNA sequence, is also provided that enables one to obtain plants capable of expressing ACC deaminase in order to control ripening and senescence. The expression of the ACC deaminase in the plant cells extends the harvesting season and the shelf life of the goods by reducing the production of ethylene in the plants.

Among the many aims and objects of the present invention, one primary object is to provide a method of controlling ripening and senescence in plants utilizing a molecular biology technique that is efficiently and broadly applicable to many plant species.

Another object of the present invention is to provide a method for extending the harvesting season and shelf life of fruits, vegetables and flowers by controlling the production of ethylene in the plant by lowering the steady state levels of ACC using an ACC metabolizing enzyme, such as ACC deaminase or ACC malonyl transferase, expressed in the plant.

It is a further object of the present invention to reduce the synthesis of ethylene in plants by expressing the enzyme ACC deaminase in the plant.

It is still another object of the present invention to extend the market life of cut flowers by expressing the enzyme ACC deaminase in the flower thereby reducing the senescence effects of ethylene synthesis in the flower.

It is a still further object of the present invention to provide transformed plants expressing an enzyme, ACC deaminase, in the plant so as to delay ripening of the fruit of the plant whether the fruit is allowed to ripen on the vine or if picked at an unripe stage of development to be ripened at a later time.

It is also a primary aim of the present invention to provide a fruit-bearing plant capable of expressing ACC deaminase specifically in the fruit of the plant.

Other and further objectives and aims of the invention will be made clear or become apparent from the following description and claims when read in light of the accompanying drawings.

BRIEF DESCRIPTION OF THE DRAWINGS

FIG. 1 illustrates the contents of the bacterial collection used to screen for ACC deaminase.

FIG. 2 shows the nucleotide sequence of the ACC deaminase gene from *Pseudomonas chloroaphis* (isolate 6G5) (SEQ ID NO:1).

FIG. 14 illustrates the nucleotide sequence of the fruit specific promoter E8 with the 5' HindIII and 3'BglII restriction sites underlined (SEQ ID NO:10).

FIG. 15 illustrates the nucleotide sequence of the S-adenosyl methionine (SAM) decarboxylase gene (SEQ ID NO:9).

FIG. 16(A–D) illustrates the nucleotide sequence of the ACC synthase gene (SEQ ID NO:8).

FIG. 17 illustrates the nucleotide sequence of the ACC deaminase gene isolated from isolate 3F2. (SEQ ID NO:15)

FIG. 20 illustrates the DNA sequence of the chloroplast transit peptide CTP2. (SEQ ID NO:13)

FIG. 21 illustrates the DNA sequence of the CP4 synthetic 5-enolpyruvyl-3-shikimate phosphate synthase (EPSPS) gene. (SEQ ID NO:14)

FIG. 22 illustrates the DNA sequence of a full-length transcript promoter from figwort mosaic virus (SEQ ID NO: 17).

DETAILED DESCRIPTION OF THE PREFERRED EMBODIMENTS

Figure 3:
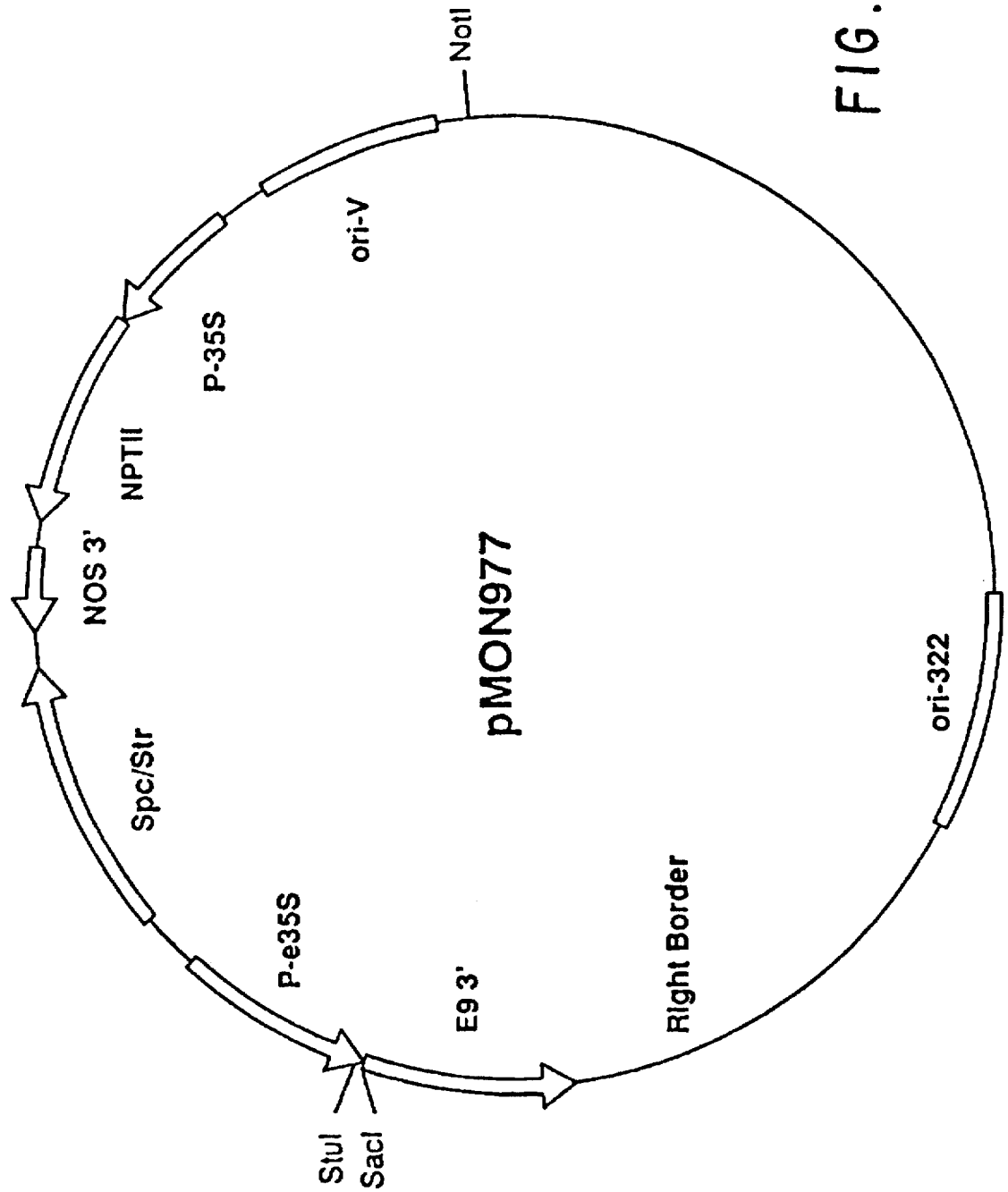
FIG. 3 illustrates a plasmid map of pMON977.

The metabolic pathway for the production of ethylene in plants is as follows:

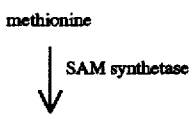

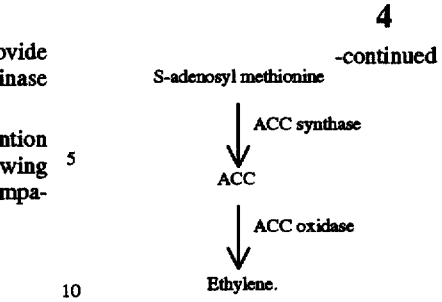

In order to inhibit the biosynthesis of ethylene in plant tissues, one possible method would be to metabolize 1-aminocyclopropane-1-carboxylic acid (hereinafter ACC) and remove it from the metabolic pool. While it was unknown whether any ACC metabolizing enzyme would be capable of reducing the level of ACC sufficient to inhibit ethylene biosynthesis, this approach was investigated. A number of enzymes are capable of metabolizing ACC. Examples of ACC metabolizing enzymes are ACC deaminase and ACC malonyl transferase. The ACC deaminase enzyme metabolizes ACC by converting it to $\alpha$-ketobutyrate and ammonia. Thus, if the enzyme ACC deaminase, or another ACC metabolizing enzyme, having sufficient kinetic capabilities can be expressed at sufficient levels in the plant, the synthesis of ethylene would be inhibited by the removal of ACC from the metabolic pool in the tissues where the ACC metabolizing enzyme is being expressed. A significant aspect of the present invention is to provide a mechanism for delaying the ripening of fruit or senescence in plants by reducing the steady state levels of ACC in the plant tissues which reduces the level of ethylene in the plant tissues. It is preferred that the steady state concentrations of ethylene or ACC in the plant be reduced by at least about 70% from normal levels in a non-modified cultivar. Preferably, the ethylene or ACC concentrations are reduced by at least about 90% from normal levels. It is believed that the reduction of the steady state levels of ACC or ethylene in a plant or the fruit of a plant can be achieved by various methods, all of which are considered within the scope of the instant invention.

Regarding the delaying of ripening of fruit, it is preferred that the fruit be delayed from ripening on the vine by 1 to 30 days. This delay is to be measured from the onset of ripening and, specifically with respect to tomato, from when the fruit reaches the breaker stage of ripening. Likewise, the fruit is preferably delayed in ripening from 1 to 90 days following detachment from the vine and more preferably between 5 and 30 days. With respect to tomato, this delay in ripening is measured from the time of detachment of the fruit from the vine when the fruit is removed at the mature green or breaker stage of ripening. It is to be understood that the delay in ripening after detachment from the vine can be extended beyond the terms described by cold storage or other methods known in the art.

The enzyme ACC deaminase was chosen for further experimentation. ACC deaminase is not known in the art to be produced or expressed naturally in plants. Therefore, in order to pursue a method of inhibiting ethylene synthesis in plants by degrading ACC, an ACC deaminase encoding gene must be identified and then be made capable of being expressed in plants.

ACC deaminase is known to be expressed in certain microorganisms (Honma, M. and Shimomura, T. 1978). In order to isolate an ACC deaminase enzyme, a bacterial screen to isolate bacteria expressing the enzyme can be designed to identify such a bacteria or microorganism. Other methods for identifying an ACC deaminase enzyme, such as screening strains of yeast or fungi, would be equally applicable and routine to one of skill in the art. The following is a description of a bacterial screen that identified bacteria expressing an ACC deaminase enzyme.

A collection of bacterial strains (Drahos, D. 1988) was screened for organisms that are capable of degrading ACC. This bacterial collection was composed of 597 microorganisms. The majority of the organisms were fluorescent Pseudomonas species with the remaining being microbes typically found in the soil. A description of the bacterial collection is found in FIG. 1. The screen was designed to select for microorganisms that would grow in a minimal medium containing ACC at 3.0 mM as the sole source of nitrogen. A sample of each bacteria in the bacterial collection was grown individually in 96-well microliter dishes at 30° C. for four days. Each well contained 0.2 ml of DF medium supplemented with ACC. DF medium was made by combining in 1 liter of autoclaved water, 1 ml each of Reagent A, Reagent B, Reagent C and 5 mg of thiamine HCl. Reagent A is made up of 1 mg $H_3BO_3$, 1 mg $MnSO_4.7H_2O$, 12.5 mg $ZnSO_4.7H_2O$, 8 mg $CuSO_4.5H_2O$ and 1.7 mg $NaMoO_3.3H_2O$ in 100 mls of autoclaved water. Reagent B is made up of 0.1 g $FeSO_4.7H_2O$ in 100 mls of autoclaved water. Reagent C contains 20 g of $MgSO_4.7H_2O$ in 100 mls of autoclaved water. To the combined solution, carbon sources glucose, gluconate and citrate are added to final concentrations of 0.1% (w/v) each, inorganic phosphate is added to a final concentration of 1.0 mM (w/v) and ACC is added as the sole nitrogen source to a 3.0 mM (w/v) final concentration. Finally, Yeast Extract (DIFCO) is added to a final concentration of 0.01% (w/v).

Based on this screen, three organisms were identified as being capable of growing on ACC-containing medium. Their ability to grow on ACC-containing minimal medium was confirmed by regrowth in 300 ml liquid cultures of the same medium. The two isolates that grew best on ACC were chosen for further characterization. These two isolates were designated 3F2 and 6G5. Both of these organisms were determined to be Pseudomonads as was the organism not chosen for further characterization. Both of the selected organisms were screened for ACC deaminase enzyme activity by an in vitro assay described below. The 6G5 isolate was chosen for further experimentation. The 6G5 bacterium was identified as a *Pseudomonas chloroaphis* strain by gas chromatography analysis of fatty acid methyl esters as described in Miller (1982). From the above screen results, it is apparent that other bacterial strains could be identified which degrade ACC by performing more extensive screens. Thus, other ACC deaminases and those identified in the screen but not utilized for further experimentation are considered to be within the scope of the present invention.

A number of novel organisms capable of degrading ACC have also been isolated from diverse soil samples. These organisms were isolated on the basis of being able to grow on minimal medium with ACC as the sole nitrogen source. Soil samples were collected from St. Charles (Mo., U.S.A.), Sarawak (Malaysia), Iquitos (Peru), San Juan (Puerto Rico) and Mujindi (Tanzania). One gram of each soil sample was suspended into 99 ml of a Dilution buffer bottle (Fisher), shaken well and the soil suspension was diluted 1:100 before plating. Final dilution of the soil samples was $10^{-4}$. One hundred (100) microliters of the diluted sample was spread on the isolation media in petri-plates (100×15 mM) With a hockey-stick glass rod. The isolation media contains a minimal salt base With $K_2HPO_4$ (10 g/L), $MgSO_4.7H_2O$ (5 g/L), and trace metals: $FeSO_4$ (1 mg/L), $MnCl_2$ (1 mg/L), $CUSO_4$ (1 mg/L), $ZnSO_4$ (1 mg/L), $CaCl_2$ (1 mg/L). The pH of the base was adjusted to 7.0, before autoclaving, With 1N HCl. Noble agar (Difco) was used as the solidifying agent (1.5%). Any of the folloWing three media may be used for isolation of ACC degrading microorganisms; (1) base+glucose (5 g/L)+ACC (0.1 to 1.0 g/L); (2) base+$NH_4NO_3$ (5 g/L)+ACC (1 g/L); (3) base+ACC (0.1 to 1.0 g/L). ACC, glucose, $NH_4NO_3$ were dissolved in distilled water, filter-sterilized and added into the autoclaved base media cooling at 50° C. Plates were incubated at 30° C. for 1 week.

ACC was added to some of the soil samples obtained from St. Charles to enrich for ACC degrading bacteria in the soil. In these experiments, ACC (250 mg) was added into 50 ml of dilution buffer containing 0.5 g of St. Charles soil in a 250 ml Erlenmeyer flask. The flask was incubated on a rotary shaker (250 rpm, 30° C.) for 3 days. The ACC enriched sample was then plated as previously described for non-enriched samples. Bacterial colonies capable of growth in the presence of ACC on plates were then isolated into pure cultures and grown in test tubes (20×150 mm) containing 5 ml of the following medium: $KH_2PO_4$ (4 g/L), $K_2HPO_4$ (6.5 g/L), $MgSO_4.7H_2O$ (1 g/L), trace metals (same as isolation media), and ACC (0.3 g/L). Glucose (2 g/L) may be added to assist the growth of the bacteria. Bacterial strains which grew in the minimal salt medium With ACC as the sole carbon and nitrogen sources are listed in Table I.

TABLE I

| Strain | Line # | Source |
| --- | --- | --- |
| 388 | B27444 | St. Charles (ACC enriched) |
| 391 | B27447 | Malaysia |
| 392 | B27448 | Peru |
| 393 | B27449 | St. Charles |
| 401 | B27457 | St. Charles (ACC enriched) |
| T44 | B27817 | Tanzania |
| PR-1 | B27813 | Puerto Rico |

All of these organisms were shown to express ACC deaminase by two criteria. The first was that extracts from all of the organisms were capable of converting ACC to α-ketobutyric acid and the second was that all contained a protein of approximately 37,000 daltons that strongly cross-reacted with an antibody raised against the 6G5 ACC deaminase protein. To further demonstrate the equivalence of these organisms, kinetic parameters were determined for each of the isolated ACC deaminase enzymes.

The $K_m$ for the ACC deaminases isolated from the various soil sources was determined using crude, desalted extracts. Individual strains of bacteria were grown in liquid media containing 4 g $KH_2PO_4$, 6.5 g $K_2HPO_4$, 1 g $MgSO_4.7H_2O$, 2 g glucose, 1 mg $FeSO_4$, 1 mg $MnCl_2$, 1 mg ZnSO4, 1 mg $CuSO_4$, 1 mg $CaCl_2$, and 300 mg ACC, all in 1 liter $H_2O$. Cells were grown for 2 to 3 days at 30° C. Cells were pelleted by centrifugation and resuspended in extraction buffer containing 0.1M phosphate, pH 7.5, 1 mM EDTA, 0.1% β-mercaptoethanol. The coils were broken with a French Press, 1000 psi, and the cell debris was pelleted by centrifugation. The supernatants were desalted on Sephadex G-25 columns pre-equilibrated with extraction buffer, which resulted in a crude, desalted extract. Glycerol was added to the extract (20% v/v) and enzyme solutions were stored at −20° C. ACC deaminase enzyme assays were conducted as described in the Examples to follow. The assay mixture contained 100 μl of 0.2M Tris buffer, pH 8.0, 30 μl of 500 mM ACC solution, and enzyme solution to make a final volume of 200 μl. Reactions were run for 10 minutes at 30°

C. The reaction was stopped with 1.8 ml of 2N HCl. After adding 300 µl 0.1% 2,4-dinitrophenylhydrazine, the mixture was incubated for 15 minutes at 30° C. The solution was then made basic by adding 2 ml of 2N NaOH. The optical density of the resulting brownish-red solution was determined at 540 nm with a spectrophotometer.

The kinetic value, $K_m$, for ACC deaminase was determined against ACC as the enzyme substrate for each of the ACC deaminases isolated. ACC deaminase activity was shown to be linear with respect to enzyme concentration using saturating levels of ACC (50 mM). An estimated $K_m$ was determined for each extracted enzyme with ACC at sub-saturating concentrations. Activity was shown to be linear over time with respect to ACC concentration for the concentrations used to determine the actual $K_m$ values. Actual $K_m$ values were then determined for each extract using ACC concentrations between 0.2× and 2× of the estimated $K_m$, or ACC concentrations between 1 and 10 mM ACC. $K_m$ values were calculated from double reciprocal plots, plotting the reciprocal of the substrate concentration on the x-axis and the reciprocal of the velocity (α-ketobutyrate formed) on the y-axis. The x-intercept (at y equals 0) is equal to $-1/K_m$. The $K_m$ values for the ACC deaminases extracted from nine different strains were determined and were generally within 3-fold of one another (from ~4 to ~12 mM). The $K_m$ data demonstrates that essentially all ACC deaminases are functionally equivalent and can be used in the present invention. The $K_m$ values for ACC deaminases from numerous isolates are listed in Table II.

TABLE II

Kinetic Values for Different Bacterial Isolates

| Strain | $K_m$ [mM ACC] |
|---|---|
| 6G5 | 9.0 |
| 3P2 | 5.8 |
| 388 | 8.6 |
| 391 | 17.4 |
| 392 | 7.1 |
| 393 | 5.9 |
| 401 | 7.8 |
| T44 | 11.8 |
| PR-1 | 4.1 |

Once an isolate capable of degrading ACC is selected for further study, the gene encoding the ACC deaminase must be isolated. A general strategy for isolation and purification of the ACC deaminase gene from the selected Pseudomonas strain 6G5 is as follows. Isolate 6G5 is an exemplary embodiment for further illustrative embodiments, but other isolates would be useful as well. A cosmid bank of the Pseudomonas strain 6G5 is constructed, cloned and introduced into E. coli. The clone carrying the ACC deaminase gene is identified by selection on minimal media containing ACC as the sole nitrogen source. The coding region of the ACC deaminase gene is then identified and sequenced. Cloning and genetic techniques, unless otherwise indicated, are generally those described by Sambrook et al. (1989). While this strategy was utilized to obtain the ACC deaminase gene from the 6G5 strain, other strategies could be employed with similar success and are considered to be within the scope of the invention. The detailed procedure for isolating the ACC deaminase gene from the 6G5 strain is set forth below.

The cell pellet from a 200 ml L-Broth (Miller 1972) late log phase culture of strain 6G5 was resuspended in 10 ml of Solution I (Birnboim and Doly 1979) in order to obtain chromosomal DNA. Sodium dodecylsulfate (SDS) is added to a final concentration of 1% and the suspension subjected to three freeze-thaw cycles, each consisting of immersion in dry ice for 15 minutes and in water at 70° C. for 10 minutes. The lysate is then extracted four times with equal volumes of phenol:chloroform (1:1; phenol saturated with TE buffer at $pH_{8.0}$) (TE=10 mM Tris; 1.0 mM EDTA) and the phases separated by centrifugation (15000 g; 10 minutes). The ethanol-precipitable material is pelleted from the supernatant by brief centrifugation (8000 g; 5 minutes) following addition of two volumes of ethanol. The pellet is resuspended in 5 mls of TE buffer and dialyzed for 16 hours at 4° C. against 2 liters of TE buffer. This preparation yields a 5 ml DNA solution of about 552 µg/ml.

Three 50 µl fractions of the Pseudomonas 6G5 DNA are then partially digested with EcoRI to generate fragments greater than 20 Kb. The three 50 µg fractions are digested with 0.125 units, 0.062 units, and 0.032 units, respectively, of EcoRI per µg DNA in a total volume of 1.25 ml each and incubated at 37° C. for 30 minutes. The fractions are pooled and extracted once with an equal volume of 1:1 phenol:chloroform saturated with TE buffer at pH 7.6 to remove the enzyme. The DNA is precipitated with two volumes of ethanol and pelleted by centrifugation (12000 g, 5 minutes). The dried DNA pellet is resuspended in 500 µl TE buffer, and layered on top of a sucrose gradient. The 10%–40% sucrose gradient is prepared in seven 5.5 ml layers using 5% sucrose increments in 50 Mm Tris pH8.0, 5 mM EDTA, 0.5 mM NaCl. The gradients are centrifuged at 26,000 rpm for 18 hours in a Beckmann SW28 rotor. The tube is punctured on the bottom and 1 ml fractions are collected. From each fraction, 20 µl aliquots are run on a 1% agarose gel along with lambda DNA HindIII digested size standards. The fractions which contain DNA fragments greater than 20 Kb are combined. In the instant description, seven fractions were combined. The pooled sample is desalted and concentrated over Amicon Centricon-10® columns. The 0.5 ml concentrated sample is rinsed with 2 ml TE buffer, and again concentrated to 0.5 ml. The DNA sample is precipitated with 1 ml ethanol and the dry pellet resuspended in 50 µl TE buffer. To estimate the DNA yield, 2 µl of the sample is run on a 1% agarose gel along with 0.8 µg lambda DNA cut with BstEII as a standard. From the gel, the concentration is estimated at 35 ng/µl of the Pseudomonas 6G5 DNA partial EcoRI fragments which are greater than 20 Kb.

A cosmid bank is constructed using the vector pMON17016. This vector is a derivative of the phage lambda cos plasmid pHC79 (Hohn and Collins 1980). The pMON17016 plasmid is constructed by introducing the HindIII-BglII fragment from pT7-7 (Tabor and Richardson 1985) containing the gene 10 promoter region from phage T7 into the HindIII-BamHI cut pHC79. The clone interrupts and inactivates the tetracycline resistance gene of pHC79 leaving the ampicillin resistance gene intact. The introduced T7 promoter is not required for the function of the cosmid clone. The pMON17016 vector is cut with EcoRI and treated with calf alkaline phosphatase (CAP) in preparation for cloning. The vector and target sequences are ligated as follows. 1.25 µg (25 µl of 50 ng/µl) of the pMON17016 vector DNA (EcoRI/CAP) is combined with 0.63 µg (18 µl of 35 ng/µl) of size fractionated 6G5 EcoRI fragments, and precipitated with two volumes of ethanol. The sample is centrifuged and the dry DNA pellet resuspended in 6 µl $H_2O$. To this solution, 1 µl of the 10× ligation buffer (250 mM Tris-HCl pH 8.0, 100 mM $MgCl_2$, 100 mM Dithiothreitol, 2 mM Spermidine), 2 µl of 100 mM ATP (Adenosine 5'-triphosphate) solution, and 1 µl of 400 unit/µl T4 DNA ligase (New England Biolabs) is added. The ligation mix is incubated at room temperature (RT) for 6 hours.

From the 10 µl of pMON17016/6G5 ligated DNA sample, 3 µl is packaged into lambda phage particles (Stratagene; Gigapack Plus) using the manufacturer's procedure. To establish the cosmid titer, serial dilutions are made and used to infect the host bacteria. A culture of the host MM294 (Talmadge and Gilbert 1980) *E. coli* is grown at 30° C. in L-Broth containing 0.2% maltose. A 100 µl sample of MM294 is diluted with 100 µl SM buffer (SM=50 mM Tris pH7.5, 100 mM NaCl, 8 mM MgSO$_4$, 0.01% gelatin) and infected with 10 µl fractions of the packaged cosmid. The sample is incubated at RT for 15 minutes. One ml of L-Broth is added to the sample and incubated at 37° C. for 30 minutes. The infected bacteria are then concentrated by centrifugation (4000 rpm, 4 minutes.) and plated on L-Broth agar plates containing 100 µl/ml carbenicillin. The plates are incubated at 37° C. overnight. The cosmid titer typically observed is estimated at ~8.5×10$^5$ clones total from the 3 µl ligated pMON17016/6G5 DNA, or 2.8×10$^6$ clones per µg 6G5 EcoRI DNA.

To select the cosmid clones which contain the ACC deaminase gene, the 6G5 library is then plated on media containing ACC as a sole nitrogen source. The plates contain 1.5% nitrogen free agar, 2 mM MgSO$_4$, 0.2% glucose, 0.1 mM CaCl$_2$, 1× M9 salts (M9 salts=6 g Na$_2$HPO$_4$.7H$_2$O, 3 g KH$_2$PO$_4$, 1.5 g NaCl, per liter), 1 mM Thiamine-HCl, 100 µg/ml carbenicillin, and 3 mM ACC. The MM294 cells are infected with 35 µl (~5.6×10$^4$ clones) packaged cosmid as described above, washed two times with 1× M9 salts, and plated on five plates. Growth was evident after a 3 day incubation at 37° C. After a 6 day incubation, approximately 300 cosmids (1 per 200) grew on the minimal media plates containing ACC as a sole nitrogen source. There is no growth evident after 6 days on the control plate which did not contain ACC as a supplemental source of nitrogen.

Several colonies that grew on the minimal media containing ACC are then screened. All the samples in the instant description had different size cosmid inserts and most contained several common EcoRI fragments. The three smallest clones are screened by restriction deletions and subcloning of the common fragments. The activity of the ACC deaminase gene is monitored by plating the clones on minimal media containing ACC as described above. The screens identified a clone containing a ~10.6 Kb insert which retained activity. The insert is then subcloned on a BamHI-XbaI fragment into the pUC118 plasmid (Viera and Messing 1987). Subsequent HindIII and SmaI deletions narrowed down the ACC deaminase activity to the 2.4 Kb insert which allowed the clone to grow on minimal media with ACC as the sole nitrogen source. The pUC118 plasmid containing the 2.4 Kb insert is designated pMON10027.

Both strands of the 2.4 Kb insert of pMON10027 were then sequenced using the USB Sequenase® DNA sequencing kit following the manufacturer's directions. A 1017 base pair (bp) open reading frame was identified as the coding sequence of the ACC deaminase gene (FIG. 2). This sequence is identified as SEQ ID NO:1.

To further demonstrate the equivalence of the ACC deaminase genes from different organisms, the DNA sequence of a second gene was determined. The Pseudomonas 3F2 isolate was identified in the initial screen as an organism capable of growth on medium containing ACC as sole nitrogen source as previously described. Conversion of ACC to α-ketobutyric acid in vitro (as described for the 6G5 organism) demonstrated that this organism also contained an ACC deaminase enzyme. The polymerase chain reaction (PCR) was used to clone the 3F2 ACC deaminase. Oligodeoxynucleotides for priming off of 3F2 DNA based on the known 6G5 sequence were designed. The sequences of the 5' and 3' oligonucleotides are as follows:

5' oligonucleotide:

CCCGGATCCATGAATCTGAATCGTTTT        (SEQ ID NO:11)

3' oligonucleotide:

CCCGGATCCGCCGTTACGAAACAGGAA        (SEQ ID NO:12)

These oligonucleotides begin with a sequence that incorporates a BamHI site into the PCR product to facilitate subsequent cloning. Each is identical to either the 6G5 sequence over the first 18 (5') or last 18 (3') nucleotides, which are underlined. The 3F2 DNA was prepared as previously described for 6G5. The PCR reaction was carried out under conditions that would permit annealing of the oligonucleotides to 3F2 DNA even if some mismatch between the 3F2 and 6G5 sequences existed. The PCR reaction was run for 30 cycles with 15 second extensions for each subsequent cycle. Each cycle consisted of:

| | |
|---|---|
| 94° C. | 1 minute |
| 40° C. | 2 minutes |
| 72° C. | 3 minutes plus 15 second extensions |

The PCR-amplified 3F2 DNA contains the first 18 (5') and last 18 (3') nucleotides of isolate 6G5's ACC deaminase nucleotide sequence incorporated into the oligonucleotides and thus may not correspond to the actual 3F2 gene in the areas of the first and last 18 nucleotides. Therefore, the actual identity of the first and last six amino acids of the 3F2 ACC deaminase may not be the same as the enzyme in the original 3F2 organism. Because a high degree of homology between the 3F2 DNA and the oligonucleotide primers is essential for successful DNA amplification, the 3F2 and 6G5 sequences must be quite similar.

The product of the PCR amplification was cloned into BamHI-cut pBSSK+ (Stratagene) and subjected to dideoxy DNA sequencing as previously described. The sequence of the gene was determined using a series of oligonucleotide primers derived from internal DNA sequences. The sequence of the 3F2 gene and the derived amino acid sequence of the ACC deaminase is shown in FIG. 17. The nucleotide sequence is identified as SEQ ID NO:15 and the amino acid sequence is identified as SEQ ID NO:16. A comparison of the derived amino acid sequences or the 6G5 and 3F2 enzymes indicates that they are highly homologous, having 96% identity and 99% similarity when conservative amino acid substitutions are considered. The sequence conservation, taken together with the kinetic data obtained on these two enzymes clearly indicates the conserved nature of the ACC deaminase in nature.

Once an ACC deaminase gene has been identified and isolated, it must be engineered for plant expression. To introduce the ACC deaminase gene into a plant, a suitable chimeric gene and transformation vector must be constructed. A typical chimeric gene for transformation into a plant will include a promoter region, a heterologous structural DNA coding sequence and a 3' non-translated polyadenylation site. A heterologous structural DNA coding sequence means a structural coding sequence that is not native to the plant being transformed or a structural coding sequence that has been engineered for improved characteristics of its protein product. Heterologous with respect to the promoter means that the coding sequence does not exist in nature in the same gene with the promoter to which it is now attached. Chimeric means a novel non-naturally occurring gene which is comprised of parts of different genes. In preparing the transformation vector, the various DNA fragments may be manipulated as necessary to create the desired vector. This includes using linkers or adaptors as necessary to form suitable restriction sites or to eliminate unwanted restriction sites or other like manipulations which are known to those of ordinary skill in the art.

Promoters which are known or found to cause transcription of the ACC deaminase gene in plant cells can be used in the present invention. Such promoters may be obtained from plants, plant pathogenic bacteria or plant viruses and include, but are not necessarily limited to, the 35S and 19S promoters of cauliflower mosaic virus (CaMV35S and CaMV19S), the full-length transcript promoter from the figwort mosaic virus (FMV35S) and promoters isolated from plant genes such as EPSP synthase, ssRUBISCO genes and promoters obtained from T-DNA genes of *Agrobacterium tumefaciens* such as nopaline and mannopine synthases. The particular promoter selected should be capable of causing sufficient expression to result in the production of an effective amount of ACC deaminase to substantially inhibit the production of ethylene. Those skilled in the art will recognize that the amount of ACC deaminase needed to inhibit ethylene production may vary with the type of plant and the tissues within the plant of interest.

Particularly useful promotors for use in the present invention are fruit specific promoters which are expressed during ethylene production in the fruit and the full-length transcript promoter from the figwort mosaic virus (FMV35S). The FMV35S promoter is particularly useful because of its ability to cause uniform and high levels of expression of ACC deaminase in plant tissues. The DNA sequence of a FMV35S promoter is presented in FIG. 22 and is identified as SEQ ID NO:17. Examples of fruit specific promoters include the E8, E4, E17 and J49 promoters from tomato (Lincoln, J. E., and Fischer, R. L. 1988), as well as the 2A11 promoter as described in U.S. Pat. No. 4,943,674.

The promoters used for expressing the ACC deaminase gene of this invention may be further modified if desired to alter their expression characteristics. For example, the CaMV35S promoter may be ligated to the portion of the ssRUBISCO gene which represses the expression of ssRUBISCO in the absence of light, to create a promoter which is active in leaves but not in roots. The resulting chimeric promoter may be used as described herein. As used herein, the phrase "CaMV35S" or "FMV35S" promoter includes variations of these promoters, e.g. promoters derived by means of ligation with operator regions, random or controlled mutagenesis, addition or duplication of enhancer sequences, etc.

The 3' non-translated region contains a polyadenylation signal which functions in plants to cause the addition of polyadenylated nucleotides to the 3' end of the RNA sequence. Examples of suitable 3' regions are the 3' transcribed, non-translated regions containing the polyadenylation signal of the tumor-inducing (Ti) plasmid genes of Agrobacterium, such as the nopaline synthase (NOS) gene, and plant genes like the 7s soybean storage protein genes and the pea E9 small subunit of the RuBP carboxylase gene (ssRUBISCO).

The RNA produced by a DNA construct of the present invention also preferably contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequences can be part of the 5' end of the non-translated region of the native coding sequence for the heterologous coding sequence, or part of the promoter sequence, or can be derived from an unrelated promotor or coding sequence as discussed above.

A DNA construct of the present invention can be inserted into the genome of a plant by any suitable method. Suitable plant transformation vectors include those derived from a Ti plasmid of *Agrobacterium tumefaciens*, such as those disclosed by Herrera-Estrella (1983), Bevan (1983), Klee (1985) and U.S. Pat. No. 4,940,838. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, particle gun technology, and transformation using viruses. Methods for the introduction of vectors into maize, or other monocot cells would include, but are not limited to, the injection method of Neuhaus et al. (1987), the injection method of de la Pena et al. (1987) or the microprojectile methods of Klein et al. (1987) and McCabe et al. (1988).

The construction of vectors capable of being inserted into a plant genome via *Agrobacterium tumefaciens* mediated delivery is known to those of ordinary skill in the art. Typical plant cloning vectors comprise selectable and scoreable marker genes, T-DNA borders, cloning sites, appropriate bacterial genes to facilitate identification of transconjugates, broad host-range replication and mobilization functions and other elements as desired.

If Agrobacterium mediated delivery is chosen, once the vector has been introduced into the disarmed Agrobacterium strain, the desired plant can then be transformed. Any known method of transformation that will work with the desired plant can be utilized.

Plants particularly suitable for use in this invention are tomato, banana, kiwi fruit, avocado, melon, mango, papaya, apple, peach, and other climacteric fruit plants. The present invention should also be suitable for use in the following non-climacteric species: strawberry, lettuce, cabbage, cauliflower, onions, broccoli, cotton, canola and oilseed rape. Other plant species that are affected by the ethylene induced ripening process may also benefit from the teachings of the present invention especially those in which ethylene production is critical to the growth of the plant or the ripening or development of the fruit of the plant. In the flower industry, particularly desirable flower species would be carnations, roses and the like. This list should be interpreted as only illustrative and not limiting in any sense.

In order to obtain constitutive expression of the ACC deaminase gene in plants, the gene was cloned into the transformation vector pMON977. The ACC deaminase gene isolated from the 6G5 isolate was used in the transformation vectors prepared herein. The pMON977 plasmid (FIG. 3) contains the following well characterized DNA segments. First, the 0.93 Kb fragment isolated from transposon Tn7 which encodes bacterial spectinomycin/streptomycin resistance (Spc/Str), and is a determinant for selection in *E. coli* and *Agrobacterium tumefaciens* (Fling et al. 1985). This is joined to the chimeric kanamycin resistance gene engineered for plant expression to allow selection of the transformed tissue. The chimeric gene consists of the 0.35 Kb cauliflower mosaic virus 35S promoter (P-35S) (Odell et al. 1985), the 0.83 Kb neomycin phosphotransferase type II gene (NPTII), and the 0.26 Kb 3'-nontranslated region of the nopaline synthase gene (NOS 3') (Fraley et al. 1983). The next segment is the 0.75 Kb origin of replication from the RK2 plasmid (ori-V) (Stalker et al. 1981). This is joined to the 3.1 Kb SalI to PvuI fragment from pBR322 which provides the origin of replication for maintenance in *E. coli* (ori-322), and the bom site for the conjugational transfer into the *Agrobacterium tumefaciens* cells. Next is the 0.36 Kb PvuI to BclI fragment from the pTiT37 plasmid, which contains the nopaline-type T-DNA right border region (Fraley et al. 1985). The last segment is the expression cassette consisting of the 0.65 Kb cauliflower mosaic virus (CaMV) 35S promoter enhanced by duplication of the promotor sequence (P-E35S) (Kay et al. 1987), a synthetic multilinker with several unique cloning sites, and the 0.7 Kb 3' nontranslated region of the pea rbcS-E9 gene (E9 3') (Coruzzi et al. 1984 and Morelli et al. 1985).

Figure 4:
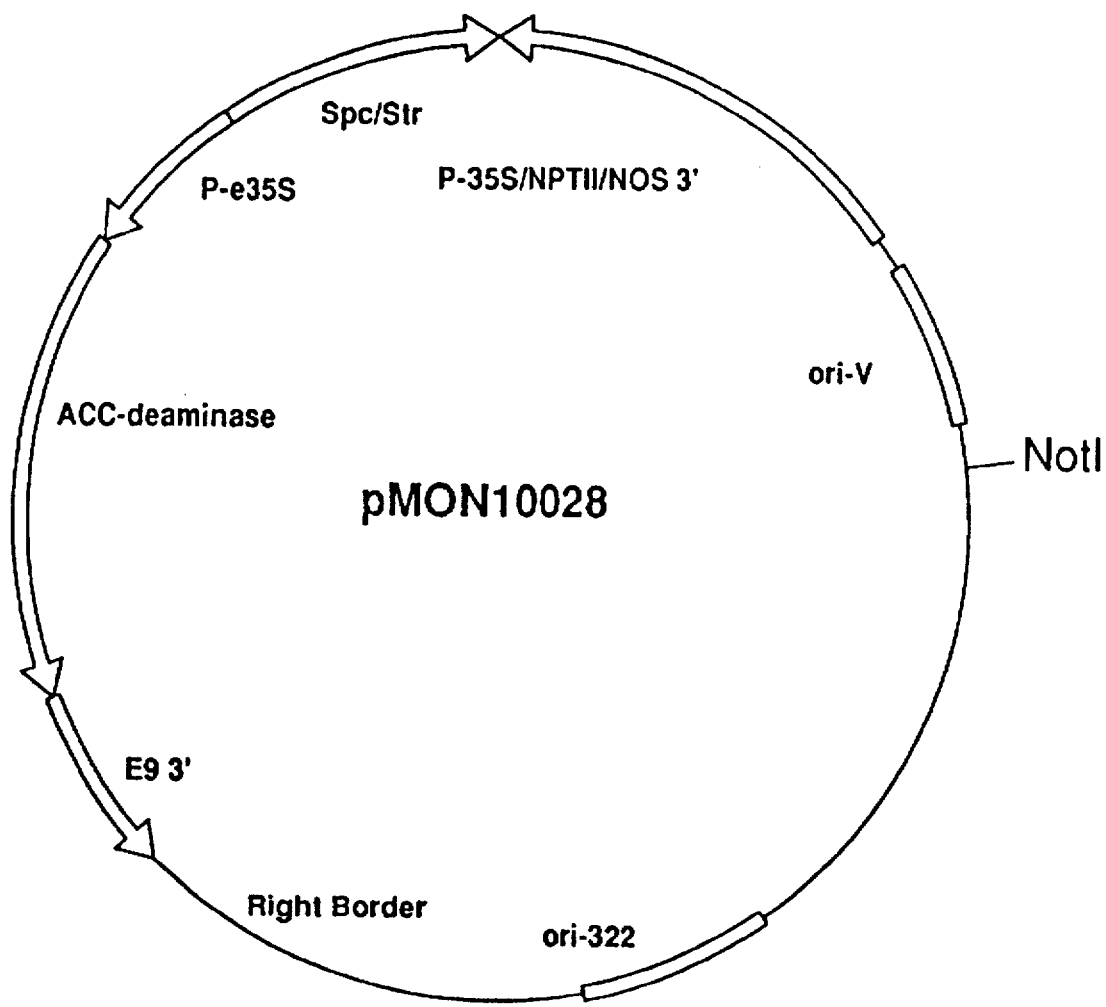
FIG. 4 illustrates a plasmid mop of pMON10028.
Figure 5:
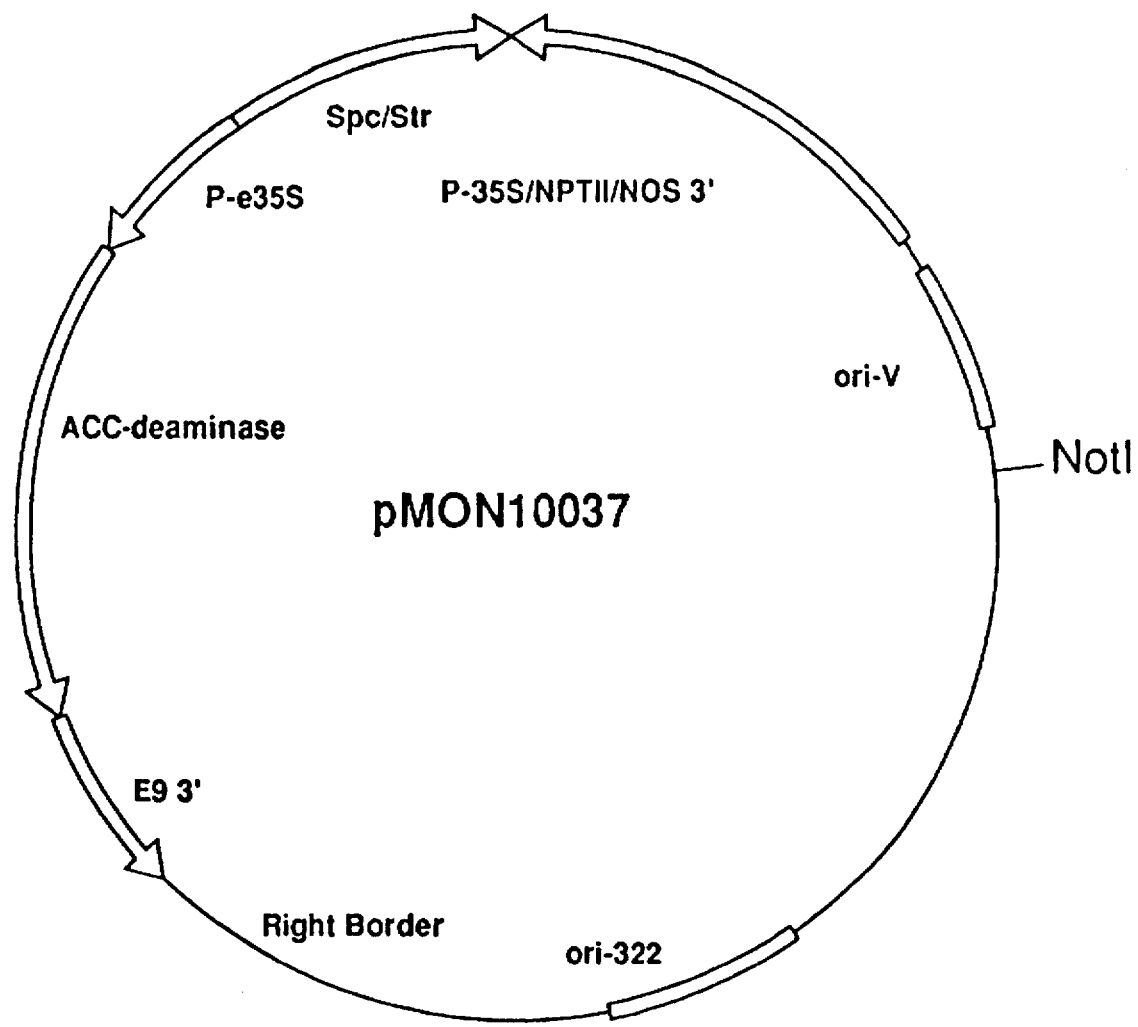
FIG. 5 illustrates a plasmid map of pMON10037.

Two different size fragments both containing the ACC deaminase gene from pMON10027 were introduced between the E35S promoter and the E9 3' end of pMON977. First, the 1071 bp EcoRV-SacI fragment from pMON10027 was introduced into the StuI-SacI cut pMON977, generating the pMON10028 vector (FIG. 4). Second, the 1145 bp EcoRV-EcoRV fragment from pMON10027 was introduced into the StuI cut pMON977, generating the pMON10037 vector (FIG. 5).

In order to construct vectors capable of directing expression of ACC deaminase specifically to fruit, a tomato fruit specific transcriptional promoter needed to be isolated. The promoter that was chosen is known to be induced to express at high levels in the presence of ethylene and is also known to be limited to the tomato fruit (Lincoln, J. and Fischer, R. 1988). The DNA sequence of the promoter for this gene, E8, has been published (Deikman et al. 1988). The DNA sequence of the E8 promotor is designated SEQ ID NO:10 and is illustrated in FIG. 14. While this promoter was chosen, other fruit specific promoters would also be useful and their identification and isolation routine to one of ordinary skill in the art. The promoter fragment E8 was isolated using standard polymerase chain reaction techniques. Oligonucleotides complementary to the E8 promoter were synthesized. The DNA sequences of the 5' and 3' oligonucleotides were as follows:

5' oligonucleotide:

GAAGGAAGCT TCACGAAATC GGCCCTTATT (SEQ ID NO:2)

3' oligonucleotide:

GGGGCTTTAG ATCTTCTTTT GCACTGTGAA (SEQ ID NO:3).

The 5' oligonucleotide introduced a HindIII site approximately 1040 nucleotides 5' to the start of transcription. The 3' oligonucleotide introduces a BglII site approximately 20 nucleotides beyond the start of transcription. The PCR product is an approximately 1060 nucleotide fragment that can be cloned as a HindIII to BglII fragment. This promoter fragment will confer tissue-specific expression upon any coding sequence placed adjacent to it in an appropriate orientation.

The PCR reaction was performed essentially as recommended by the manufacturer of the GeneAmp kit (Perkin Elmer-Cetus). The reaction mix consisted of the following:

| | |
|---|---|
| water | 58.5 µl |
| 10X buffer | 10 µl |
| dNTP mix | 16 µl |
| 5' primer | 75 pM in 3.0 µl |
| 3' primer | 75 pM in 3.0 µl |
| tomato DNA | 1.24 µg in 2 µl |
| Ampltaq DNA polymerase | 0.5 µl |

The PCR reaction was run using the following temperature/time combination for 28 cycles:

| | |
|---|---|
| 94° C. | 1 minute |
| 60° C. | 2 minutes |
| 72° C. | 3 minutes. |

Figure 6:
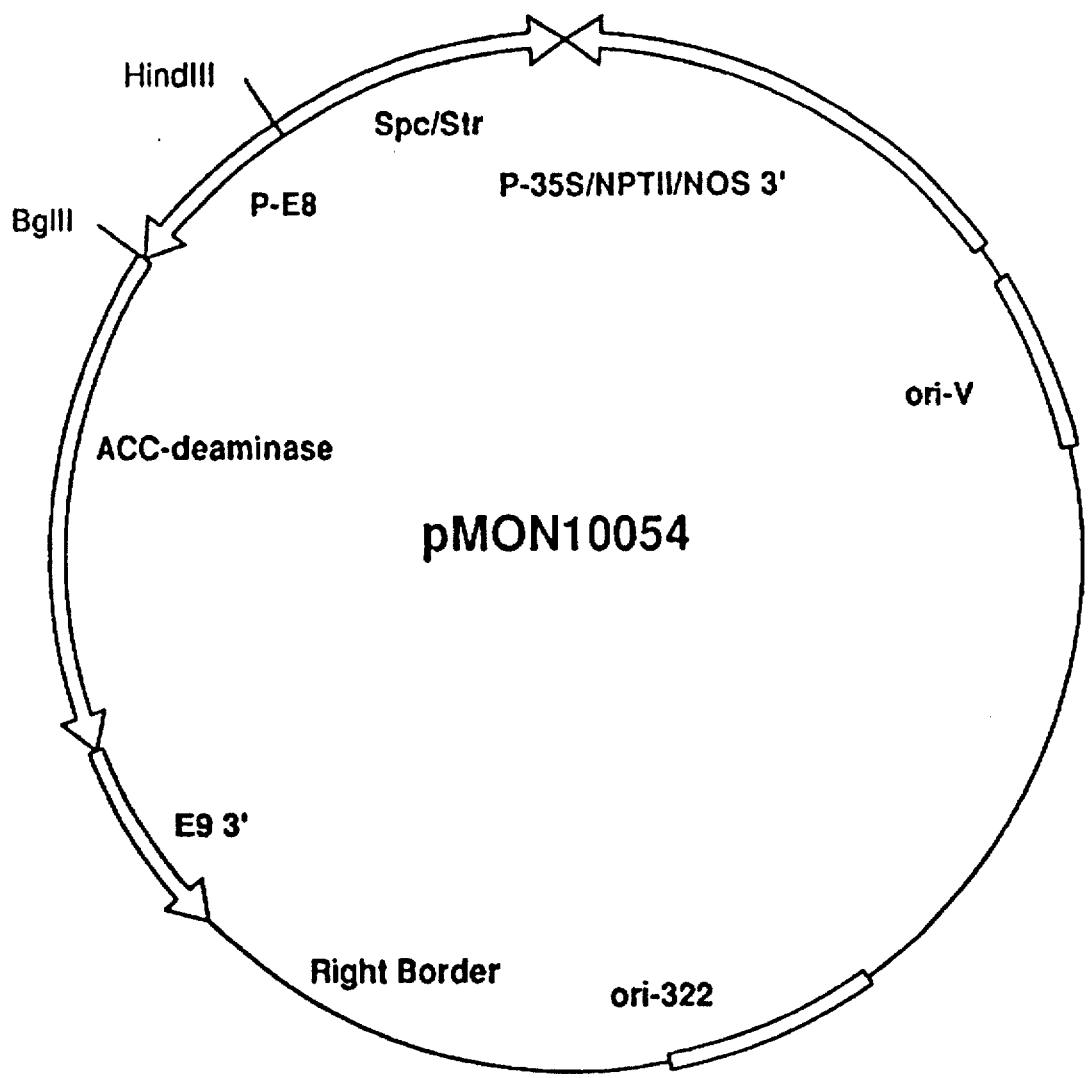
FIG. 6 illustrates a plasmid map of pMON10054.

Following completion, a PCR product of the correct size was observed. The fragment was purified by extraction with an equal volume of 1:1 phenol:chloroform followed by ethanol precipitation. The PCR fragment was then cut with HindIII and BglII so that it could be ligated to pMON10037 DNA. The PCR fragment was then ligated to pMON10037 DNA that had been cut with the same enzymes to remove the CaMV35S promoter sequence. The resulting plasmid contains the E8 promoter in the same location as the CaMV35S promoter of pMON10037 and was named pMON10054 (FIG. 6).

Both of the pMON10028 and pMON10037 vectors can be mobilized into the ABI Agrobacterium strain. The ABI strain is the A208 *Agrobacterium tumefaciens* carrying the disarmed pTiC58 plasmid pMP90RK (Koncz and Schell 1986). The Ti plasmid does not carry the T-DNA phytohormone genes, and the strain is therefore unable to cause the crown gall disease. Mating of pMON vectors into ABI is done by the triparental conjugation system using the helper plasmid pRK2013 (Ditta et al. 1980). When the plant tissue is incubated with the ABI::pMON conjugate, the vector is transferred to the plant cells by the vir functions encoded by the disarmed pMP90RK Ti plasmid. The vector opens at the T-DNA right border region, and the entire pMON vector sequence is inserted into the host plant chromosome. The Ti plasmid does not transfer to the plant cell but remains in the Agrobacterium.

The following examples further demonstrate several preferred embodiments of this invention. Those skilled in the art will recognize numerous equivalents to the specific embodiments described herein. Such equivalents are intended to be within the scope of the claims.

EXAMPLE 1

Transformed tobacco plants have been generated using the ABI::pMON10028 and the ABI::pMON10037 vectors, to demonstrate the expression of the ACC deaminase gene in plants.

Tobacco cells were transformed using the tobacco leaf disc method. The tobacco leaf disc transformation protocol employed healthy leaf tissue about 1 month old. After a 15–20 minute surface sterilization with 10% Clorox plus a surfactant, the tobacco leaves were rinsed 3 times in sterile water. Using a sterile paper punch, leaf discs were punched and placed upside down on MS104 media (MS salts 4.3 g/l, sucrose 30 g/l, B5 vitamins 500× 2 ml/l, NAA 0.1 mg/l, and BA 1.0 mg/l) for a 1 day preculture.

The discs were then inoculated with an overnight culture of disarmed Agrobacterium ABI containing the subject vector that had been diluted 1/5 (i.e. about 0.60OD). The inoculation was done by placing the discs in centrifuge tubes with the culture. After 30 to 60 seconds, the liquid was drained off and the discs were blotted between sterile filter paper. The discs were then placed upside down on MS104 feeder plates with a filter disc to co-culture.

After 2-3 days of co-culture, the discs were transferred, still upside down, to selection plates with MS104 media. After 2-3 weeks, callus formed, and individual clumps were separated from the leaf discs. Shoots were cleanly cut from the callus when they were large enough to distinguish from stems. The shoots were placed on hormone-free rooting media (MSO: MS salts 4.3 g/l, sucrose 30 g/l, and B5 vitamins 500× 2 ml/l) with selection. Roots formed in 1-2 weeks. Any leaf callus assays were preferably done on rooted shoots while still sterile. Rooted shoots were placed in soil and were kept in a high humidity environment (i.e. plastic containers or bags). The shoots were hardened off by gradually exposing them to ambient humidity conditions.

In order to assay for ACC deaminase in the leaves, tobacco leaf samples were collected and frozen in liquid nitrogen. One gram of tissue was kept frozen under liquid nitrogen and ground to a fine powder. One ml of extraction buffer (100 mM Tris $pH_{7.1}$, 10 mM EDTA, 35 mM KCl, 20% glycerol, 5 mM DTT, 5 mM L-ascorbate, 1 mM benzamidine, 1 mg/ml BSA) was added to the sample and ground for 45 seconds, then immediately centrifuged (12,000 g, 3 minutes) to remove the leaf debris. To remove small molecules, 250 µl of the extract was run over a 1 ml Sephadex G-50 spin column which was previously equilibrated with the above extraction buffer (less the BSA).

The extracts were assayed for the relative amount of the ACC deaminase enzyme activity in the transformed plant tissue. The ACC deaminase enzyme converts the ACC substrate into α-ketobutyrate and ammonia. The α-ketobutyrate was reacted with 2-4-dinitrophenyl-hydrazine hydrochloride to form a hydrazone derivative whose optical density was measured at 520 nm following addition of NaOH. The optical density values are a measure of the amount of ACC deaminase in the plant extract. The assay reaction mix contained a 50 µl sample of the tobacco leaf extract, 100 mM Tris $pH_{8.6}$, and 50 mM ACC in a final volume of 150 µL. The reaction was incubated at 30° C. for 1 minute, and terminated with 50 µl of 0.56M HCl. A 0.6 ml aliquot of 0.1% 2,4-dinitrophenyl-hydrazine in 2N HCl was added. The sample was boiled for 2 minutes, cooled to room temperature, and 0.2 ml of 40% NaOH was added. A centrifugation (12,000 g, 5 minutes) removes the precipitate. The optical density of the supernatant was measured at 520nm, which indicated the relative amount of the ACC deaminase enzyme being produced in the plants. Non-transformed tobacco plants were used as negative controls.

Several tobacco leaf extracts were assayed and the ACC deaminase activity was found to range from 0.6 to 7.5 mmoles product (α-ketebutyrate acid)/mg total protein/minute. These assay results demonstrated that the ACC deaminase was being expressed in the tobacco plant.

EXAMPLE 2

Transformed tomato plants have been generated using the ABI::pMON10028 and the ABI::pMON10037 vectors, and the expression of the ACC deaminase gene has been demonstrated in these plants.

Tomato plant cells were transformed utilizing the Agrobacterium strains described above generally by the method as described in McCormick et al. (1986). In particular, cotyledons were obtained from 7-8 day old seedlings. The seeds were surface sterilized for 20 minutes in 30% Clorox bleach and were germinated in Plantcons boxes on Davis germination media. Davis germination media is comprised of 4.3 g/l MS salts, 20 g/l sucrose and 10 mls/l Nitsch vitamins, $pH_{5.8}$. The Nitsch vitamin solution is comprised of 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine. The seeds were allowed to germinate for 7-8 days in the growth chamber at 25° C., 40% humidity under cool white lights with an intensity of 80 einsteins $m^{-2}s^{-1}$. The photoperiod was 16 hours of light and 8 hours of dark.

Once germination occurred, the cotyledons were explanted using a #15 feather blade by cutting away the apical meristem and the hypocotyl to create a rectangular explant. These cuts at the short ends of the germinating cotyledon increased the surface area for infection. The explants were bathed in sterile Davis regeneration liquid to prevent desiccation. Davis regeneration media is composed of 1× MS salts, 3% sucrose, 1× Nitsch vitamins, 2.0 mg/l zeatin, pH 5.8. This solution was autoclaved with 0.8% Noble Agar.

The cotyledons were pre-cultured on "feeder plates" composed of media containing no antibiotics. The media is composed of 4.3 g/l MS salts, 30 g/l sucrose, 0.1 g/l myo-inositol, 0.2 g/l $KH_2PO_4$, 1.45 mls/l of a 0.9 mg/ml solution of thiamine HCl, 0.2 mls of a 0.5 mg/ml solution of kinetin and 0.1ml of a 0.2 mg/ml solution of 2,4 D. This solution was adjusted to pH 6.0 with KOH. These plates were overlaid with 1.5-2.0 mls of tobacco suspension cells (TXD's) and a sterile Whitman filter which was soaked in 2COO5K media. 2COO5K media is composed of 4.3 g/l Gibco MS salt mixture, 1 ml B5 vitamins (1000X stock), 30 g/l sucrose, 2 mls/l PCPA from 2 mg/ml stock, and 10µl/l kinetin from 0.5 mg/ml stock. The cotyledons were cultured for 1 day in a growth chamber at 25° C. under cool white lights with a light intensity of 40-50 einsteins $m^{-2}s^{-1}$ with a continuous light photoperiod.

Cotyledons were then inoculated with a log phase solution of Agrobacterium containing the desired transgenic gene. The concentration of the Agrobacterium was approximately $5 \times 10^8$ cells/ml. The cotyledons were allowed to soak in the bacterial solution for six minutes and were then blotted to remove excess solution on sterile Whatman filter disks and were subsequently replaced to the original feeder plate where they were allowed to co-culture for 2 days. After the two days, cotyledons were transferred to selection plates containing Davis regeneration media with 2 mg/l zeatin riboside, 500 µg/ml carbenicillin, and 100 µg/ml kanamycin. After 2-3 weeks, cotyledons with callus and/or shoot formation were transferred to fresh Davis regeneration plates containing carbenicillin and kanamycin at the same levels. The experiment was scored for transformants at this time. The callus tissue was subcultured at regular 3 week intervals and any abnormal structures were trimmed so that the developing shoot buds would continue to regenerate. Shoots developed within 3-4 months.

Once shoots developed, they were excised cleanly from callus tissue and were planted on rooting selection plates. These plates contained 0.5× MSO containing 50 µg/ml kanamycin and 500 µg/ml carbenicillin. These shoots formed roots on the selection media within two weeks. If no roots appeared after 2 weeks, shoots were trimmed and replanted on the selection media. Shoot cultures were incubated in percivals at a temperature of 22° C. Shoots with roots were then potted when roots were about 2 cm in length.

The plants were hardened off in a growth chamber at 21° C. with a photoperiod of 18 hours light and 6 hours dark for 2–3 weeks prior to transfer to a greenhouse. In the greenhouse, the plants were grown at a temperature of 26° C. during the day and 21° C. during the night. The photoperiod was 13 hours light and 11 hours dark and the plants were allowed to mature.

Green tomato fruit and leaf samples were collected and frozen in liquid nitrogen. The samples were extracted and assayed using the procedures described for tobacco. The tomato extraction buffer contained 100 mM Tris pH7.1, 1 mM EDTA, 10% glycerol, 5 mM DTT, 5 mM L-ascorbate, 1 mM benzamidine, 1 mg/ml BSA. The extracts were assayed and the ACC deaminase activity was found to range from 1.6 to 11.2 mmoles of product/mg total protein/minutes reaction for the leaf tissue, and from 3.0 to 25.1 mmoles of product/mg total protein/minutes reaction for the tomato fruit tissue. The results of these assays demonstrated that the ACC deaminase was being expressed constitutively in the tomato plant.

EXAMPLE 3

Tomato plants transformed with a chimeric gene encoding ACC deaminase have also been assayed to determine the effect of the expression of ACC deaminase on the ripening of fruit of the tomato plant.

Plasmids pMON10028 and pMON10037 were introduced into tomato (*Lycopersicon esculentum* cv. UC82B) as described in Example 2.

Plants containing the genes were initially identified by resistance to kanamycin. Kanamycin resistant plants were further analyzed by ACC deaminase enzyme assays (as described above) and by routine western blot analysis using antibody prepared against purified ACC deaminase protein. Plants that expressed the ACC deaminase protein were chosen for further analysis.

Tomato plants that were identified as expressing the ACC deaminase gene were examined for inhibition of fruit ripening. R1 progeny of the primary transformants from two lines, designated 5673 and 5854, as well as nontransformed UC82B plants were grown under identical conditions in a greenhouse. Progeny of the transgenic plants were screened for the presence of the NPTII gene, indicating inheritance of the T-DNA. All plants, including the UC82B controls, produced flowers and initiated fruit development simultaneously. Plants were then scored for the day at which fruit entered the breaker stage (the stage when the fruit begins to turn red), indicating initiation of ripening. Plants that had been scored as NPTII positive from both of the transgenic lines showed a significant delay in initiation of ripening. The delay in onset of ripening was approximately one week. Fruits from the transgenic plants as well as UC82B controls were then removed from the plants at the breaker stage. Fruits were stored individually in 200 ml beakers at room temperature and allowed to ripen. The fruits from transgenic plants exhibited delays of from two to six weeks in the time it took to reach a fully ripe state. Thus, tomato plants expressing the ACC deaminase gene exhibited delays in both the initiation of ripening and the time that it took to progress through the stages of ripening after the process had been initiated.

EXAMPLE 4

*Nicotiana tabacum* plants transformed with pMON10028 and pMON10077 as described above have also been assayed to determine the effect of the expression of ACC deaminase in the plant on the life of the tobacco flowers. Tobacco plants expressing the ACC deaminase gene were identified using the same enzyme assay as used for the tomato plants. Enzyme assays were performed on tobacco leaves and flowers. Plants expressing the gene were assayed for the length of time that flowers were retained. Flowers were tagged at the point of anthesis (flower opening) and the time it took to reach a senesced stage was measured. While flowers from control plants showed significant wilting two days after anthesis, flowers from the transgenic plants expressing ACC deaminase were delayed in wilting by a full day.

EXAMPLE 5

The present invention may also be used in combination with other methods known to delay ripening in fruits. One such combination involves use of the ACC deaminase gene in combination with an antisense gene that inhibits ethylene production. A plasmid containing ACC deaminase in combination with an antisense gene for the pTOM13 cDNA has been prepared for this purpose (Holdsworth et al. 1987). The gene designated pTOM13 has been previously shown to inhibit ethylene production when placed in an antisense orientation in plants (Hamilton et al. 1980). It has been postulated that this gene encodes an enzyme that converts ACC to ethylene (presumably the enzyme is ACC oxidase) and inhibition of the synthesis of this enzyme with an antisense RNA leads to accumulation of ACC in plant tissue. A cDNA clone corresponding to the pTOM13 gene was isolated from a cDNA library prepared from ripening tomato fruit on the basis of its ability to hybridize to synthetic oligonucleotides prepared from the published pTOM13 sequence.

A cDNA library was purchased from Stratagene (Cat. #936004). This library was prepared from RNA isolated from ripening tomato fruit in the bacteriophage lambda cloning vector lambda-ZAP II. Oligonucleotide probes were prepared from segments of the pTOM13 published sequence as follows:

Oligonucleotide 1:

5' GGTGAACCAT GGAATTCCAC ATG 3'    (SEQ ID NO:4)

Oligonucleotide 2:

5' GCAATTGGAT CCCTTTCCAT AGC 3'    (SEQ ID NO:5)

Twenty thousand phage were plated on agar-containing plates as recommended by the manufacturer. The *E. coli* strain XL1-Blue, supplied by the manufacturer, was used for phage preparation. Phage plaques were transferred to nitrocellulose filters and baked in an 80° C. oven for 2 hours. Plates were prehybridized at 65° C. for 2 hours in the following solution:

- 6× SSC, 5× Denhardt's solution, 100 µg/ml denatured salmon sperm DNA, 20 mM Tris:HCl, pH 7.0, 0.1% SDS, 1.0 mM EDTA.
- 50× Denhardt's Solution=1.0 % each of Ficoll, polyvinylpyrrolidone, bovine servm albumin (Fraction V; Sigma) in water.
- 20× SSC=175 g sodium chloride and 88.2 g sodium citrate per liter of water. pH adjusted to 7.0 with NaOH.

After prehybridization, $^{32}$P-labelled oligonucleotides (Sambrook et al. 1989) were added to a final concentration of 500,000 cpm/ml hybridization solution for each oligonucleotide. Hybridization was performed at 50° C. for 48 hours. Filters were washed twice in 6× SSC at room temperature for 15 minutes and once at 50° C. for 15 minutes. They were then dried and exposed to X-ray film for 48 hours. Plaques corresponding to hybridizing phage were isolated and purified by repeating the above procedure at a density of phage where single plaques could easily be separated from adjacent, non-hybridizing plaques. The pTOM13 cDNA insert was rescued in the plasmid vector pBS SK- as described by the manufacturer (Stratagene). This plasmid was designated pMON11023.

Figure 7:
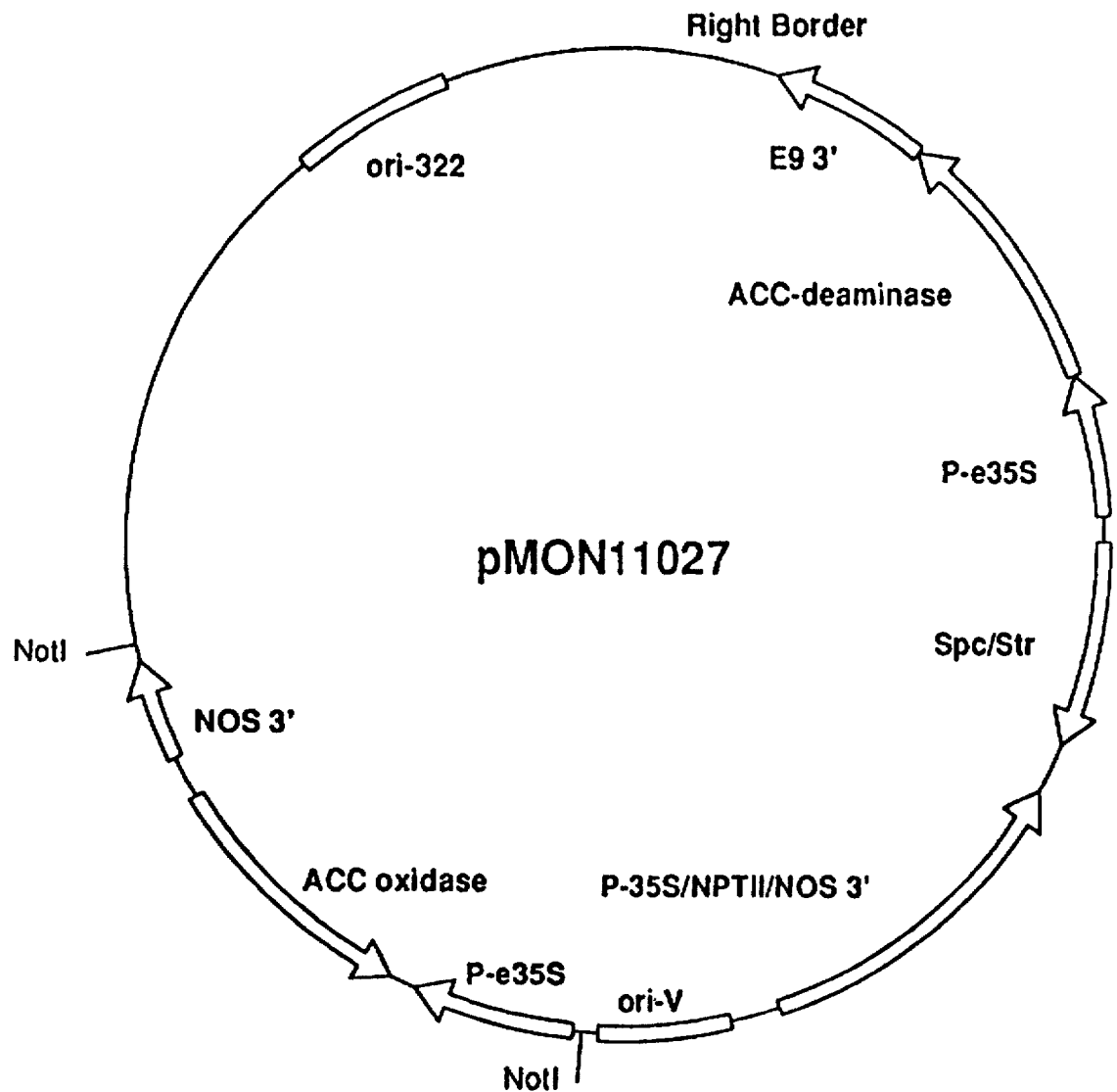
FIG. 7 illustrates a plasmid map of pMON11027.

A vector designed for expression of the pTOM13 cDNA insert in an antisense orientation was then prepared. The cDNA insert with adjacent polylinker was excised from pMON11023 by cutting with the restriction endonucleases BamHI and ClaI. The cDNA-containing portion of the plasmid was then cloned into pMON999 which had been cut with BglII and ClaI and treated with calf intestinal alkaline phosphatase. The resulting plasmid, pMON11025, contains the cDNA insert in an antisense orientation with respect to the CaMV35S promoter and a nopaline synthase 3' transcriptional terminator/polyadenylation site. This gene cassette can be excised as a single 2.2 kb NotI fragment. This NotI fragment was excised from pMON11025 and placed into the unique NotI site of pMON10028 to create pMON11027 (FIG. 7). This plasmid thus contains an antisense pTOM13 gene and a CaMV35S/ACC deaminase gene. This plasmid was introduced into Agrobacterium ABI using triparental mating as described above and used to transform tomato plants.

The resulting transformed plants should significantly inhibit the production of ethylene in the plant. It is expected that the action of the ACC deaminase gene in combination with the pTOM13 antisense gene will virtually eliminate ethylene synthesis and should further delay ripening of the fruit. It is expected that the combination of the ACC deaminase and the pTOM13 antisense gene will exhibit synergistic properties in the reduction of the formation of ethylene in the fruit or plant.

EXAMPLE 6

An alternate approach to reducing the rate of ethylene production in plant tissue involves overexpression of the gene encoding S-adenosylmethionine (SAM) decarboxylase. This enzyme degrades SAM which is the immediate precursor of ACC. The decarboxylated SAM is then converted to spermidine, a common polyamine. Since polyamines have themselves been reported to have anti-senescence properties in plants, it is anticipated that SAM decarboxylase may prevent ripening in two ways 1) the production of spermidine and 2) degradation of a precursor to ethylene.

The gene encoding SAM decarboxylase (SEQ ID NO: 9), illustrated in FIG. 15, has been cloned and its DNA sequence has been reported (Tabor and Tabor). The gene was cloned using PCR as described above in the protocol for isolation of the E8 promoter. E. coli DNA was purified as described above for the isolation of Pseudomonas 6G5 genomic DNA. Purified DNA was subjected to PCR as described above using the following oligonucleotides as primers:

5' oligonucleotide:

GGAGAAGATA AGATCTATGA AAAAACTGAA (SEQ ID NO:6)

3' oligonucleotide:

GCAGAAGTAA ATAGATCTGG CGGAGCC (SEQ ID NO:7).

Figure 8:
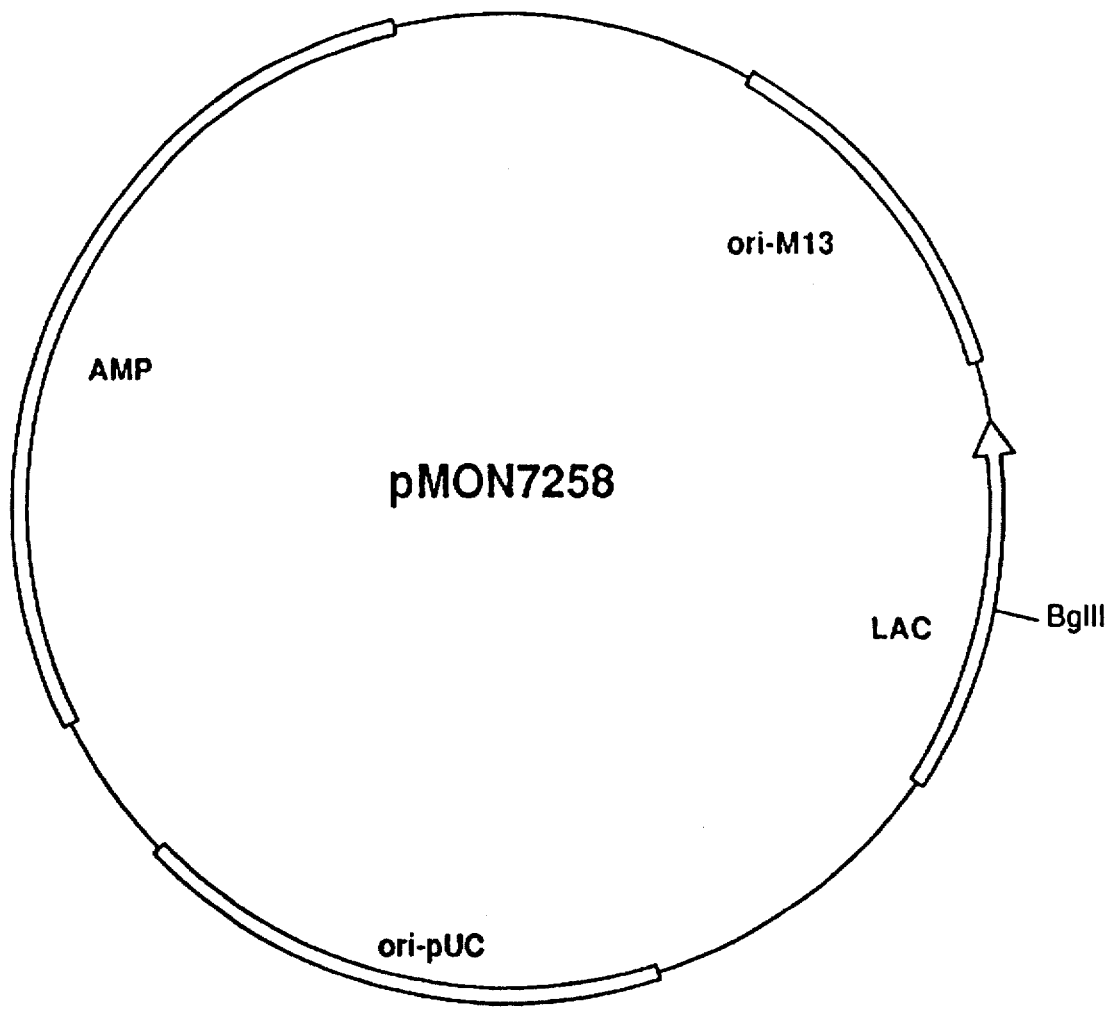
FIG. 8 illustrates a plasmid map of pMON7258.
Figure 9:
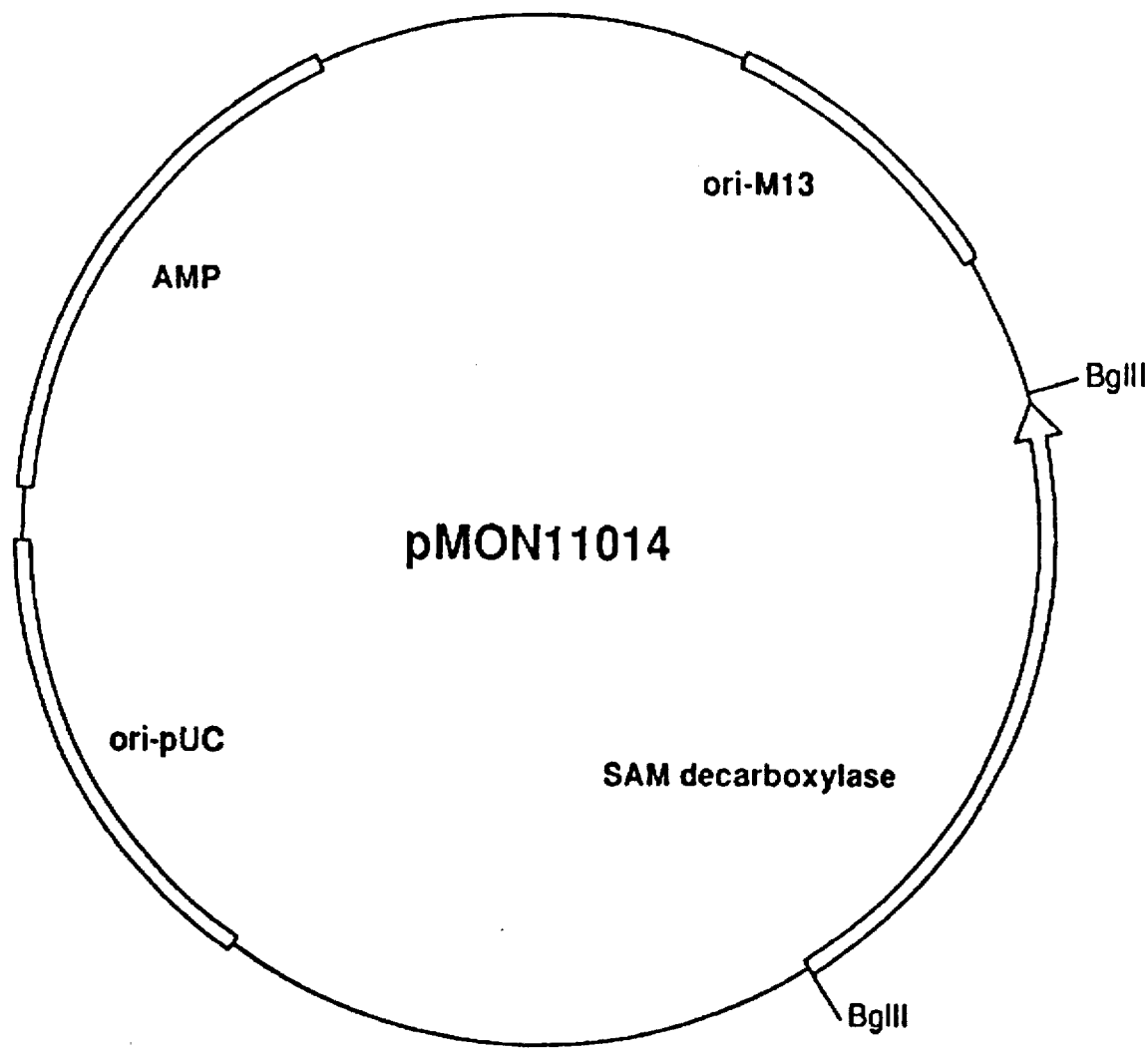
FIG. 9 illustrates a plasmid map of pMON11014.
Figure 10:
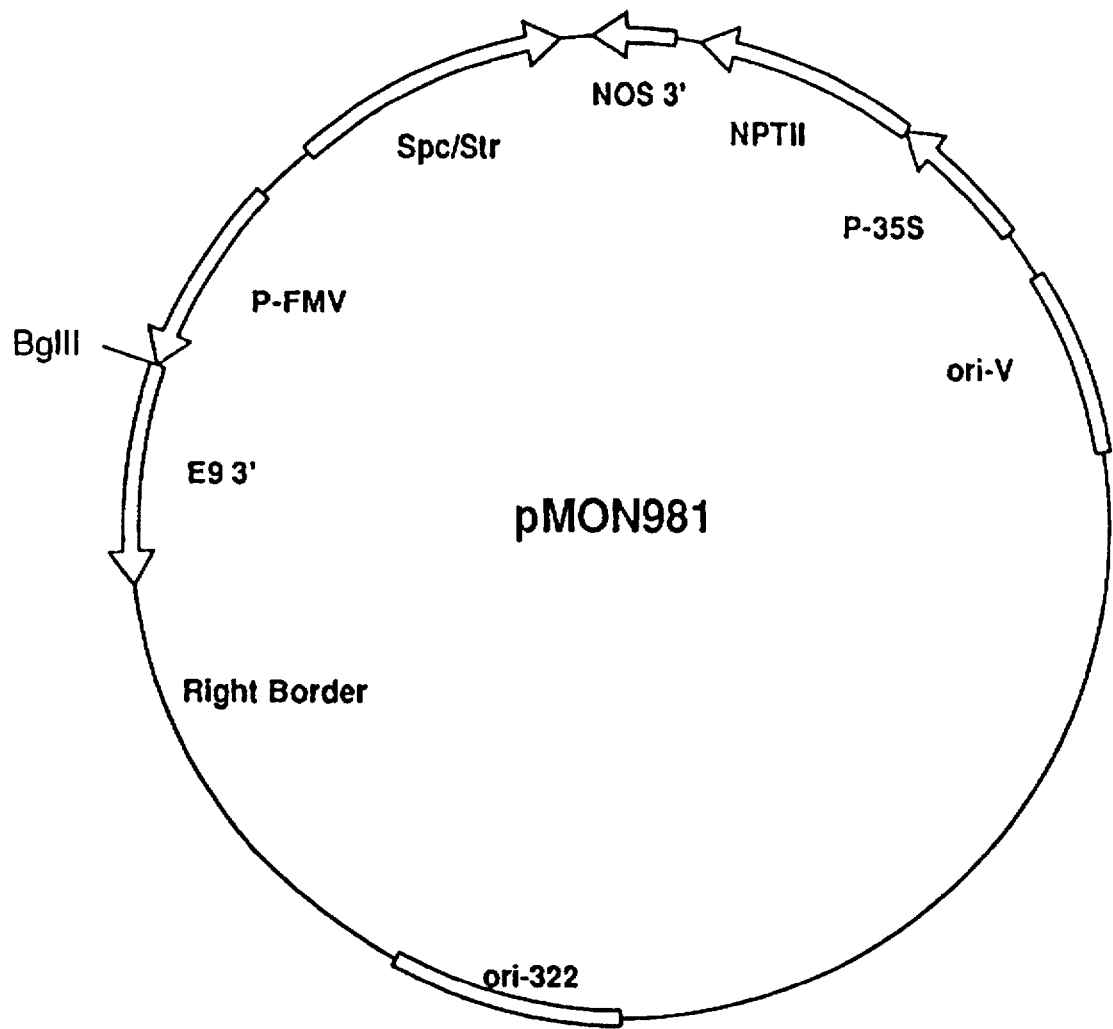
FIG. 10 illustrates a plasmid map of pMON981.
Figure 11:
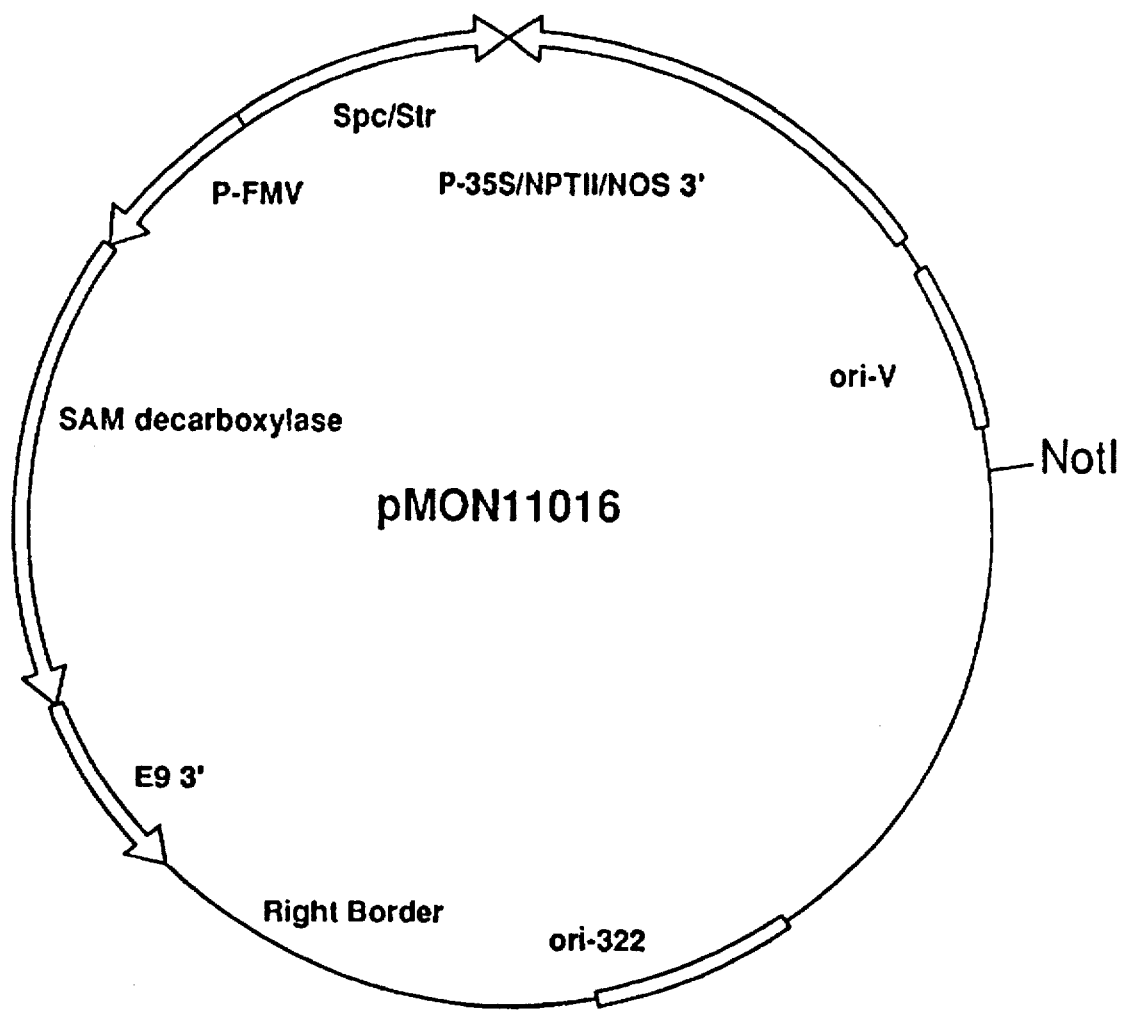
FIG. 11 illustrates a plasmid map of pMON11016.
Figure 12:
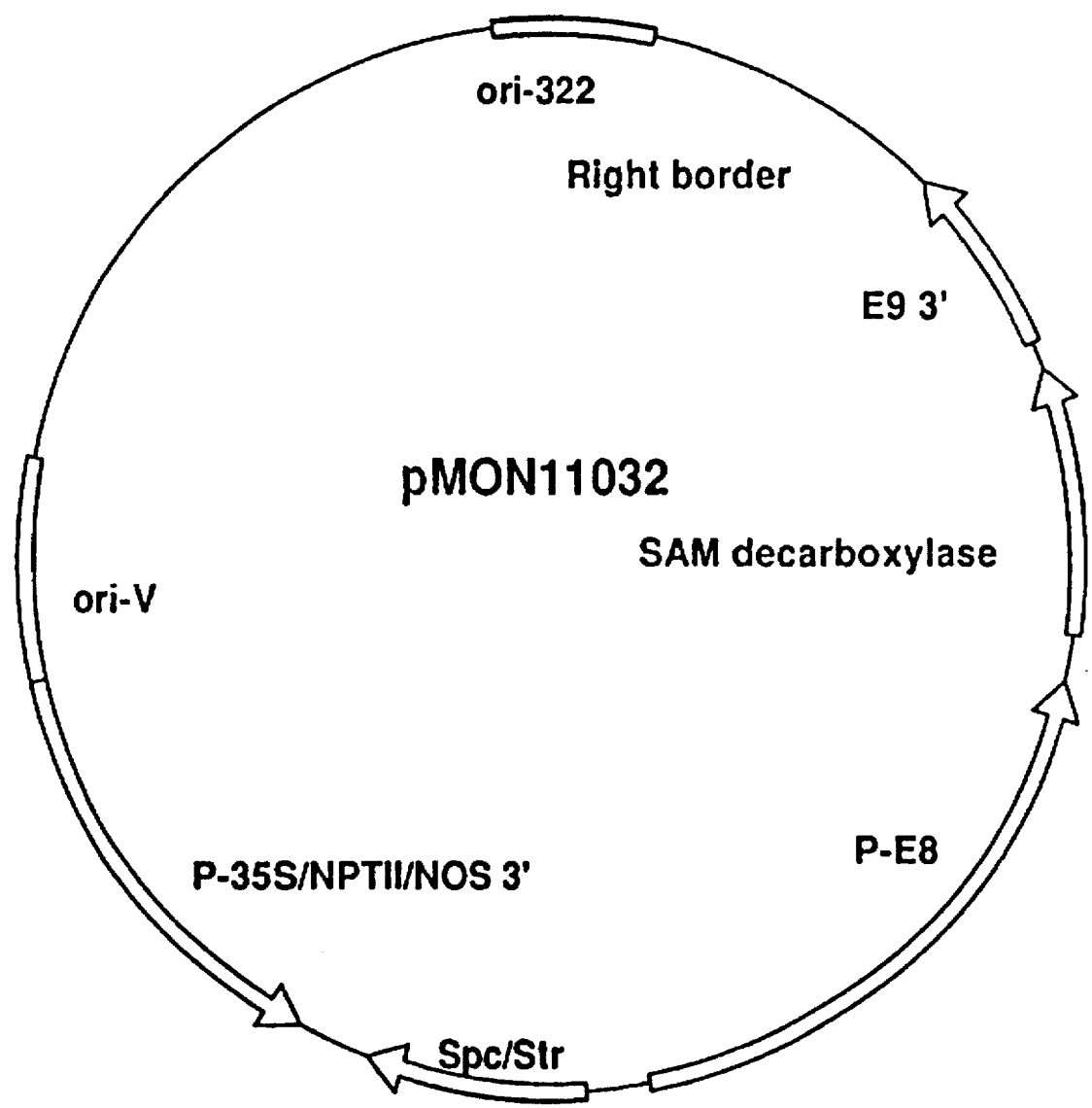
FIG. 12 illustrates a plasmid map of pMON11032.
Figure 13:
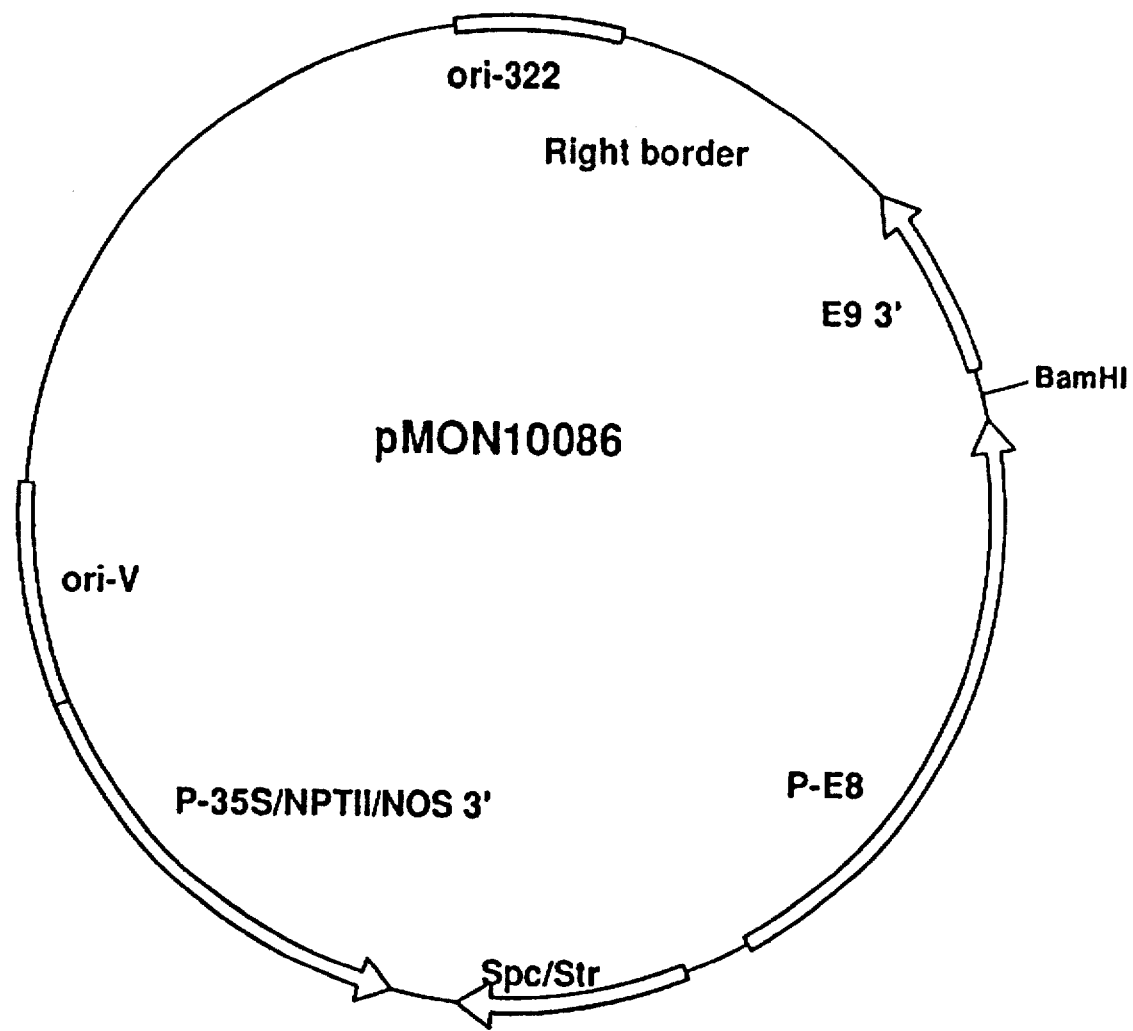
FIG. 13 illustrates a plasmid map of pMON10086.

The two primers used each introduced a BglII restriction site into the amplified DNA sequence to facilitate subsequent cloning steps. Following amplification, the DNA was cut with BglII and ligated with BglII cut pMON7258 (FIG. 8). The resultant plasmid, pMON11014 (FIG. 9), contained the SAM decarboxylase gene. The gene was subsequently cloned into plant transformation vectors that would permit expression of the gene under the control of either a constitutive promoter such as the full length transcript promoter from FMV or a fruit specific promoter such as the E8 promoter discussed above. The constitutive expression vector was constructed by cloning the pMON11014 BglII fragment containing SAM decarboxylase into BglII cut pMON981 (FIG. 10). The resulting plasmid, pMON11016 (FIG. 11), contained the gene in the correct orientation for expression in plants. The tissue specific expression vector, pMON11032 (FIG. 12), was constructed by insertion of the same BglII fragment from pMON11014 into BamHI cut pMON10086 (FIG. 13). Both transformation vectors were then introduced into Agrobacterium ABI using triparental mating. The Agrobacterium strains containing either pMON11016 or pMON11032 were then used to transform tomato plants as described above.

It is expected that plants expressing the ACC deaminase gene in combination with the SAM decarboxylase gene will inhibit synthesis of ethylene in plants, in a synergistic manner, such that the ripening or senescence process in the resulting plant is controlled to enhance the shelf life of the goods derived from the plant.

EXAMPLE 7

An ACC metabolizing enzyme such as ACC deaminase may also be used in combination with an antisense ACC synthase gene. The DNA sequence for ACC synthase is known (Van Der Straeten et al. 1990) (SEQ ID NO:8) and is presented in FIG. 16. Through routine manipulations, one can isolate a cDNA of the ACC synthase gene from a suitable cDNA library and prepare a vector containing the ACC synthase gene in an antisense orientation. This vector would contain the ACC synthase gene in an antisense direction and an ACC metabolizing enzyme such as ACC deaminase in addition with the other DNA fragments necessary for successful plant transformation. Preferably, both the antisense ACC synthase and the ACC deaminase are under the transcriptional control of a fruit specific promoter, such as E8.

The resulting transformed plants should significantly inhibit the production of ethylene in the fruit of the plant transformed. It is expected that the action of the ACC metabolizing enzyme in combination with the ACC synthase antisense gene will virtually eliminate ethylene synthesis and further delay ripening of the fruit. The fruit may be ripened at a desired time by exposure of the fruit to ambient ethylene.

EXAMPLE 8

This experiment was performed to evaluate the effect of reduction in ethylene levels in a plant when an ACC deaminase is expressed at high levels in the plant. Plant lines 5673 and 5854, as described in Example 3, were examined for ethylene generation in the plants and for phenotypic effects of expression of the ACC deaminase gene in the plant. Ethylene generation assays were performed on young leaf tissue from the plants by enclosing whole leaves or fruit in sealed containers and withdrawing 1.0 ml gas samples after one hour. Ethylene was quantified on a gas chromatograph (Ward et al. 1978) equipped with an alumina column and flame ionization detector. The results of ethylene generation assays are shown in Table 3 below.

TABLE 3

| Plant | Ethylene Synthesis (nl/g/h) | |
|---|---|---|
| | Leaf | Fruit |
| UC82B | 5.15 ± 0.69 | 11.73 ± 0.86 |
| UB82B-2 | 5.53 ± 0.37 | ND |
| 5673 | 0.60 ± 0.09 | 1.43 ± 0.36 |
| 5673-2 | 0.18 ± 02 | ND |
| 5854 | 1.14 ± 0.21 | ND |

(ND = not determined)

The ethylene level in plant line 5673 was reduced by 90% in one experiment utilizing young leaf tissue and by 97% in a second experiment. Plant line 5854 showed a reduction of approximately 78%. These data are consistent with the gene expression data in these plant lines. Line 5673 contained approximately 0.5% of the soluble protein as ACC deaminase while plant line 5854 contained approximately 0.05% of the soluble protein as ACC deaminase, as measured by protein gel blot analysis.

Protein gel blotting was performed by boiling protein samples for three minutes in the gel-loading buffer (50 mM TrisCl, pH 7, 100 mM dithiothreitol, 2% SDS, 10% glycerol, 0.1% bromophenol blue) and run on a 4–20% polyacrylamide MINIPROTEAN II ready gels (BIO-RAD). The protein was transferred to nitrocellulose membrane using a MilliBlot-SDE electroblotting apparatus (Millipore, Bedford, Mass.) following the manufacturers directions. The membrane was incubated overnight at 4° C. in 1% BSA, TBST (10 mM Tris, pH8, 150 mM NaCl, 0.05% Tween-20). The incubations were performed at room temperature with gentle agitation to hybridize the membrane. The primary ACC deaminase antibody was bound by incubating the membrane in a 1:1000 dilution of the goat serum in TBST for one hour. This was followed by three 10 minute washes in TBST. The secondary reagent was bound by incubating the membrane with 5 µC of $^{125}$I-labelled protein G in 20 ml of TBST for 30 minutes. The membrane was washed four times for 10 minutes with 0.1% Triton X-100 and exposed to film. Antibodies were obtained to the ACC deaminase protein by injecting a goat with 1.5 mg of protein and isolating antibodies from the goat pursuant to standard techniques known to those skilled in the art.

Figure 18:
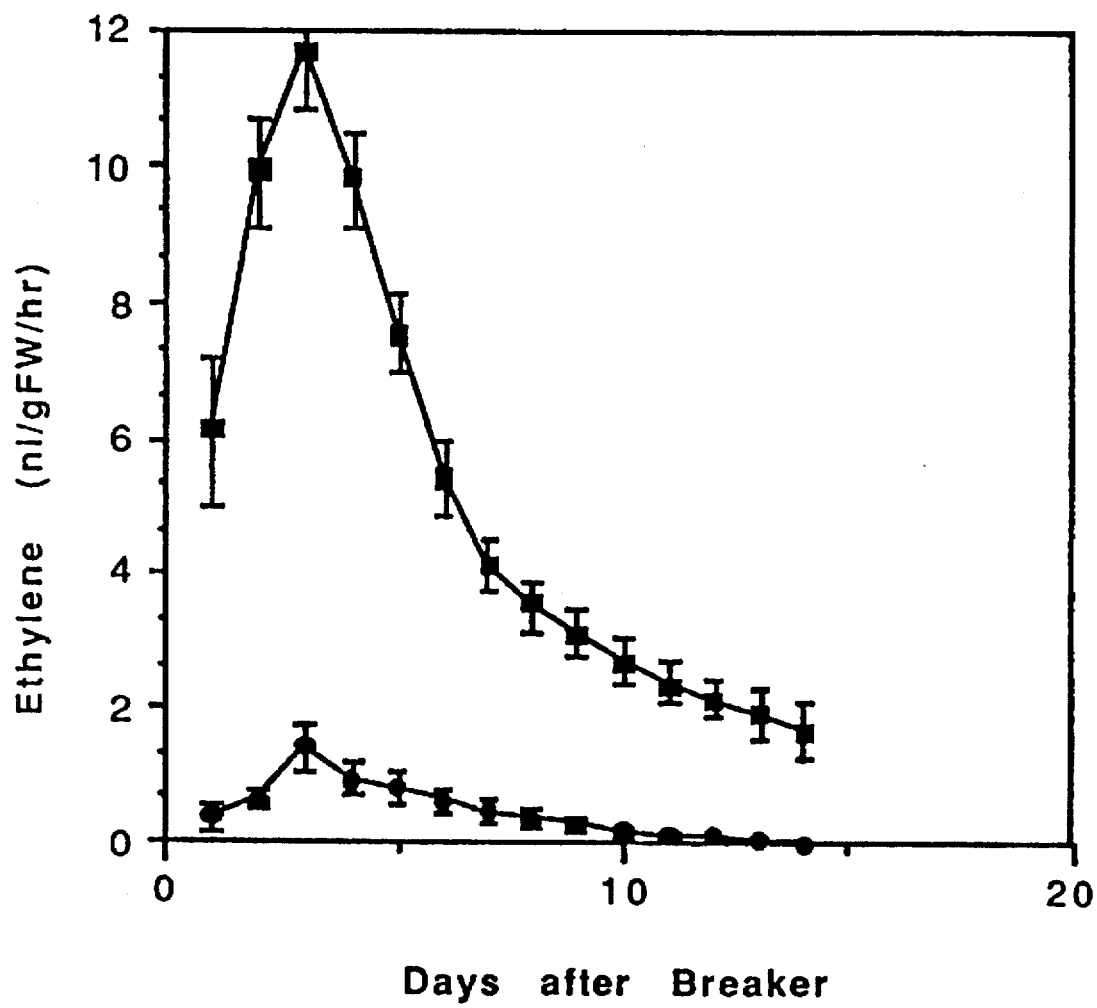
FIG. 18 illustrates graphically the relationship between the level of ethylene in control tomato fruit and transgenic tomato fruit expressing ACC deaminase.

Homozygous plants from plant line 5673 were also examined for phenotypic effects. Seed from the transgenic plants germinated normally, and plants were phenotypically indistinguishable from controls. The plants exhibited no delay in the onset of flowering or ripening. They did, however, show significant differences in the progression of ripening. The fruits of transgenic plants exhibited a peak of ethylene synthesis concomitant with control fruit, but at a level of only 10% that of controls. This is illustrated in FIG. 18. Ethylene generation by transgenic plants is represented by -●- and ethylene generation by control plants (UC82B) is represented by -■-. The bars represent means±standard error at specific time points. The fruit was detached at the breaker stage and ethylene generation measured daily as previously described. The delay in ripening of fruits detached at the breaker stage was also significant. Control fruit passed from breaker to fully red in seven days and exhibited a marked degree of softening after only two weeks. Transgenic tomato fruit reached the fully red stage after 24 days and remained firm for an extended period from the breaker stage. Fruit from transgenic plants remained firm for longer than 40 days and did not abscise while the control fruit had abscised after 14 days. These data are presented in Table 4.

TABLE 4

| Plant | Ripening Stage | | | |
|---|---|---|---|---|
| | 3 | 4 | 5 | 6 |
| Transgenic | 2.8 ± 0.53 | 5.3 ± 0.98 | 11.3 ± 3.1 | 23.5 ± 3.8 |
| Control | 1.4 ± 0.19 | 2.8 ± 0.26 | 5.1 ± 0.45 | 7.0 ± 0.53 |

The data in Table 4 are expressed as the number of days to reach a particular ripening stage after being detached, with a standard error. Ripening stages were defined as follows: Breaker, first sign of color change: 3, fully orange; 4, orange to red; 4, greater than 50% red; 6, fully red.

EXAMPLE 9

This example illustrates the expression of the ACC deaminase protein in a flowering plant species. The ACC deaminase gene was transformed into petunia plants. The petunia plants were transformed with a transformation vector that allows for the direct selection of transformed plants on glyphosate. Petunia explants were generally prepared for preculture as described for the tobacco plants in Example 1. Leaves from a one month old petunia plant were surface sterilized for fifteen minutes in a solution of 10% Clorox plus surfactant and washed three times with distilled water. The explants were cut in 0.5 cm squares, removing the leaf edges, mid-rib, tip, and petiole end for uniform tissue type. The explants were then placed in a single layer, upside down, on MS104 plates containing 2 mL 4COO5K media to moisten the surface and pre-cultured for 1–2 days. Explants were inoculated using an overnight culture of Agrobacterium containing the plant transformation vector that has been adjusted to a titer of $1.2 \times 10^9$ bacteria/mL with 4COO5K media. Explants were placed into a centrifuge tube, the Agrobacterium suspension was added and the mixture of bacteria and explants was "vortexed" on maximum setting for 25 seconds to insure even penetration of bacteria. The bacteria were poured off and the explants were blotted between layers of dry sterile filter paper to remove excess bacteria. The blotted explants were placed upside down on MS104 plates to which 2 mL 4COO5K media and a filter disk have been placed on top of the agar and co-cultured for two to three days. The explants were transferred to MS104 plates containing carbenicillin 1000 mg/l and cefotaxime at 100 mg/l for 3 days. The explants were then transferred to a new MS104 media that contains glyphosate at 0.05 mM, carbenicillin at 1000 mg/l and cefotaxime at 100 mg/l for the selection phase. At 4–6 weeks, shoots were cut from callus and placed on MSO and carbenicillin at 500 mg/l rooting media. Roots formed in 3–5 days, at which time leaf pieces were taken from rooted plates to confirm glysophate tolerance and that the material was transformed.

Figure 19:
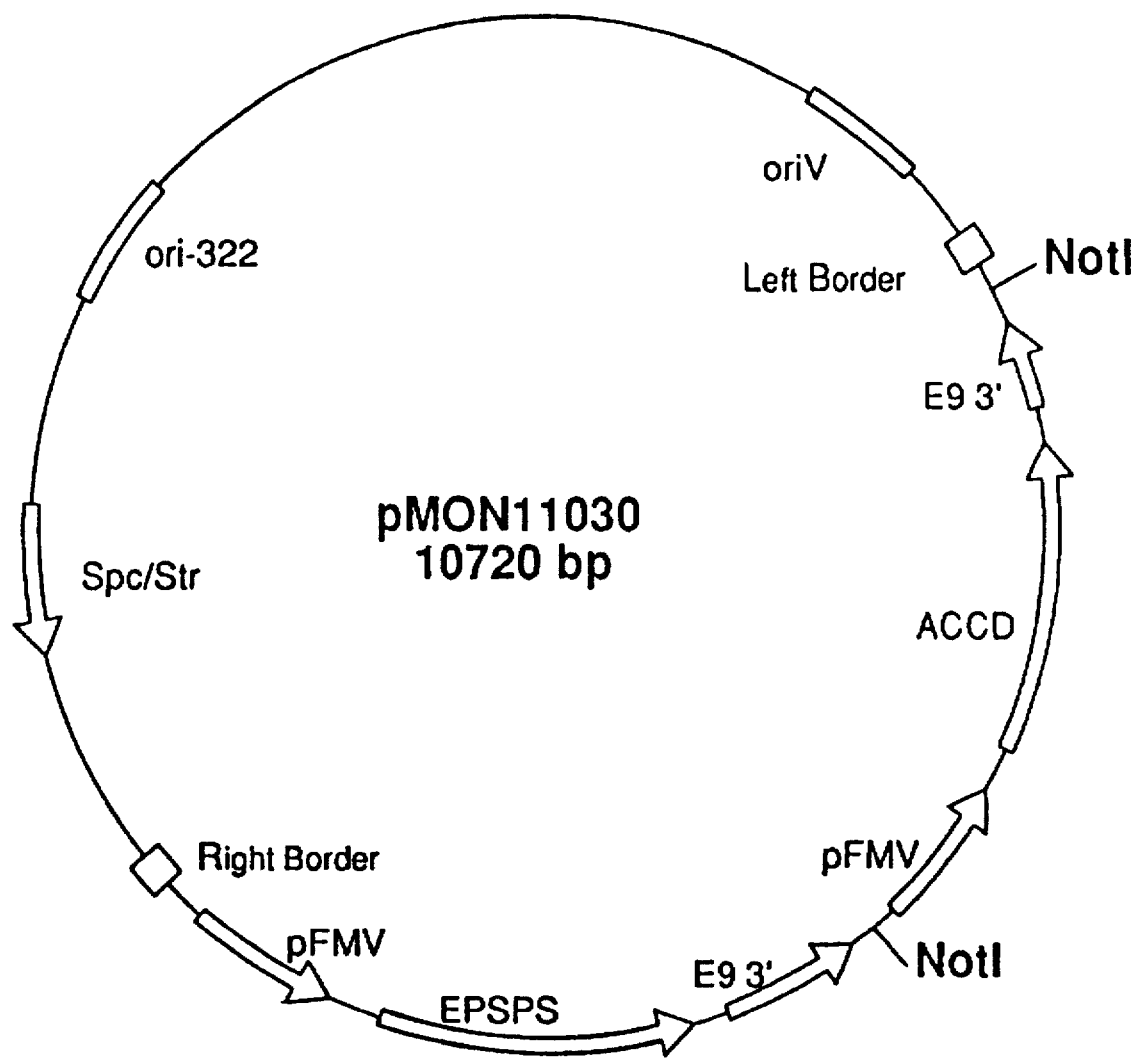
FIG. 19 illustrates a plasmid map of pMON11030.

The petunia plants were transformed with plant transformation vector pMON11030. A map of pMON11030 is presented in FIG. 19. This plasmid is essentially composed of the previously described bacterial replicon system that enables this plasmid to replicate in *E. coli* and to be introduced into and to replicate in Agrobacterium. Referring to FIG. 19, this plasmid additionally contains the bacterial spectinomycin-/streptomycin selectable marker gene (Spc/Str), and located between the T-DNA right border and left border is the CTP2-CP4 synthetic 5-enolpyruvyl-3-shikimate phosphate synthase (EPSPS) gene in the FMV35S promoter-E9 3' cassette. The CTP2-CP4 synthetic gene permits for selection of transformed cells by their ability to grow in the presence of glyphosate. The CTP2 is a chloroplast transit peptide and its DNA sequence is presented in FIG. 20 (SEQ ID NO:13). The DNA sequence of the CP4 EPSPS, a gene capable of conferring resistance to glyphosate, is presented in FIG. 21 (SEQ ID NO:14). The ACC deaminase gene from isolate 6G5 was placed between the FMV promoter and a hopaline synthase 3' region as a 2.0 kb NotI fragment into the unique NotI site to create pMON11037.

The presence of the ACC deaminase protein in transformed petunia tissues has been confirmed by immunoblot analysis of leaf discs as described in Example 8. ACC deaminase protein has been detected in leaf tissues in five out of six regenerated petunia plants.

Ethylene levels of transgenic petunia plants transformed with pMON11030 have also been determined in petunia plants expressing ACC deaminase. The level of ethylene in the plant is reduced to about one-half of the ethylene level in a control plant that has not been transformed. The results of ethylene generation assays are presented in Table 5 below.

TABLE 5

| ETHYLENE SYNTHESIS (nl/g/h) | |
|---|---|
| Plant Line | Leaf Tissue |
| 35861 | 0.58 |
| 35860 | 0.53 |
| 35862 | 0.62 |
| Control | 1.09 |

These data illustrate that transgenic plants expressing the ACC deaminase protein have reduced ethylene levels in leaf tissues. It is expected that such plants will show reduced senescence of flowers and leaves when compared to non-transformed plants.

All publications and patents mentioned in this specification are herein incorporated by reference as if each individual publication or patent was specifically and individually stated to be incorporated by reference.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

BIBLIOGRAPHY

Birnboim, H. C. and Doly, J. (1979) A rapid alkaline extraction procedure for screening recombinant plasmid DNA. Nucl. Acids. Res. 7:1513–1525.

Coruzzi, G., Broglie, R., Edwards, C., and Chua, N. H. (1984). Tissue-specific and light-regulated expression of a pea nuclear gene encoding the small subunit of ribulose-1, 5-bisphosphate carboxylase. EMBO J 3, 1671–1679.

Deikman, J. and Fischer, R. (1988). Interaction of a DNA binding factor with the 5'-flanking region of an ethylene-responsive fruit ripening gene from tomato. EMBO J. 7, 3315–3320.

de la Pena, A., Lorz, H. and Schell, J. (1987) Nature 325:274–276.

Ditta, G., Stanfield, S., Corbin, D., and Helinski, D. R. (1980). Broad host range DNA cloning system for Gram-Negative bacteria: construction of a gene bank of Rhizobium meliloti. Proc Natl Acad Sci U.S.A. 77, 7347–7351.

Drahos, D., Barry, G., Hemming, B., Brandt, F., Skipper, H., Kline, E., Kluepful, D., Hughes, T., and Gooden, D., in The Release of Genetically-Engineered Microorganisms. (1988). Sussman, M., Collins, C., Skinner, F. and Stewart-Tull, D. eds. Academic Press, New York.

Fling, M. E., Kopf, J., and Richards, C. (1985). Nucleotide sequence of the transposon Tn7 gene encoding an aminoglycoside-modifying enzyme, 3"(9)-O-nucleotidyltransferase. Nucleic Acids Research 13 no.19, 7095–7106.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L., and Woo, S. C. (1983). Expression of bacterial genes in plant cells. Proc Natl Acad Sci U.S.A. 80, 4803–4807.

Fraley, R. T., Rogers, S. G., Horsch, R. B., Eichholtz, D. A., Flick, J. S., Fink, C. L., Hoffmann, N. L., and Sanders, P. R. (1985). The SEV system: a new disarmed Ti plasmid vector system for plant transformation. Bio/Technology 3, 629–635.

Hamilton, A., Lycett, G. and Grierson, D. (1990). Antisense gene that inhibits synthesis of the hormone ethylene in transgenic plants. Nature 346:284–287.

Hohn, B. and Collins J. (1980) A small cosmid for efficient cloning of large DNA fragments. Gene 11: 291–298.

Holdsworth, M. Schuch, W. and Grierson, D. (1987). Nucleotide sequence of an ethylene-related gene from tomato. Nucleic Acids Res. 15:10600

Honma, M. and Shimomura, T. (1978). Metabolism of 1-Aminocyctopropane-1-carboxylic Acid. Agric, Biol. Chem. 42(10), pp 1825–1831.

Kay, R., Chan, A., Daly, M., and McPherson, J. (1987). Duplication of the CaMV 35S promoter sequence creates a strong enhancer for plants. Science 236, 1299–1302.

Klein, T. M., Wold, E. D., Wu, R. and Sanford, J. C. (1987) Nature 27:70–73.

Koncz, C., and Schell, J. (1986). The promoter of TL-DNA gene 5 controls the tissue-specific expression of chimeric genes carried by novel type of Agrobacterium binary vector. Mol Gen Genet 204, 383–396.

Lincoln, J. and Fischer, R. (1988). Diverse mechanisms for the regulation of ethylene-inducible gene expression. Mol Gen Genet 212, 71–75.

McCabe, D. E., et al. (1988) Bio/Technology 6:923.

Miller, J. H. (1972). Experiments in Molecular Genetics. Cold Spring Harbor Laboratory, Cold Spring Harbor, N.Y.

Miller, L. T. (1982). Single derivatization method for routine analysis of bacterial whole-cell fatty acid methyl esters, including hydroxy acids. J. Clinical Microbiology 16:584–586.

Morelli, G., Nagy, F., Fraley, R. T., Rogers, S. G., and Chua, N. H. (1985). A short conserved sequence is involved in the light-inducibility of a gene encoding ribulose 1,5-bisphosphate carboxylase small subunit of pea. Nature 315, 200–204.

Neuhaus, G. et al. (1987) Theor. Appl. Genet. 75:30.

Odell, J. T., Nagy, F., and Chua, N. H. (1985). Identification of DNA sequences required for activity of the cauliflower mosaic virus 35S promoter. Nature 313, 810–812.

Sambrook, J., Fritsch, E. F., and Maniatis, T. (1989) Molecular Cloning: A Laboratory Manual—second edition. Cold Spring Harbor Laboratory Press, Cold Spring Harbor, N.Y.

Stalker, D. M., Thomas, C. M., and Helinski, D. R. (1981). Nucleotide sequence of the region of the origin of replication of the broad host range plasmid RK2. Mol Gen Genet 181, 8–12.

Tabor, S., and Richardson, C. C. (1985). A bacteriophage T7 RNA polymerase/promoter system for controlled expression of specific genes. Proc. Natl. Acad. Sci. U.S.A. 82, 1074–1078.

Tabor, C. and Tabor H. 1987. The speEspeD operon of E. coli. J. Biol. Chem. 262:16037–16040.

Talmadge, K., and Gilbert, W., "Construction of plasmid vectors with unique PstI cloning sites in the signal sequence coding region" Gene, (12) 235–241 (1980).

Van Der Straeten, D., Van Wiemeersch, L., Goodman, H. and Van Montagu, M. (1990) Proc. Natl. Acad. Sci. U.S.A. 87:4859–4863.

Vieira, J. and Messing, J., Production of single-stranded plasmid DNA. Methods. Enzymol. 153:3 (1987).

Ward, T., Wright, M., Roberts, J., Serf, R., and Osborne, D. (1978) Analytical procedures for the assay and identification of ethylene. In Isolation of plant growth substances, J. Hillman, ed. (Cambridge: Cambridge University Press), pp. 135–151.

---

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 1079 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
GATATCCCAT ATCAAGGAGC AGAGTC ATG AAT CTG AAT CGT TTT GAA CGT TAT            53
                              Met Asn Leu Asn Arg Phe Glu Arg Tyr
                               1                   5

CCA TTG ACC TTC GGT CCT TCT CCC ATC ACG CCC TTG AAG CGC CTC AGT           101
Pro Leu Thr Phe Gly Pro Ser Pro Ile Thr Pro Leu Lys Arg Leu Ser
 10              15                  20                      25

CAA CAT CTG GGG GGC AAG GTC GAG CTG TAT GCC AAA CGT GAA GAC TGC           149
Gln His Leu Gly Gly Lys Val Glu Leu Tyr Ala Lys Arg Glu Asp Cys
                 30                  35                  40

AAC AGT GGC CTG GCC TTT GGT GGG AAC AAG ACG CGC AAG CTC GAA TAC           197
Asn Ser Gly Leu Ala Phe Gly Gly Asn Lys Thr Arg Lys Leu Glu Tyr
             45                  50                  55

CTC ATT CCC GAA GCG ATC GAG CAA GGC TGC GAT ACG CTG GTT TCC ATC           245
Leu Ile Pro Glu Ala Ile Glu Gln Gly Cys Asp Thr Leu Val Ser Ile
         60                  65                  70

GGC GGC ATC CAG TCG AAC CAG ACC CGT CAG GTC GCT GCC GTC GCT GCC           293
Gly Gly Ile Gln Ser Asn Gln Thr Arg Gln Val Ala Ala Val Ala Ala
     75                  80                      85

CAC TTG GGC ATG AAG TGC GTG TTG GTG CAG GAA AAC TGG GTG AAC TAT           341
His Leu Gly Met Lys Cys Val Leu Val Gln Glu Asn Trp Val Asn Tyr
 90                  95                 100                 105

TCC GAC GCG GTG TAT GAC CGC GTA GGC AAC ATC GAG ATG TCG CGG ATC           389
Ser Asp Ala Val Tyr Asp Arg Val Gly Asn Ile Glu Met Ser Arg Ile
                 110                 115                 120

ATG GGC GCT GAT GTG CGG CTT GAC GCC GCT GGC TTC GAT ATT GGC ATT           437
Met Gly Ala Asp Val Arg Leu Asp Ala Ala Gly Phe Asp Ile Gly Ile
             125                 130                 135

CGG CCA AGT TGG GAA AAG GCC ATG AGC GAT GTC GTG GAA CAG GGT GGC           485
Arg Pro Ser Trp Glu Lys Ala Met Ser Asp Val Val Glu Gln Gly Gly
         140                 145                 150

AAA CCG TTT CCG ATT CCA GCG GGT TGC TCC GAG CAT CCC TAT GGC GGC           533
```

```
Lys Pro Phe Pro Ile Pro Ala Gly Cys Ser Glu His Pro Tyr Gly Gly
    155             160                 165

CTC GGT TTC GTC GGC TTT GCC GAA GAG GTG CGG CAG CAG GAA AAG GAA    581
Leu Gly Phe Val Gly Phe Ala Glu Glu Val Arg Gln Gln Glu Lys Glu
170                 175                 180                 185

CTG GGC TTC AAG TTT GAC TAC ATC GTG GTC TGC TCG GTG ACC GGC AGT    629
Leu Gly Phe Lys Phe Asp Tyr Ile Val Val Cys Ser Val Thr Gly Ser
                190                 195                 200

ACG CAG GCG GGC ATG GTT GTT GGT TTC GCG GCT GAC GGT CGT TCG AAG    677
Thr Gln Ala Gly Met Val Val Gly Phe Ala Ala Asp Gly Arg Ser Lys
            205                 210                 215

AAT GTG ATT GGT ATC GAT GCT TCG GCC AAG CCG GAA CAG ACC AAG GCA    725
Asn Val Ile Gly Ile Asp Ala Ser Ala Lys Pro Glu Gln Thr Lys Ala
        220                 225                 230

CAG ATC CTG CGC ATC GCC CGA CAC ACC GCT GAG TTG GTG GAG TTG GGG    773
Gln Ile Leu Arg Ile Ala Arg His Thr Ala Glu Leu Val Glu Leu Gly
    235                 240                 245

CGC GAG ATT ACG GAA GAG GAC GTG GTG CTC GAT ACG CGT TTT GCC TAC    821
Arg Glu Ile Thr Glu Glu Asp Val Val Leu Asp Thr Arg Phe Ala Tyr
250                 255                 260                 265

CCG GAA TAT GGC TTG CCC AAC GAA GGC ACA TTG GAA GCC ATC CGA CTG    869
Pro Glu Tyr Gly Leu Pro Asn Glu Gly Thr Leu Glu Ala Ile Arg Leu
                270                 275                 280

TGC GGC AGC CTT GAA GGC GTG CTG ACA GAC CCG GTA TAT GAA GGT AAA    917
Cys Gly Ser Leu Glu Gly Val Leu Thr Asp Pro Val Tyr Glu Gly Lys
            285                 290                 295

TCG ATG CAC GGC ATG ATT GAA ATG GTC CGT CGT GGT GAA TTC CCC GAA    965
Ser Met His Gly Met Ile Glu Met Val Arg Arg Gly Glu Phe Pro Glu
        300                 305                 310

GGT TCC AAA GTG CTT TAC GCA CAC TTG GGT GGG GCG CCG GCG CTG AAC   1013
Gly Ser Lys Val Leu Tyr Ala His Leu Gly Gly Ala Pro Ala Leu Asn
    315                 320                 325

GCC TAC AGC TTC CTG TTT CGT AAC GGC TAAGCGTAGA ACTGCTTTTG         1060
Ala Tyr Ser Phe Leu Phe Arg Asn Gly
330                 335

GAGTCATCTG TGGGAGCTC                                              1079
```

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GAAGGAAGCT TCACGAAATC GGCCCTTATT C                                       31

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

GGGGCTTTAG ATCTTCTTTT GCACTGTGAA TG                                    32

( 2 ) INFORMATION FOR SEQ ID NO:4:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:4:

GGTGAACCAT GGAATTCCAC ATG                    23

( 2 ) INFORMATION FOR SEQ ID NO:5:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:5:

GCAATTGGAT CCCTTTCCAT AGC                    23

( 2 ) INFORMATION FOR SEQ ID NO:6:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:6:

GGAGAAGATA AGATCTATGA AAAAACTGAA ACTGC        35

( 2 ) INFORMATION FOR SEQ ID NO:7:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:7:

GCAGAAGTAA ATAGATCTGG CGGAGCC                 27

( 2 ) INFORMATION FOR SEQ ID NO:8:

( i ) SEQUENCE CHARACTERISTICS:
    ( A ) LENGTH: 1800 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:8:

CCAAACACAT AATACTTTTA ATACAATTAG TTATTTATTA GAAGTATTTA AAGTAAAGCA    60

CTTGTGAGTT GTGTACATTT TATTAATCTT CATCTTCTTA ATTCTCTTCA GTTTTAATT    120

TCTTCACTTC TAAACTCATT TAGTAAAAAA AAA ATG GGA TTT GAG ATT GCA AAG   174
                                    Met Gly Phe Glu Ile Ala Lys
                                     1               5

| | | | | | | | | | | | | | | | | |
|---|---|---|---|---|---|---|---|---|---|---|---|---|---|---|---|---|
| ACC | AAC | TCA | ATC | TTA | TCA | AAA | TTG | GCT | ACT | AAT | GAA | GAG | CAT | GGC | GAA | 222 |
| Thr | Asn | Ser | Ile | Leu | Ser | Lys | Leu | Ala | Thr | Asn | Glu | Glu | His | Gly | Glu | |
| | | 10 | | | | 15 | | | | | 20 | | | | | |
| AAC | TCG | CCA | TAT | TTT | GAT | GGG | TGG | AAA | GCA | TAC | GAT | AGT | GAT | CCT | TTC | 270 |
| Asn | Ser | Pro | Tyr | Phe | Asp | Gly | Trp | Lys | Ala | Tyr | Asp | Ser | Asp | Pro | Phe | |
| | 25 | | | | | 30 | | | | 35 | | | | | | |
| CAC | CCT | CTA | AAA | AAC | CCC | AAC | GGA | GTT | ATC | CAA | ATG | GGT | CTT | GCT | GAA | 318 |
| His | Pro | Leu | Lys | Asn | Pro | Asn | Gly | Val | Ile | Gln | Met | Gly | Leu | Ala | Glu | |
| 40 | | | | | 45 | | | | 50 | | | | | | 55 | |
| AAT | CAG | CTT | TGT | TTA | GAC | TTG | ATA | GAA | GAT | TGG | ATT | AAG | AGA | AAC | CCA | 366 |
| Asn | Gln | Leu | Cys | Leu | Asp | Leu | Ile | Glu | Asp | Trp | Ile | Lys | Arg | Asn | Pro | |
| | | | | 60 | | | | | 65 | | | | | 70 | | |
| AAA | GGT | TCA | ATT | TGT | TCT | GAA | GGA | ATC | AAA | TCA | TTC | AAG | GCC | ATT | GCC | 414 |
| Lys | Gly | Ser | Ile | Cys | Ser | Glu | Gly | Ile | Lys | Ser | Phe | Lys | Ala | Ile | Ala | |
| | | | 75 | | | | | 80 | | | | | 85 | | | |
| AAC | TTT | CAA | GAT | TAT | CAT | GGC | TTG | CCT | GAA | TTC | AGA | AAA | GCG | ATT | GCG | 462 |
| Asn | Phe | Gln | Asp | Tyr | His | Gly | Leu | Pro | Glu | Phe | Arg | Lys | Ala | Ile | Ala | |
| | | 90 | | | | | 95 | | | | | 100 | | | | |
| AAA | TTT | ATG | GAG | AAA | ACA | AGA | GGA | GGA | AGA | GTT | AGA | TTT | GAT | CCA | GAA | 510 |
| Lys | Phe | Met | Glu | Lys | Thr | Arg | Gly | Gly | Arg | Val | Arg | Phe | Asp | Pro | Glu | |
| | 105 | | | | | 110 | | | | | 115 | | | | | |
| AGA | GTT | GTT | ATG | GCT | GGT | GGT | GCC | ACT | GGA | GCT | AAT | GAG | ACA | ATT | ATA | 558 |
| Arg | Val | Val | Met | Ala | Gly | Gly | Ala | Thr | Gly | Ala | Asn | Glu | Thr | Ile | Ile | |
| 120 | | | | | 125 | | | | | 130 | | | | | 135 | |
| TTT | TGT | TTG | GCT | GAT | CCT | GGC | GAT | GCA | TTT | TTA | GTA | CCT | TCA | CCA | TAC | 606 |
| Phe | Cys | Leu | Ala | Asp | Pro | Gly | Asp | Ala | Phe | Leu | Val | Pro | Ser | Pro | Tyr | |
| | | | | 140 | | | | | 145 | | | | | 150 | | |
| TAC | CCA | GCA | TTT | AAC | AGA | GAT | TTA | AGA | TGG | AGA | ACT | GGA | GTA | CAA | CTT | 654 |
| Tyr | Pro | Ala | Phe | Asn | Arg | Asp | Leu | Arg | Trp | Arg | Thr | Gly | Val | Gln | Leu | |
| | | | 155 | | | | | 160 | | | | | 165 | | | |
| ATT | CCA | ATT | CAC | TGT | GAG | AGC | TCC | AAT | AAT | TTC | AAA | ATT | ACT | TCA | AAA | 702 |
| Ile | Pro | Ile | His | Cys | Glu | Ser | Ser | Asn | Asn | Phe | Lys | Ile | Thr | Ser | Lys | |
| | | 170 | | | | | 175 | | | | | 180 | | | | |
| GCA | GTA | AAA | GAA | GCA | TAT | GAA | AAT | GCA | CAA | AAA | TCA | AAC | ATC | AAA | GTA | 750 |
| Ala | Val | Lys | Glu | Ala | Tyr | Glu | Asn | Ala | Gln | Lys | Ser | Asn | Ile | Lys | Val | |
| | 185 | | | | | 190 | | | | | 195 | | | | | |
| AAA | GGT | TTG | ATT | TTG | ACC | AAT | CCA | TCA | AAT | CCA | TTG | GGC | ACC | ACT | TTG | 798 |
| Lys | Gly | Leu | Ile | Leu | Thr | Asn | Pro | Ser | Asn | Pro | Leu | Gly | Thr | Thr | Leu | |
| 200 | | | | | 205 | | | | | 210 | | | | | 215 | |
| GAC | AAA | GAC | ACA | CTG | AAA | AGT | GTC | TTG | AGT | TTC | ACC | AAC | CAA | CAC | AAC | 846 |
| Asp | Lys | Asp | Thr | Leu | Lys | Ser | Val | Leu | Ser | Phe | Thr | Asn | Gln | His | Asn | |
| | | | | 220 | | | | | 225 | | | | | 230 | | |
| ATC | CAC | CTT | GTT | TGT | GAC | GAA | ATC | TAC | GCA | GCC | ACT | GTC | TTT | GAC | ACG | 894 |
| Ile | His | Leu | Val | Cys | Asp | Glu | Ile | Tyr | Ala | Ala | Thr | Val | Phe | Asp | Thr | |
| | | | 235 | | | | | 240 | | | | | 245 | | | |
| CCT | CAA | TTC | GTC | AGT | ATA | GCT | GAA | ATC | CTC | GAT | GAA | CAG | GAA | ATG | ACT | 942 |
| Pro | Gln | Phe | Val | Ser | Ile | Ala | Glu | Ile | Leu | Asp | Glu | Gln | Glu | Met | Thr | |
| | | 250 | | | | | 255 | | | | | 260 | | | | |
| TAC | TGC | AAC | AAA | GAT | TTA | GTT | CAC | ATC | GTC | TAC | AGT | CTT | TCA | AAA | GAC | 990 |
| Tyr | Cys | Asn | Lys | Asp | Leu | Val | His | Ile | Val | Tyr | Ser | Leu | Ser | Lys | Asp | |
| | 265 | | | | | 270 | | | | | 275 | | | | | |
| ATG | GGG | TTA | CCA | GGA | TTT | AGA | GTC | GGA | ATC | ATA | TAT | TCT | TTT | AAC | GAC | 1038 |
| Met | Gly | Leu | Pro | Gly | Phe | Arg | Val | Gly | Ile | Ile | Tyr | Ser | Phe | Asn | Asp | |
| 280 | | | | | 285 | | | | | 290 | | | | | 295 | |
| GAT | GTC | GTT | AAT | TGT | GCT | AGA | AAA | ATG | TCG | AGT | TTC | GGT | TTA | GTA | TCT | 1086 |
| Asp | Val | Val | Asn | Cys | Ala | Arg | Lys | Met | Ser | Ser | Phe | Gly | Leu | Val | Ser | |
| | | | | 300 | | | | | 305 | | | | | 310 | | |
| ACA | CAA | ACG | CAA | TAT | TTT | TTA | GCG | GCA | ATG | CCA | TCG | GAC | GAA | AAA | TTC | 1134 |
| Thr | Gln | Thr | Gln | Tyr | Phe | Leu | Ala | Ala | Met | Pro | Ser | Asp | Glu | Lys | Phe | |
| | | | 315 | | | | | 320 | | | | | 325 | | | |

```
GTC GAT AAT TTT CTA AGA GAA AGC GCG ATG AGG TTA GGT AAA AGG CAC      1182
Val Asp Asn Phe Leu Arg Glu Ser Ala Met Arg Leu Gly Lys Arg His
        330                 335                 340

AAA CAT TTT ACT AAT GGA CTT GAA GTA GTG GGA ATT AAA TGC TTG AAA      1230
Lys His Phe Thr Asn Gly Leu Glu Val Val Gly Ile Lys Cys Leu Lys
    345                 350                 355

AAT AAT GCG GGG CTT TTT TGT TGG ATG GAT TTG CGT CCA CTT TTA AGG      1278
Asn Asn Ala Gly Leu Phe Cys Trp Met Asp Leu Arg Pro Leu Leu Arg
360                 365                 370                 375

GAA TCG ACT TTC GAT AGC GAA ATG TCG TTA TGG AGA GTT ATT ATA AAC      1326
Glu Ser Thr Phe Asp Ser Glu Met Ser Leu Trp Arg Val Ile Ile Asn
                380                 385                 390

GAT GTT AAG CTT AAC GTC TCG CTT GGA TCT TCG TTT GAA TGT CAA GAG      1374
Asp Val Lys Leu Asn Val Ser Leu Gly Ser Ser Phe Glu Cys Gln Glu
            395                 400                 405

CCA GGG TGG TTC CGA GTT TGT TTT GCA AAT ATG GAT GAT GGA ACG GTT      1422
Pro Gly Trp Phe Arg Val Cys Phe Ala Asn Met Asp Asp Gly Thr Val
        410                 415                 420

GAT ATT GCG CTC GCG AGG ATT CGG AGG TTC GTA GGT GTT GAG AAA AGT      1470
Asp Ile Ala Leu Ala Arg Ile Arg Arg Phe Val Gly Val Glu Lys Ser
    425                 430                 435

GGA GAT AAA TCG AGT TCG ATG GAA AAG AAG CAA CAA TGG AAG AAG AAT      1518
Gly Asp Lys Ser Ser Ser Met Glu Lys Lys Gln Gln Trp Lys Lys Asn
440                 445                 450                 455

AAT TTG AGA CTT AGT TTT TCG AAA AGA ATG TAT GAT GAA AGT GTT TTG      1566
Asn Leu Arg Leu Ser Phe Ser Lys Arg Met Tyr Asp Glu Ser Val Leu
                460                 465                 470

TCA CCA CTT TCG TCA CCT ATT CCT CCC TCA CCA TTA GTT CGT              1608
Ser Pro Leu Ser Ser Pro Ile Pro Pro Ser Pro Leu Val Arg
            475                 480                 485

TAAGACTTAA TTAAAAGGGA AGAATTTAAT TTATGTTTTT TTATATTTTG AAAAAAATTT    1668

GTAAGAATAA GATTATAATA GGAAAAGAAA ATAAGTATGT AGGATGAGGA GTATTTCAG     1728

AAATAGTTGT TAGCGTATGT ATTGACAACT GGTCTATGTA CTTAGACATC ATAATTTGTC    1788

TTAGCTAATT AA                                                        1800
```

( 2 ) INFORMATION FOR SEQ ID NO:9:

( i ) SEQUENCE CHARACTERISTICS:
        ( A ) LENGTH: 900 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

```
ACAGCCGTCC TAAGGAGAAG ATAAGATCT ATG AAA AAA CTG AAA CTG CAT GGC      53
                                Met Lys Lys Leu Lys Leu His Gly
                                  1               5

TTT AAT AAT CTG ACC AAA AGT CTG AGT TTT TGT ATT TAC GAT ATC TGC      101
Phe Asn Asn Leu Thr Lys Ser Leu Ser Phe Cys Ile Tyr Asp Ile Cys
        10                  15                  20

TAC GCC AAA ACT GCC GAA GAG CGC GAC GGT TAT ATT GCT TAT ATC GAT      149
Tyr Ala Lys Thr Ala Glu Glu Arg Asp Gly Tyr Ile Ala Tyr Ile Asp
    25                  30                  35                  40

GAA CTC TAT AAT GCC AAC CGT CTG ACC GAA ATC CTG TCA GAA ACC TGT      197
Glu Leu Tyr Asn Ala Asn Arg Leu Thr Glu Ile Leu Ser Glu Thr Cys
                45                  50                  55

TCC ATT ATC GGG GCT AAT ATT CTT AAC ATC GCC CGC CAG GAT TAC GAA      245
Ser Ile Ile Gly Ala Asn Ile Leu Asn Ile Ala Arg Gln Asp Tyr Glu
            60                  65                  70
```

```
CCA CAG GGT GCC AGC GTC ACT ATT CTG GTG AGT GAA GAA CCG GTT GAC     293
Pro Gln Gly Ala Ser Val Thr Ile Leu Val Ser Glu Glu Pro Val Asp
        75                  80                  85

CCG AAA CTC ATC GAC AAA ACA GAA CAC CCC GGC CCA CTG CCA GAA ACG     341
Pro Lys Leu Ile Asp Lys Thr Glu His Pro Gly Pro Leu Pro Glu Thr
        90                  95                  100

GTC GTT GCC CAT CTT GAT AAA AGT CAT ATT TGC GTA CAT ACC TAC CCG     389
Val Val Ala His Leu Asp Lys Ser His Ile Cys Val His Thr Tyr Pro
105                 110                 115                 120

GAA AGT CAT CCT GAA GGC GGT TTA TGT ACC TTC CGC GCC GAT ATT GAA     437
Glu Ser His Pro Glu Gly Gly Leu Cys Thr Phe Arg Ala Asp Ile Glu
                    125                 130                 135

GTC TCT ACC TGC GGC GTG ATT TCT CCG CTG AAG GCG CTG AAT TAC CTG     485
Val Ser Thr Cys Gly Val Ile Ser Pro Leu Lys Ala Leu Asn Tyr Leu
        140                 145                 150

ATC CAC CAG CTT GAG TCC GAT ATC GTA ACC ATT GAT TAT CGC GTG CGC     533
Ile His Gln Leu Glu Ser Asp Ile Val Thr Ile Asp Tyr Arg Val Arg
        155                 160                 165

GGT TTT ACC CGC GAC ATT AAC GGT ATG AAG CAC TTT ATC GAC CAT GAG     581
Gly Phe Thr Arg Asp Ile Asn Gly Met Lys His Phe Ile Asp His Glu
170                 175                 180

ATT AAT TCG ATT CAG AAC TTT ATG TCT GAC GAT ATG AAG GCG CTG TAT     629
Ile Asn Ser Ile Gln Asn Phe Met Ser Asp Asp Met Lys Ala Leu Tyr
185                 190                 195                 200

GAC ATG GTG GAT GTG AAC GTC TAT CAG GAA AAT ATC TTC CAT ACC AAG     677
Asp Met Val Asp Val Asn Val Tyr Gln Glu Asn Ile Phe His Thr Lys
                    205                 210                 215

ATG TTG CTT AAA GAG TTC GAC CTT AAG CAC TAC ATG TTC CAC ACC AAA     725
Met Leu Leu Lys Glu Phe Asp Leu Lys His Tyr Met Phe His Thr Lys
        220                 225                 230

CCG GAA GAC TTA ACC GAC AGC GAG CGC CAG GAA ATT ACC GCT GCG CTG     773
Pro Glu Asp Leu Thr Asp Ser Glu Arg Gln Glu Ile Thr Ala Ala Leu
        235                 240                 245

TGG AAA GAA ATG CGC GAG ATT TAT TAC GGG CGC AAT ATG CCA GCT GTT     821
Trp Lys Glu Met Arg Glu Ile Tyr Tyr Gly Arg Asn Met Pro Ala Val
250                 255                 260

TAACGGCTCT GGCGGAGCTC CCAGGCTCCG CCAGATCTAT TTACTTCTGC TGCACGAAAT    881

TGCGGTAAGC CGCCACGAC                                                  900
```

(2) INFORMATION FOR SEQ ID NO:10:

(i) SEQUENCE CHARACTERISTICS:
      (A) LENGTH: 1138 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:10:

```
CTAGAAGGAA GCTTCACGAA ATCGGCCCTT ATTCAAAAAT AACTTTTAAA TAATGAATTT     60

TAAATTTTAA GAAATAATAT CCAATGAATA AATGACATGT AGCATTTTAC CTAAATATTT    120

CAACTATTTT AATCCAATAT TAATTTGTTT TATTCCCAAC AATAGAAAGT CTTGTGCAGA    180

CATTTAATCT GACTTTTCCA GTACTAAATA TTAATTTTCT GAAGATTTTC GGGTTTAGTC    240

CACAAGTTTT AGTGAGAAGT TTGCTCAAA ATTTTAGGTG AGAAGGTTTG ATATTTATCT    300

TTTGTTAAAT TAATTTATCT AGGTGACTAT TATTTATTTA AGTAGAAATT CATATCATTA    360

CTTTTGCCAA CTTGTAGTCA TAATAGGAGT AGGTGTATAT GATGAAGGAA TAAACAAGTT    420
```

-continued

| | | | | | |
|---|---|---|---|---|---|
| CAGTGAAGTG | ATTAAAATAA | AATATAATTT | AGGTGTACAT | CAAATAAAAA | CCTTAAAGTT | 480 |
| TAGAAAGGCA | CCGAATAATT | TTGCATAGAA | GATATTAGTA | AATTTATAAA | AATAAAAGAA | 540 |
| ATGTAGTTGT | CAAGTTGTCT | TCTTTTTTTT | GGATAAAAAT | AGCAGTTGGC | TTATGTCATT | 600 |
| CTTTTACAAC | CTCCATGCCA | CTTGTCCAAT | TGTTGACACT | TAACTAATTA | GTTGATTCA | 660 |
| TGTATGAATA | CTAAATAATT | TTTAGGACT | GACTCAAATA | TTTTATATT | ATCATAGTAA | 720 |
| TATTTATCTA | ATTTTTAGGA | CCACTTATTA | CTAAATAATA | AATTAACTAC | TACTATATTA | 780 |
| TTGTTGTGAA | ACAACAACGT | TTTGGTTGTT | ATGATGAAAC | GTACACTATA | TCAGTATGAA | 840 |
| AAATTCAAAA | CGATTAGTAT | AAATTATATT | GAAATTTGA | TATTTTCTA | TTCTTAATCA | 900 |
| GACGTATTGG | GTTTCATATT | TTAAAAGGG | ACTAAACTTA | GAAGAGAAGT | TTGTTTGAAA | 960 |
| CTACTTTTGT | CTCTTTCTTG | TTCCCATTTC | TCTCTTAGAT | TTCAAAAGT | GAACTACTTT | 1020 |
| ATCTCTTTCT | TTGTTCACAT | TTTATTTAT | TCTATTATAA | ATATGGCATC | CTCATATTGA | 1080 |
| GATTTTAGA | AATTATTCTA | ATCATTCACA | GTGCAAAAGA | AGATCTAAAG | CCCTAGAG | 1138 |

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:11:

CCCGGATCCA TGAATCTGAA TCGTTTT    27

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

CCCGGATCCG CCGTTACGAA ACAGGAA    27

( 2 ) INFORMATION FOR SEQ ID NO:13:

( i ) SEQUENCE CHARACTERISTICS:
        ( A ) LENGTH: 318 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

```
AGATCTATCG ATAAGCTTGA TGTAATTGGA GGAAGATCAA AATTTCAAT CCCCATTCTT          60

CGATTGCTTC AATTGAAGTT CTCCG ATG GCG CAA GTT AGC AGA ATC TGC AAT        113
                            Met Ala Gln Val Ser Arg Ile Cys Asn
                             1               5

GGT GTG CAG AAC CCA TCT CTT ATC TCC AAT CTC TCG AAA TCC AGT CAA        161
Gly Val Gln Asn Pro Ser Leu Ile Ser Asn Leu Ser Lys Ser Ser Gln
 10              15                  20                  25

CGC AAA TCT CCC TTA TCG GTT TCT CTG AAG ACG CAG CAG CAT CCA CGA        209
Arg Lys Ser Pro Leu Ser Val Ser Leu Lys Thr Gln Gln His Pro Arg
         30                  35                  40
```

```
GCT TAT CCG ATT TCG TCG TCG TGG GGA TTG AAG AAG AGT GGG ATG ACG      257
Ala Tyr Pro Ile Ser Ser Ser Trp Gly Leu Lys Lys Ser Gly Met Thr
            45              50              55

TTA ATT GGC TCT GAG CTT CGT CCT CTT AAG GTC ATG TCT TCT GTT TCC      305
Leu Ile Gly Ser Glu Leu Arg Pro Leu Lys Val Met Ser Ser Val Ser
        60              65              70

ACG GCG TGC ATG C                                                    318
Thr Ala Cys Met
    75
```

( 2 ) INFORMATION FOR SEQ ID NO:14:

( i ) SEQUENCE CHARACTERISTICS:
    ( A ) LENGTH: 1377 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

```
GC ATG CTT CAC GGT GCA AGC AGC CGT CCA GCA ACT GCT CGT AAG TCC       47
   Met Leu His Gly Ala Ser Ser Arg Pro Ala Thr Ala Arg Lys Ser
   1                5                   10                  15

TCT GGT CTT TCT GGA ACC GTC CGT ATT CCA GGT GAC AAG TCT ATC TCC      95
Ser Gly Leu Ser Gly Thr Val Arg Ile Pro Gly Asp Lys Ser Ile Ser
            20              25                  30

CAC AGG TCC TTC ATG TTT GGA GGT CTC GCT AGC GGT GAA ACT CGT ATC     143
His Arg Ser Phe Met Phe Gly Gly Leu Ala Ser Gly Glu Thr Arg Ile
            35              40                  45

ACC GGT CTT TTG GAA GGT GAA GAT GTT ATC AAC ACT GGT AAG GCT ATG     191
Thr Gly Leu Leu Glu Gly Glu Asp Val Ile Asn Thr Gly Lys Ala Met
        50              55                  60

CAA GCT ATG GGT GCC AGA ATC CGT AAG GAA GGT GAT ACT TGG ATC ATT     239
Gln Ala Met Gly Ala Arg Ile Arg Lys Glu Gly Asp Thr Trp Ile Ile
    65              70                  75

GAT GGT GTT GGT AAC GGT GGA CTC CTT GCT CCT GAG GCT CCT CTC GAT     287
Asp Gly Val Gly Asn Gly Gly Leu Leu Ala Pro Glu Ala Pro Leu Asp
80              85                  90                      95

TTC GGT AAC GCT GCA ACT GGT TGC CGT TTG ACT ATG GGT CTT GTT GGT     335
Phe Gly Asn Ala Ala Thr Gly Cys Arg Leu Thr Met Gly Leu Val Gly
            100             105                 110

GTT TAC GAT TTC GAT AGC ACT TTC ATT GGT GAC GCT TCT CTC ACT AAG     383
Val Tyr Asp Phe Asp Ser Thr Phe Ile Gly Asp Ala Ser Leu Thr Lys
            115             120                 125

CGT CCA ATG GGT CGT GTG TTG AAC CCA CTT CGC GAA ATG GGT GTG CAG     431
Arg Pro Met Gly Arg Val Leu Asn Pro Leu Arg Glu Met Gly Val Gln
        130             135                 140

GTG AAG TCT GAA GAC GGT GAT CGT CTT CCA GTT ACC TTG CGT GGA CCA     479
Val Lys Ser Glu Asp Gly Asp Arg Leu Pro Val Thr Leu Arg Gly Pro
    145             150                 155

AAG ACT CCA ACG CCA ATC ACC TAC AGG GTA CCT ATG GCT TCC GCT CAA     527
Lys Thr Pro Thr Pro Ile Thr Tyr Arg Val Pro Met Ala Ser Ala Gln
160             165                 170                 175

GTG AAG TCC GCT GTT CTG CTT GCT GGT CTC AAC ACC CCA GGT ATC ACC     575
Val Lys Ser Ala Val Leu Leu Ala Gly Leu Asn Thr Pro Gly Ile Thr
            180             185                 190

ACT GTT ATC GAG CCA ATC ATG ACT CGT GAC CAC ACT GAA AAG ATG CTT     623
Thr Val Ile Glu Pro Ile Met Thr Arg Asp His Thr Glu Lys Met Leu
            195             200                 205

CAA GGT TTT GGT GCT AAC CTT ACC GTT GAG ACT GAT GCT GAC GGT GTG     671
Gln Gly Phe Gly Ala Asn Leu Thr Val Glu Thr Asp Ala Asp Gly Val
```

|  | 210 |  |  |  | 215 |  |  |  | 220 |  |  |  |  |  |
|---|---|---|---|---|---|---|---|---|---|---|---|---|---|---|
| CGT | ACC | ATC | CGT | CTT | GAA | GGT | CGT | GGT | AAG | CTC | ACC | GGT | CAA | GTG | ATT | 719 |
| Arg | Thr | Ile | Arg | Leu | Glu | Gly | Arg | Gly | Lys | Leu | Thr | Gly | Gln | Val | Ile |  |
|  | 225 |  |  |  |  | 230 |  |  |  | 235 |  |  |  |  |  |

GAT GTT CCA GGT GAT CCA TCC TCT ACT GCT TTC CCA TTG GTT GCT GCC    767
Asp Val Pro Gly Asp Pro Ser Ser Thr Ala Phe Pro Leu Val Ala Ala
240             245                 250                     255

TTG CTT GTT CCA GGT TCC GAC GTC ACC ATC CTT AAC GTT TTG ATG AAC    815
Leu Leu Val Pro Gly Ser Asp Val Thr Ile Leu Asn Val Leu Met Asn
                260                 265                     270

CCA ACC CGT ACT GGT CTC ATC TTG ACT CTG CAG GAA ATG GGT GCC GAC    863
Pro Thr Arg Thr Gly Leu Ile Leu Thr Leu Gln Glu Met Gly Ala Asp
            275                 280                 285

ATC GAA GTG ATC AAC CCA CGT CTT GCT GGT GGA GAA GAC GTG GCT GAC    911
Ile Glu Val Ile Asn Pro Arg Leu Ala Gly Gly Glu Asp Val Ala Asp
        290                 295                 300

TTG CGT GTT CGT TCT TCT ACT TTG AAG GGT GTT ACT GTT CCA GAA GAC    959
Leu Arg Val Arg Ser Ser Thr Leu Lys Gly Val Thr Val Pro Glu Asp
    305                 310                 315

CGT GCT CCT TCT ATG ATC GAC GAG TAT CCA ATT CTC GCT GTT GCA GCT   1007
Arg Ala Pro Ser Met Ile Asp Glu Tyr Pro Ile Leu Ala Val Ala Ala
320                 325                 330                 335

GCA TTC GCT GAA GGT GCT ACC GTT ATG AAC GGT TTG GAA GAA CTC CGT   1055
Ala Phe Ala Glu Gly Ala Thr Val Met Asn Gly Leu Glu Glu Leu Arg
                340                 345                 350

GTT AAG GAA AGC GAC CGT CTT TCT GCT GTC GCA AAC GGT CTC AAG CTC   1103
Val Lys Glu Ser Asp Arg Leu Ser Ala Val Ala Asn Gly Leu Lys Leu
            355                 360                 365

AAC GGT GTT GAT TGC GAT GAA GGT GAG ACT TCT CTC GTC GTG CGT GGT   1151
Asn Gly Val Asp Cys Asp Glu Gly Glu Thr Ser Leu Val Val Arg Gly
        370                 375                 380

CGT CCT GAC GGT AAG GGT CTC GGT AAC GCT TCT GGA GCA GCT GTC GCT   1199
Arg Pro Asp Gly Lys Gly Leu Gly Asn Ala Ser Gly Ala Ala Val Ala
    385                 390                 395

ACC CAC CTC GAT CAC CGT ATC GCT ATG AGC TTC CTC GTT ATG GGT CTC   1247
Thr His Leu Asp His Arg Ile Ala Met Ser Phe Leu Val Met Gly Leu
400                 405                 410                 415

GTT TCT GAA AAC CCT GTT ACT GTT GAT GAT GCT ACT ATG ATC GCT ACT   1295
Val Ser Glu Asn Pro Val Thr Val Asp Asp Ala Thr Met Ile Ala Thr
                420                 425                 430

AGC TTC CCA GAG TTC ATG GAT TTG ATG GCT GGT CTT GGA GCT AAG ATC   1343
Ser Phe Pro Glu Phe Met Asp Leu Met Ala Gly Leu Gly Ala Lys Ile
            435                 440                 445

GAA CTC TCC GAC ACT AAG GCT GCT TGATGAGCTC                        1377
Glu Leu Ser Asp Thr Lys Ala Ala
        450                 455

( 2 ) INFORMATION FOR SEQ ID NO:15:

( i ) SEQUENCE CHARACTERISTICS:
        ( A ) LENGTH: 1029 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 7..1020

( x i ) SEQUENCE DESCRIPTION: SEQ ID NO:15:

GGATCC ATG AAT TTG AAT CGT TTT AAA CGT TAT CCG TTG ACC TTC GGT     48

```
                Met Asn Leu Asn Arg Phe Lys Arg Tyr Pro Leu Thr Phe Gly
                 1               5                  10

CCT TCT CCC ATC ACG CCC TTG AAG CGC CTC AGT GAA CAC TTG GGT GGC            96
Pro Ser Pro Ile Thr Pro Leu Lys Arg Leu Ser Glu His Leu Gly Gly
 15              20                  25                  30

AAG GTC GAG CTG TAT GCC AAG CGT GAA GAC TGC AAC AGT GGC CTG GCC           144
Lys Val Glu Leu Tyr Ala Lys Arg Glu Asp Cys Asn Ser Gly Leu Ala
             35                  40                  45

TTC GGC GGG AAC AAA ACG CGC AAG CTC GAA TAT TTG ATT CCC GAA GCG           192
Phe Gly Gly Asn Lys Thr Arg Lys Leu Glu Tyr Leu Ile Pro Glu Ala
                 50                  55                  60

CTC GAG CAA GGC TGC GAT ACC TTG GTT TCC ATC GGC GGC ATC CAG TCG           240
Leu Glu Gln Gly Cys Asp Thr Leu Val Ser Ile Gly Gly Ile Gln Ser
             65                  70                  75

AAC CAG ACC CGC CAG GTG GCC GCC GTT GCC GCT CAC CTG GGC ATG AAG           288
Asn Gln Thr Arg Gln Val Ala Ala Val Ala Ala His Leu Gly Met Lys
         80                  85                  90

TCG GTG CTG GTC GAG GAA AAC TGG GTG AAC TAC TCC GAT GCG GTG TAT           336
Ser Val Leu Val Glu Glu Asn Trp Val Asn Tyr Ser Asp Ala Val Tyr
 95                 100                 105                 110

GAC CGC GTT GGC AAT ATC GAA ATG TCT CGC ATC ATG GGC GCC GAG GTA           384
Asp Arg Val Gly Asn Ile Glu Met Ser Arg Ile Met Gly Ala Glu Val
                115                 120                 125

CGA CTG GAC GCC GCC GGG TTC GAT ATC GGC ATT CGG CCC AGC TGG GAG           432
Arg Leu Asp Ala Ala Gly Phe Asp Ile Gly Ile Arg Pro Ser Trp Glu
            130                 135                 140

AAG GCC ATG GAC GAT GTG GTG GCG CGG GGT GGC AAG CCG TTC CCG ATA           480
Lys Ala Met Asp Asp Val Val Ala Arg Gly Gly Lys Pro Phe Pro Ile
            145                 150                 155

CCG GCG GGT TGT TCC GAA CAC CCC TAC GGC GGC CTT GGG TTC GTC GGC           528
Pro Ala Gly Cys Ser Glu His Pro Tyr Gly Gly Leu Gly Phe Val Gly
160                 165                 170

TTT GCC GAG GAA GTG CGA GAG CAG GAA AAA CAA CTG GGG TTC ACG TTC           576
Phe Ala Glu Glu Val Arg Glu Gln Glu Lys Gln Leu Gly Phe Thr Phe
175                 180                 185                 190

GAC TAC ATC GTG GTC TGC TCT GTG ACC GGC AGT ACC CAG GCC GGC ATG           624
Asp Tyr Ile Val Val Cys Ser Val Thr Gly Ser Thr Gln Ala Gly Met
                195                 200                 205

GTC GTC GGT TTC GCC GCG GAC GGC CGT TCG AAG AAC GTT ATC GGC ATT           672
Val Val Gly Phe Ala Ala Asp Gly Arg Ser Lys Asn Val Ile Gly Ile
            210                 215                 220

GAT GCC TCG GCC AAG CCG GAG CAA ACC AAG GCA CAG ATC CTG CGT ATC           720
Asp Ala Ser Ala Lys Pro Glu Gln Thr Lys Ala Gln Ile Leu Arg Ile
            225                 230                 235

GCC CGG CAC ACC GCA GAG TTG GTG GAA CTG GGC CGT GAG ATC ACC GAA           768
Ala Arg His Thr Ala Glu Leu Val Glu Leu Gly Arg Glu Ile Thr Glu
            240                 245                 250

GAC GAC GTG GTG CTC GAT ACA CGT TTT GCC TAC CCG GAA TAC GGT TTG           816
Asp Asp Val Val Leu Asp Thr Arg Phe Ala Tyr Pro Glu Tyr Gly Leu
255                 260                 265                 270

CCC AAC GAA GGC ACG CTG GAA GCC ATT CGT TTG TGC GGG AGC CTG GAA           864
Pro Asn Glu Gly Thr Leu Glu Ala Ile Arg Leu Cys Gly Ser Leu Glu
                275                 280                 285

GGT GTG CTG ACC GAT CCG GTG TAC GAG GGC AAA TCC ATG CAC GGG ATG           912
Gly Val Leu Thr Asp Pro Val Tyr Glu Gly Lys Ser Met His Gly Met
            290                 295                 300

ATT GAA ATG GTC CGC CGT GGC GAG TTC CCC GAA GGC TCC AAA GTG CTG           960
Ile Glu Met Val Arg Arg Gly Glu Phe Pro Glu Gly Ser Lys Val Leu
            305                 310                 315

TAT GCG CAC TTG GGT GGG GCG CCT GCG CTG AAT GCC TAC AGC TTC CTG          1008
```

| | | | | | | | | | | | | | |
|---|---|---|---|---|---|---|---|---|---|---|---|---|---|
|Tyr|Ala|His|Leu|Gly|Gly|Ala|Pro|Ala|Leu|Asn|Ala|Tyr|Ser|Phe|Leu|
| |320| | | |325| | | |330| | | | | |

```
TTT CGT AAC GGC GGATCCGGG                                              1029
Phe Arg Asn Gly
335
```

( 2 ) INFORMATION FOR SEQ ID NO:16:

( i ) SEQUENCE CHARACTERISTICS:
        ( A ) LENGTH: 338 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| | | | | | | | | | | | | | | |
|---|---|---|---|---|---|---|---|---|---|---|---|---|---|---|
|Met|Asn|Leu|Asn|Arg|Phe|Lys|Arg|Tyr|Pro|Leu|Thr|Phe|Gly|Pro|Ser|
|1| | | |5| | | |10| | | |15| | |
|Pro|Ile|Thr|Pro|Leu|Lys|Arg|Leu|Ser|Glu|His|Leu|Gly|Gly|Lys|Val|
| | | |20| | | |25| | | |30| | | |
|Glu|Leu|Tyr|Ala|Lys|Arg|Glu|Asp|Cys|Asn|Ser|Gly|Leu|Ala|Phe|Gly|
| | |35| | | |40| | | |45| | | | |
|Gly|Asn|Lys|Thr|Arg|Lys|Leu|Glu|Tyr|Leu|Ile|Pro|Glu|Ala|Leu|Glu|
| |50| | | |55| | | |60| | | | | |
|Gln|Gly|Cys|Asp|Thr|Leu|Val|Ser|Ile|Gly|Gly|Ile|Gln|Ser|Asn|Gln|
|65| | | |70| | | |75| | | | | |80|
|Thr|Arg|Gln|Val|Ala|Ala|Val|Ala|Ala|His|Leu|Gly|Met|Lys|Ser|Val|
| | | | |85| | | |90| | | |95| | |
|Leu|Val|Glu|Glu|Asn|Trp|Val|Asn|Tyr|Ser|Asp|Ala|Val|Tyr|Asp|Arg|
| | | |100| | | |105| | | |110| | | |
|Val|Gly|Asn|Ile|Glu|Met|Ser|Arg|Ile|Met|Gly|Ala|Glu|Val|Arg|Leu|
| | |115| | | |120| | | |125| | | | |
|Asp|Ala|Ala|Gly|Phe|Asp|Ile|Gly|Ile|Arg|Pro|Ser|Trp|Glu|Lys|Ala|
| |130| | | |135| | | |140| | | | | |
|Met|Asp|Asp|Val|Val|Ala|Arg|Gly|Gly|Lys|Pro|Phe|Pro|Ile|Pro|Ala|
|145| | | |150| | | |155| | | | | |160|
|Gly|Cys|Ser|Glu|His|Pro|Tyr|Gly|Gly|Leu|Gly|Phe|Val|Gly|Phe|Ala|
| | | |165| | | |170| | | |175| | | |
|Glu|Glu|Val|Arg|Glu|Gln|Glu|Lys|Gln|Leu|Gly|Phe|Thr|Phe|Asp|Tyr|
| | |180| | | |185| | | |190| | | | |
|Ile|Val|Val|Cys|Ser|Val|Thr|Gly|Ser|Thr|Gln|Ala|Gly|Met|Val|Val|
| |195| | | |200| | | |205| | | | | |
|Gly|Phe|Ala|Ala|Asp|Gly|Arg|Ser|Lys|Asn|Val|Ile|Gly|Ile|Asp|Ala|
|210| | | |215| | | |220| | | | | | |
|Ser|Ala|Lys|Pro|Glu|Gln|Thr|Lys|Ala|Gln|Ile|Leu|Arg|Ile|Ala|Arg|
|225| | | |230| | | |235| | | | | |240|
|His|Thr|Ala|Glu|Leu|Val|Glu|Leu|Gly|Arg|Glu|Ile|Thr|Glu|Asp|Asp|
| | | |245| | | |250| | | |255| | | |
|Val|Val|Leu|Asp|Thr|Arg|Phe|Ala|Tyr|Pro|Glu|Tyr|Gly|Leu|Pro|Asn|
| | |260| | | |265| | | |270| | | | |
|Glu|Gly|Thr|Leu|Glu|Ala|Ile|Arg|Leu|Cys|Gly|Ser|Leu|Glu|Gly|Val|
| |275| | | |280| | | |285| | | | | |
|Leu|Thr|Asp|Pro|Val|Tyr|Glu|Gly|Lys|Ser|Met|His|Gly|Met|Ile|Glu|
|290| | | |295| | | |300| | | | | | |
|Met|Val|Arg|Arg|Gly|Glu|Phe|Pro|Glu|Gly|Ser|Lys|Val|Leu|Tyr|Ala|
|305| | | |310| | | |315| | | | | |320|
|His|Leu|Gly|Gly|Ala|Pro|Ala|Leu|Asn|Ala|Tyr|Ser|Phe|Leu|Phe|Arg|

Asn Gly (2) INFORMATION FOR SEQ ID NO:17:

(i) SEQUENCE CHARACTERISTICS:
(A) LENGTH: 597 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:17:

| | | | | | | |
|---|---|---|---|---|---|---|
| TCATCAAAAT | ATTTAGCAGC | ATTCCAGATT | GGGTTCAATC | AACAAGGTAC | GAGCCATATC | 60 |
| ACTTTATTCA | AATGGTATC | GCCAAAACCA | AGAAGGAACT | CCCATCCTCA | AAGGTTTGTA | 120 |
| AGGAAGAATT | CTCAGTCCAA | AGCCTCAACA | AGGTCAGGGT | ACAGAGTCTC | CAAACCATTA | 180 |
| GCCAAAAGCT | ACAGGAGATC | AATGAAGAAT | CTTCAATCAA | AGTAAACTAC | TGTTCCAGCA | 240 |
| CATGCATCAT | GGTCAGTAAG | TTTCAGAAAA | AGACATCCAC | CGAAGACTTA | AAGTTAGTGG | 300 |
| GCATCTTTGA | AAGTAATCTT | GTCAACATCG | AGCAGCTGGC | TTGTGGGGAC | CAGACAAAAA | 360 |
| AGGAATGGTG | CAGAATTGTT | AGGCGCACCT | ACCAAAAGCA | TCTTTGCCTT | TATTGCAAAG | 420 |
| ATAAAGCAGA | TTCCTCTAGT | ACAAGTGGGG | AACAAAATAA | CGTGGAAAAG | AGCTGTCCTG | 480 |
| ACAGCCCACT | CACTAATGCG | TATGACGAAC | GCAGTGACGA | CCACAAAAGA | ATTCCCTCTA | 540 |
| TATAAGAAGG | CATTCATTCC | CATTGAAGG | ATCATCAGAT | ACTAACCAAT | ATTTCTC | 597 |

We claim:

1. A recombinant, double stranded DNA molecule comprising in sequence in the 5' to 3' direction:
   a promoter that functions in plant cells to cause the production of an RNA sequence, said promoter operably linked to;
   a structural DNA sequence that causes the production of an RNA sequence that encodes a 1-aminocyclopropane-1-carboxylic acid deaminase enzyme, said structural DNA sequence operably linked to;
   a 3' non-translated region that functions in plant cells to polyadenylate the 3' end of said RNA sequence;
   wherein said promoter is heterologous with respect to said structural DNA sequence.

2. The DNA molecule of claim 1 wherein said promoter is a plant DNA virus promoter.

3. The DNA molecule of claim 2 wherein said promoter is selected from the group consisting of the CaMV35S promoter and the FMV35S promoter.

4. The DNA molecule of claim 1 wherein said promoter is a fruit specific promoter.

5. The DNA molecule of claim 1 wherein said structural DNA sequence is SEQ ID NO:1.

6. The DNA molecule of claim 1 wherein said structural DNA sequence is from a microorganism capable of sustaining growth in media containing ACC as the sole nitrogen source.

7. A method for producing fruit-bearing plants, wherein the fruit exhibit a delayed ripening phenotype, said method comprising the steps of:
   obtaining regenerable cells of said fruit-bearing plant;
   transforming said cells of said fruit-bearing plant by inserting into the genome of said cells a recombinant, double-stranded DNA molecule, said molecule comprising in sequence in the 5' to 3' direction a promoter that functions in plant cells to cause the production of an RNA sequence, said promoter operably linked to; a structural DNA sequence that causes the production of an RNA sequence that encodes a 1-aminocyclopropane-1-carboxylic acid deaminase enzyme, said structural DNA sequence operably linked to; a 3' non-translated region that functions in plant cells to polyadenylate the 3' end of said RNA sequence;
   wherein said promoter is heterologous with respect to said structural DNA sequence, and wherein said DNA molecule becomes integrated into the genome of said plant cell; regenerating a plant from said transformed plant cell and growing said transformed fruit-bearing plant to produce fruit.

8. The method of claim 7 wherein said promoter is a plant DNA virus promoter.

9. The method of claim 8 wherein said promoter is selected from the group consisting of the CaMV35S promoter and the FMV35S promoter.

10. The method of claim 7 wherein said promoter is a fruit specific promoter.

11. The method of claim 7 wherein said structural DNA sequence is SEQ ID NO:1.

12. The method of claim 7 wherein said structural DNA sequence is from a microorganism capable of sustaining growth in media containing ACC as the sole nitrogen source.

13. A method for producing fruit-bearing plants wherein said fruit exhibits a delayed ripening phenotype comprising expressing a gene encoding 1-aminocyclopropane-1-carboxylic acid deaminase in said plant at a level sufficient to reduce the production of ethylene in said fruit.

14. A transformed plant which exhibits a delayed ripening phenotype, said plant containing in its genome a recombinant, double-stranded DNA molecule, said molecule comprising in sequence in the 5' to 3' direction: a promoter that functions in plant cells to cause the production of an RNA sequence, said promoter operably linked to; a structural DNA sequence that causes the production of an RNA sequence that encodes a 1-aminocyclopropane-1-carboxylic acid deaminase enzyme, said structural DNA sequence operably linked to; a 3' non-translated region that functions in plant cells to polyadenylate the 3' end of said RNA sequence; wherein said promoter is heterologous with respect to said structural DNA sequence and wherein plant cells from said plant are capable of being transformed with said DNA molecule.

15. The transformed plant of claim 14 wherein said plant is selected from the group consisting of banana, kiwifruit, avocado, melon, strawberry, mango, papaya, apple, peach, cabbage, cauliflower, lettuce, onions, broccoli, cotton, canola, oilseed rape, carnations, and roses.

16. The transformed plant of claim 14 wherein said structural DNA sequence is SEQ ID NO:1.

17. A method for producing a plant with reduced levels of ethylene which comprises expressing a gene encoding a 1-aminocyclopropane-1-carboxylic acid metabolizing enzyme in said plant at a sufficient level to reduce the steady-state 1-aminocyclopropane-1-carboxylic acid concentration, wherein said 1-aminocyclopropane-1-carboxylic acid metabolizing enzyme is 1-aminocyclopropane-1-carboxylic acid deaminase.

18. A method for producing a plant with a reduced level of ethylene which comprises expressing a gene encoding a 1-aminocyclopropane-1-carboxylic acid metabolizing enzyme in said plant at a sufficient level to reduce the steady-state ethylene concentration by at least about 70%, wherein said 1-aminocyclopropane-1-carboxylic acid metabolizing enzyme is 1-aminocyclopropane-1-carboxylic acid deaminase.

19. A method of claim 18 in which the steady-state ethylene concentration is reduced by at least about 90%.

* * * * *